US007989394B2

(12) United States Patent
Kordes et al.

(10) Patent No.: US 7,989,394 B2
(45) Date of Patent: Aug. 2, 2011

(54) SUBSTITUTED 1-(AZOLIN-2-YL)-AMINO-2-ARYL-1-HETARYL-ETHANE COMPOUNDS

(75) Inventors: Markus Kordes, Bobenheim-Roxheim (DE); Delphine Breuninger, Bobenheim-Roxheim (DE); Ronan Le Vezouet, Mannheim (DE); Christopher Koradin, Ludwigshafen (DE); Livio Tedeschi, Stockport (GB); Michael Puhl, Lampertheim (DE); Deborah L. Culbertson, Fuquay Varina, NC (US)

(73) Assignee: BASF SE, Ludwigshafen (DE)

( * ) Notice: Subject to any disclaimer, the term of this patent is extended or adjusted under 35 U.S.C. 154(b) by 46 days.

(21) Appl. No.: 12/305,419

(22) PCT Filed: Jun. 29, 2007

(86) PCT No.: PCT/EP2007/056604
§ 371 (c)(1),
(2), (4) Date: Dec. 18, 2008

(87) PCT Pub. No.: WO2008/000834
PCT Pub. Date: Jan. 3, 2008

(65) Prior Publication Data
US 2009/0131256 A1    May 21, 2009

Related U.S. Application Data

(60) Provisional application No. 60/817,973, filed on Jun. 30, 2006.

(51) Int. Cl.
*A01N 43/76* (2006.01)
*A01N 43/78* (2006.01)
*C07D 277/04* (2006.01)
*C07D 277/08* (2006.01)

(52) U.S. Cl. ........ 504/266; 548/146; 548/190; 548/215; 548/233

(58) Field of Classification Search .................. 504/266; 548/146, 190, 215
See application file for complete search history.

(56) References Cited

U.S. PATENT DOCUMENTS

| 5,296,486 A | 3/1994 | Lazer et al. |
| 7,655,600 B2 * | 2/2010 | Kordes et al. ............ 504/266 |

FOREIGN PATENT DOCUMENTS

| EP | 097013 | 12/1983 |
| WO | WO 03/086271 A2 | 10/2003 |
| WO | WO 03/086271 A3 | 10/2003 |
| WO | WO 2005/063724 | 7/2005 |
| WO | WO 2006/127426 A2 | 11/2006 |
| WO | WO 2006/127426 A3 | 11/2006 |
| WO | WO 2007/071585 | 6/2007 |

OTHER PUBLICATIONS

International Search Report for International Application No. PCT/EP2007/056604;m International Filing Date: Jun. 29, 2007; Date of Completion: Oct. 16, 2007; Date of Mailing: Oct. 24, 2007.

K. R. Jennings et al., "A biorationally synthesized octopaminergic insecticide, 2-(4-chloro-o-toluidino)-2-oxazoline", Pesticide Biochemistry and Physiology, 30, 190-197 (1988) XP009046959, Search Report.

\* cited by examiner

*Primary Examiner* — Susannah Chung
(74) *Attorney, Agent, or Firm* — Brinks Hofer Gilson & Lione

(57) ABSTRACT

The present invention relates to 1-(azolin-2-yl)-amino-2-aryl-1-hetaryl-ethane compounds (I) and 1-(aminothiocarbonylamino)-2-aryl-1-hetaryl-ethane compounds (II) and their salts which are useful for combating animal pest, in particular insects, arachnids and nematodes. Furthermore, the present invention relates to a method for combating animal pests selected from insects, arachnids and nematodes, and to agricultural compositions for combating animal pests. Furthermore, the present invention relates to veterinary compositions for combating animal pests.

23 Claims, No Drawings

SUBSTITUTED 1-(AZOLIN-2-YL)-AMINO-2-ARYL-1-HETARYL-ETHANE COMPOUNDS

This application is a National Stage application of International Application No. PCT/EP2007/056604 filed Jun. 29, 2007, which claims the benefit of U.S. Provisional Application No. 60/817,973, filed Jun. 30, 2006, the entire contents of which is hereby incorporated herein by reference.

The present invention relates to 1-(azolin-2-yl)-amino-2-aryl-1-hetaryl-ethane compounds and 1-(aminothiocarbonylamino)-2-aryl-1-hetaryl-ethane compounds and their salts which are useful for combating animal pest, in particular insects, arachnids and nematodes. The present invention also relates to a method for combating such pests and for protecting crops against infestation or infection by such pests. Furthermore, the present invention relates to veterinary compositions for combating animal pests.

Animal pests and in particular insects, arachnids and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating insects, arachnids and nematodes.

EP 097013 discloses hetarylalkyl azoline compounds which are useful as fungicides and aquatic plant growth regulators.

WO 2005/063724 describes 1-(azolin-2-yl)amino-1,2-diphenylethane compounds which are useful for combating insects, arachnids and nematodes.

Unpublished U.S. application Ser. No. 60/753,367 discloses 1-(azolin-2-yl)-amino-1-phenyl-2-hetaryl-ethane compounds for combating insects, arachnids and nematodes. However, the pesticidal action of the compounds disclosed in the above-mentioned literature references is not always completely satisfying.

It is therefore an object of the present invention to provide compounds having a good pesticidal activity and showing a broad activity spectrum against a large number of different animal pests, especially against difficult to control insects, arachnids and nematodes.

It has been found that these objectives can be achieved by 1-(azolin-2-yl)-amino-2-phenylaryl-1-hetaryl-ethane compounds of the general formula I

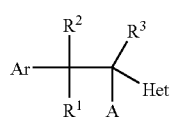

wherein $R^1$, $R^2$, $R^3$ are, independently of each other, selected from hydrogen, $C_1$-$C_6$-alkyl, $C_1$-$C_6$-haloalkyl, $C_3$-$C_6$-cycloalkyl, $C_3$-$C_6$-halocycloalkyl, wherein 1, 2 or 3 hydrogen atoms in the aforementioned aliphatic radicals may be replaced, independently of one another, by a radical selected from the group consisting of cyano, nitro, hydroxy, mercapto, amino, carboxyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, and wherein $C_3$-$C_6$-cycloalkyl and $C_3$-$C_6$-halocycloalkyl may also carry 1, 2, 3, 4 or 5 radicals selected from $C_1$-$C_6$-alkyl and $C_1$-$C_6$-haloalkyl, phenyl or benzyl, wherein the phenyl ring in the last two mentioned radicals may be unsubstituted or may carry 1, 2, 3, 4 or 5 radicals which are, independently of each other, selected from the group consisting of halogen, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy and $C_1$-$C_6$-haloalkoxy;

A is a radical of the formulae $A^1$ or $A^2$:

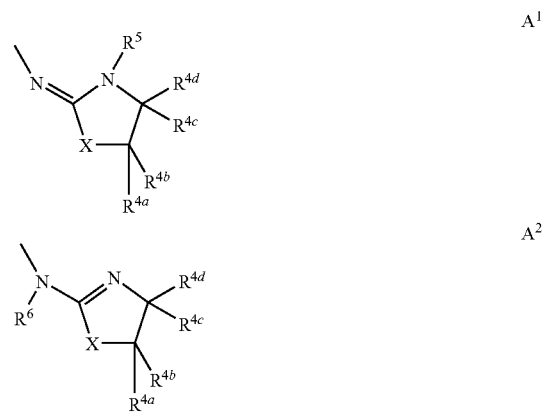

wherein

X is sulfur, oxygen or $NR^7$;

$R^{4a}$, $R^{4b}$, $R^{4c}$, $R^{4d}$ are, independently of each other, selected from the group consisting of hydrogen, halogen, $C_1$-$C_6$-alkyl, $C_1$-$C_6$-haloalkyl, $C_1$-$C_6$-alkylamino, $C_1$-$C_6$-alkoxy, $C_1$-$C_6$-haloalkoxy, $C_3$-$C_6$-cycloalkyl and $C_3$-$C_6$-halocycloalkyl, wherein 1, 2 or 3 hydrogen atoms in the aforementioned aliphatic radicals may be replaced, independently of one another, by a radical selected from the group consisting of cyano, nitro, hydroxy, mercapto, amino, carboxyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio and wherein $C_3$-$C_6$-cycloalkyl and $C_3$-$C_6$-halocycloalkyl may also carry 1, 2, 3, 4 or 5 radicals selected from $C_1$-$C_6$-alkyl and $C_1$-$C_6$-haloalkyl;

$R^5$, $R^6$, $R^7$ are, independently of each other, selected from the group consisting of hydrogen, cyano, nitro, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkoxy)methylen, $C_1$-$C_6$-alkylthio, $C_1$-$C_6$-alkylsulfinyl, $C_1$-$C_6$-alkylsulfonyl, wherein the aliphatic moieties in the aforementioned radicals may be unsubstituted, partially or completely halogenated and/or may carry 1, 2 or 3 radicals, which are independently of one another, selected from the group consisting of cyano, nitro, hydroxy, mercapto, amino, carboxyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio and wherein $C_3$-$C_8$-cycloalkyl and $C_3$-$C_8$-halocycloalkyl may also carry 1, 2, 3, 4 or 5 radicals selected from $C_1$-$C_6$-alkyl and $C_1$-$C_6$-haloalkyl, $C(O)NR^aR^b$, $(SO_2)NR^aR^b$ or $C(\!=\!O)R^c$, phenyl, phenyloxy or benzyl, wherein the phenyl ring in each of the last three mentioned radicals may be unsubstituted or may carry 1, 2, 3, 4 or 5 radicals, independently of one another selected from the group consisting of halogen, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy and $C_1$-$C_6$-haloalkoxy radicals;

Het is a 5- or 6-membered heteroaromatic ring which contains 1, 2, 3 or 4 heteroatoms selected from oxygen, nitrogen and sulfur as ring members, wherein the heteroaromatic ring may be fused to a ring selected from phenyl, a saturated or partially unsaturated 5-, 6-, or 7-membered carbocycle and a fused 5-, 6- or 7-membered saturated, partially unsaturated or aromatic heterocycle, which contains 1, 2 or 3 heteroatoms selected from oxygen, sulfur and nitrogen atoms as ring members, and wherein the 5- or 6-membered heteroaromatic ring and/or the respective fused ring carry at their carbon atoms any combination of m radicals $R^8$ and/or may carry at its nitrogen atom, if present, a radical $R^9$ or oxygen:

m is 0, 1, 2, 3 or 4, $R^8$ is selected from halogen, OH, SH, $NH_2$, $SO_3H$, COOH, cyano, azido, nitro, $CONH_2$, $CSNH_2$, CH=N—OH, CH=N—O—$(C_1-C_6)$-alkyl, $C_1-C_6$-alkyl, $C_2-C_6$-alkenyl, $C_2-C_6$-alkynyl, $C_3-C_8$-cycloalkyl, $C_1-C_6$-alkylamino, $C_2-C_6$-alkenylamino, $C_2-C_6$-alkynylamino, di($C_1-C_6$-alkyl)amino, di($C_2-C_6$-alkenyl)amino, di($C_2-C_6$-alkynyl)amino, $C_1-C_6$-alkylthio, $C_2-C_6$-alkenylthio, $C_2-C_6$-alkynylthio, $C_1-C_6$-alkylsulfonyl, $C_2-C_6$-alkenyl-sulfonyl, $C_2-C_6$-alkynylsulfonyl, ($C_1-C_6$-alkyl)carbonyl, ($C_2-C_6$-alkenyl)carbonyl, ($C_2-C_6$-alkynyl)-carbonyl, $C_1-C_6$-alkoxy, $C_2-C_6$-alkenyloxy, $C_2-C_6$-alkynyloxy, ($C_1-C_6$-alkoxy)carbonyl, ($C_2-C_6$-alkenyloxy)carbonyl, ($C_2-C_6$-alkynyloxy)-carbonyl, ($C_1-C_6$-alkyl)carbonyloxy, ($C_2-C_6$-alkenyl)carbonyloxy, ($C_2-C_6$-alkynyl)carbonyloxy, ($C_1-C_6$-alkyl)carbonyl-amino, ($C_2-C_6$-alkenyl)carbonyl-amino, ($C_2-C_6$-alkynyl)carbonyl-amino, wherein the aliphatic parts of the aforementioned groups may be unsubstituted, partially or completely halogenated or may carry any combination of one, two or three radicals, independently of one another selected from the group consisting of cyano, nitro, hydroxy, mercapto, amino, carboxyl, $C_1-C_6$-alkyl, $C_2-C_6$-alkenyl, $C_2-C_6$-alkynyl, $C_1-C_6$-alkoxy, $C_2-C_6$-alkenyloxy, $C_2-C_6$-alkynyloxy, $C_1-C_6$-haloalkoxy, $C_1-C_6$-haloalkyl and $C_1-C_6$-alkylthio;

$C(O)NR^aR^b$, $(SO_2)NR^aR^b$, $C(=O)R^c$, $C(=S)R^c$, a radical Y—Ar' or a radical Y-Cy, wherein Y is a single bond, O, S, NH, $C_1-C_6$-alkandiyl or $C_1-C_6$-alkandiyloxy, Ar' is phenyl, naphthyl or a mono- or bicyclic 5- to 10-membered heteroaromatic ring, which contains 1, 2, 3 or 4 heteroatoms selected from oxygen, sulfur and nitrogen atoms as ring members, wherein Ar' is unsubstituted or may carry any combination of 1, 2, 3, 4 or 5 radicals, independently of one another selected from the group consisting of halogen, cyano, nitro, hydroxy, mercapto, amino, carboxyl, $C_1-C_6$-alkyl, $C_1-C_6$-haloalkyl, $C_1-C_6$-alkoxy, $C_2-C_6$-alkenyloxy, $C_2-C_6$-alkynyloxy, $C_1-C_6$-haloalkoxy and $C_1-C_6$-alkylthio;

Cy is $C_3-C_8$-cycloalkyl, which is unsubstituted or may carry any combination of 1, 2, 3, 4 or 5 radicals, independently of one another selected from the group consisting of halogen, cyano, nitro, hydroxy, mercapto, amino, carboxyl, $C_1-C_6$-alkyl, $C_1-C_6$-haloalkyl, $C_1-C_6$-alkoxy, $C_2-C_6$-alkenyloxy, $C_2-C_6$-alkynyloxy, $C_1-C_6$-haloalkoxy and $C_1-C_6$-alkylthio;

$R^9$ has one of the meanings given for $R^5$;

Ar is a phenyl or naphthyl which carry any combination of n radicals $R^{10}$:

n is 0, 1, 2, 3, 4 or 5, $R^{10}$ has one of the meanings given for $R^8$;

and wherein two radicals $R^{10}$ that are bound to adjacent carbon atoms of the phenyl ring may also form, together with said carbon atoms, a fused benzene ring, a fused saturated or partially unsaturated 5-, 6-, or 7-membered carbocycle or a fused 5-, 6- or 7-membered saturated, partially unsaturated or aromatic heterocycle, which contains 1, 2, 3 or 4 heteroatoms selected from oxygen, sulfur and nitrogen atoms as ring members, and wherein the fused ring is unsubstituted or may carry 1, 2, 3 or 4 radicals, independently of one another selected from the group consisting of halogen, cyano, nitro, hydroxy, mercapto, amino, carboxyl, $C_1-C_6$-alkyl, $C_1-C_6$-alkoxy, $C_2-C_6$-alkenyloxy, $C_2-C_6$-alkynyloxy, $C_1-C_6$-haloalkoxy and $C_1-C_6$-alkylthio;

and wherein $R^a$ and $R^b$ are each independently from one another selected from hydrogen, $C_1-C_6$-alkyl, $C_1-C_6$-haloalkyl, $C_2-C_6$-alkenyl, $C_2-C_6$-haloalkenyl, $C_2-C_6$-alkynyl, or $C_2-C_6$-haloalkynyl, wherein 1, 2 or 3 hydrogen atoms in the aforementioned aliphatic radicals may be replaced, independently of one another, by a radical selected from the group consisting of cyano, nitro, hydroxy, mercapto, amino, carboxyl, $C_1-C_6$-alkyl, $C_2-C_6$-alkenyl, $C_2-C_6$-alkynyl, $C_1-C_6$-alkoxy, $C_2-C_6$-alkenyloxy, $C_2-C_6$-alkynyloxy, $C_1-C_6$-haloalkoxy, $C_1-C_6$-haloalkyl and $C_1-C_6$-alkylthio; and $R^c$ is selected from hydrogen, $C_1-C_6$-alkyl, $C_2-C_6$-alkenyl, $C_2-C_6$-alkynyl, $C_3-C_8$-cycloalkyl, $C_1-C_6$-alkylthio, $C_1-C_6$-alkoxy, ($C_1-C_6$-alkyl)amino, di($C_1-C_6$-alkyl)amino, hydrazino, ($C_1-C_6$-alkyl)hydrazino, di($C_1-C_6$-alkyl)-hydrazino, wherein the aliphatic parts of the aforementioned groups may be unsubstituted, partially or completely halogenated or may carry any combination of one, two or three radicals, independently of one another selected from the group consisting of cyano, nitro, hydroxy, mercapto, amino, carboxyl, $C_1-C_6$-alkyl, $C_2-C_6$-alkenyl, $C_2-C_6$-alkynyl, $C_1-C_6$-alkoxy, $C_2-C_6$-alkenyloxy, $C_2-C_6$-alkynyloxy, $C_1-C_6$-haloalkoxy, $C_1-C_6$-haloalkyl and $C_1-C_6$-alkylthio, phenyl, and a mono- or bicyclic 5- to 10-membered heteroaromatic ring, which contains 1, 2, 3 or 4 heteroatoms selected from oxygen, sulfur and nitrogen atoms as ring members, wherein phenyl and the heteroaromatic ring are unsubstituted or may carry any combination of 1, 2, 3, 4 or 5 radicals, independently of one another selected from the group consisting of halogen, cyano, nitro, hydroxy, mercapto, amino, carboxyl, $C_1-C_6$-alkyl, $C_1-C_6$-haloalkyl, $C_1-C_6$-alkoxy, $C_2-C_6$-alkenyloxy, $C_2-C_6$-alkynyloxy, $C_1-C_6$-haloalkoxy and $C_1-C_6$-alkylthio;

and the salts thereof.

Therefore, the present invention relates to 1-(azolin-2-yl)-amino-2-aryl-1-hetaryl-ethane compounds of the general formula I and the salts thereof. These compounds have a high pesticidal activity and are active against a broad spectrum of animal pests selected from insects, arachnids and nematodes.

The compounds of formula I and their salts are particularly useful for combating animal pests. The present invention provides the use of compounds of formula I and the salts thereof for protecting plants against damage by animal pest.

Accordingly, the present invention also relates to a method for combating animal pests, in particular insects, arachnids and nematodes, by treating said pest with at least one compound of formula I and/or salt thereof. The method comprises contacting the animal pests, or the environment in which the animal pests live or grow or may live or grow or the materials, plants, seeds, soils, surfaces or spaces to be protected from animal attack or infestation with at least one 1-(azolin-2-yl)-amino-2-aryl-1-hetaryl-ethane compound of the formula I and/or salt thereof.

The present invention also provides a method for protecting crops from attack or infestation by animal pests, in particular insects, arachnids and nematodes. Said method comprises contacting a crop with at least one 1-(azolin-2-yl)-amino-2-aryl-1-hetaryl-ethane compound of formula I and/or salt thereof.

Furthermore, the present invention provides a method for the protection of seeds from soil insects and of the seedlings' roots and shoots from insects. Said method comprises contacting the seeds before sowing and/or after pregermination with at least one 1-(azolin-2-yl)-amino-2-aryl-1-hetaryl-ethane compound of formula I and/or salt thereof.

Furthermore, the invention relates to seed, comprising at least one 1-(azolin-2-yl)-amino-2-aryl-1-hetaryl-ethane compound of formula I and/or salt thereof.

Accordingly, the invention further provides compositions for combating animal pests, comprising at least one 1-(azolin-2-yl)-amino-2-aryl-1-hetaryl-ethane compound of the general formula I and/or salt thereof, and at least one carrier material. Thus, the present invention relates to agricultural compositions for combating such pests, in particular insects, nematodes or arachnids, preferably in the form of directly sprayable solutions, emulsions, pastes oil dispersions, powders, materials for scattering, dusts or in the form of granules, which comprise at least one 1-(azolin-2-yl)-amino-2-aryl-1-hetaryl-ethane compound of the general formula I and/or an agriculturally useful salt thereof and at least one agriculturally acceptable carrier.

The present invention also provides the use of compounds of formula I and the salts thereof for combating parasites in and on animals.

Accordingly, the present invention also relates to a method for protecting animals against infestation or infection by parasites which comprises administering a parasitically effective amount of at least one 1-(azolin-2-yl)-amino-2-aryl-1-hetaryl-ethane compound of formula I and/or salt thereof to the animal in need thereof.

The present invention also relates to a method for treating animals infestated or infected by parasites which comprises administering a parasitically effective amount of at least one 1-(azolin-2-yl)-amino-2-aryl-1-hetaryl-ethane compound of formula I and/or salt thereof to the animal in need thereof.

Accordingly, the present invention provides a veterinary composition comprising at least one 1-(azolin-2-yl)-amino-2-aryl-1-hetaryl-ethane compound of formula I and/or a veterinary useful salt thereof and at least one veterinary acceptable carrier.

Furthermore, the invention provides 1-(aminothiocarbonylamino)-2-aryl-1-hetaryl-ethane compound of the general formula II

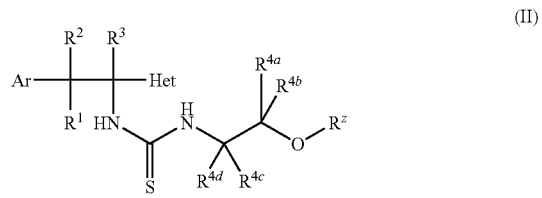

(II)

wherein Het, Ar, $R^1$, $R^2$, $R^3$, $R^{4a}$, $R^{4b}$, $R^{4c}$ and $R^{4d}$ have the meanings given above and wherein $R^z$ is hydrogen, or acetyl and the salts thereof. These compounds have a high pesticidal activity and are active against a broad spectrum of animal pests, in particular against insects, arachnids and nematodes. Therefore, the compounds of the formula II and their salts can be used in similar methods and compositions as described for the compounds of the formula I.

The compounds of the formulae I and II may have one or more centers of chirality, in which case they are present as mixtures of stereoisomers, such as enantiomers or diastereomers. The present invention provides both the pure stereoisomers, e.g. the pure enantiomes or diastereomers, and mixtures thereof. The compounds of formulae I and II may also exist in the form of different tautomers. The invention comprises the single tautomers, if separable, as well as the tautomer mixtures. The scope of the present invention includes the (R)- and (S)-isomers and the racemates of compounds of formulae I and II having chiral centers Salts of the compounds of the formulae I and II are preferably agriculturally or veterinarily acceptable salts. They can be formed in a customary method, e.g. by reacting the compound with an acid of the anion in question if the compound of formulae I and II, respectively, has a basic functionality or by reacting an acidic compound of formulae I and II, respectively, with a suitable base.

Suitable agriculturally useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)-ethylammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

Examples of other meanings are:

The term "$C_1$-$C_6$-alkyl" as used herein and in the alkyl moieties of $C_1$-$C_6$-alkoxy, $C_1$-$C_6$-alkylamino, di($C_1$-$C_6$-alkyl)amino, $C_1$-$C_6$-alkylthio, $C_1$-$C_6$-alkylsulfonyl, $C_1$-$C_6$- alkylsulfoxyl, $C_1$-$C_6$-alkylcarbonyl, $C_1$-$C_6$-alkoxycarbonyl, $C_1$-$C_6$-alkylthiocarbonyl, and $C_1$-$C_6$-alkylcarbonyloxy refer to a saturated straight-chain or branched hydrocarbon group having 1 to 6 carbon atoms, especially 1 to 4 carbon groups, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. $C_1$-$C_4$-alkyl means for example methyl, ethyl, propyl, 1-methylethyl, butyl, 1-methylpropyl, 2-methylpropyl or 1,1-dimethylethyl.

The term "$C_1$-$C_6$-haloalkyl" as used herein refers to a straight-chain or branched saturated alkyl group having 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "$C_1$-$C_6$-alkoxy" as used herein refers to a straight-chain or branched saturated alkyl group having 1 to 6 carbon atoms (as mentioned above) which is attached via an oxygen atom. Examples include $C_1$-$C_6$-alkoxy such as methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethyl butoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "$C_1$-$C_6$-haloalkoxy" as used herein refers to a $C_1$-$C_6$-alkoxy group as mentioned above wherein the hydrogen atoms are partially or fully substituted by fluorine, chlorine, bromine and/or iodine, i.e., for example, $C_1$-$C_6$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy.

The term "$C_1$-$C_6$-alkoxy-$C_1$-$C_6$-alkyl" as used herein refers to $C_1$-$C_6$-alkyl wherein 1 carbon atom carries a $C_1$-$C_6$-alkoxy radical as mentioned above. Examples are $CH_2$—$OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)-ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl and the like.

The term "($C_1$-$C_6$-alkyl)carbonyl" as used herein refers to a straight-chain or branched saturated alkyl group having 1 to 6 carbon atoms (as mentioned above) bonded via the carbon atom of the carbonyl group at any bond in the alkyl group. Examples include $C_1$-$C_6$-alkylcarbonyl such as $CO$—$CH_3$, $CO$—$C_2H_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl and the like.

The term "($C_1$-$C_6$-alkoxy)carbonyl" as used herein refers to a straight-chain or branched alkoxy group (as mentioned above) having 1 to 6 carbon atoms attached via the carbon atom of the carbonyl group, for example $CO$—$OCH_3$, $CO$—$OC_2H_5$, $CO$—$OCH_2$—$C_2H_5$, $CO$—$OCH(CH_3)_2$, n-butoxycarbonyl, $CO$—$OCH(CH_3)$—$C_2H_5$, $CO$—$OCH_2$—$CH(CH_3)_2$, $CO$—$OC(CH_3)_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl.

The term "($C_1$-$C_6$-alkyl)carbonyloxy" as used herein refers to a straight-chain or branched saturated alkyl group having 1 to 6 carbon atoms (as mentioned above) bonded via the carbon atom of the carbonyloxy group at any bond in the alkyl group, for example O—CO—$CH_3$, O—CO—$C_2H_5$, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy or 1,2-dimethylpropylcarbonyloxy.

The term "$C_1$-$C_6$-alkylthio "($C_1$-$C_6$-alkylsulfanyl: $C_1$-$C_6$-alkyl-S—)" as used herein refers to a straight-chain or branched saturated alkyl group having 1 to 6 carbon atoms (as mentioned above) which is attached via a sulfur atom, for example $C_1$-$C_4$-alkylthio such as methylthio, ethylthio, propylthio, 1-methylethylthio, butylthio, 1-methylpropylthio, 2-methylpropylthio, 1,1-dimethylethylthio, n-pentylthiocarbonyl, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylhio, 2,2-dimethylbutylthio, 2,3-dimethylbutylthio, 3,3-dimethylbutylthio, 1-ethylbutlthio, 2-ethylbutylthio, 1,1,2-trimethylpropylthio, 1,2,2-trimethylpropylthio, 1-ethyl-1-methylpropylthio or 1-ethyl-2-methylpropylthio.

The term "($C_1$-$C_6$-alkylthio)carbonyl" as used herein refers to a straight-chain or branched alkthio group (as mentioned above) having 1 to 6 carbon atoms attached via the carbon atom of the carbonyl group. Examples include CO—$SCH_3$, CO—$SC_2H_5$, CO—$SCH_2$—$C_2H_5$, CO—SCH$(CH_3)_2$, n-butylthiocarbonyl, CO—SCH$(CH_3)$—$C_2H_5$, CO—$SCH_2$—CH$(CH_3)_2$, CO—SC$(CH_3)_3$, n-pentylthiocarbonyl, 1-methylbutylthiocarbonyl, 2-methylbutylthiocarbonyl, 3-methylbutylthiocarbonyl, 2,2-dimethylpropylthiocarbonyl, 1-ethylpropylthiocarbonyl, n-hexylthiocarbonyl, 1,1-dimethylpropylthiocarbonyl, 1,2-dimethylpropylthiocarbonyl, 1-methylpentylthiocarbonyl, 2-methylpentylthiocarbonyl, 3-methylpentylthiocarbonyl, 4-methylpentylthiocarbonyl, 1,1-dimethylbutylthiocarbonyl, 1,2-dimethylbutylthiocarbonyl, 1,3-dimethylbutylhiocarbonyl, 2,2-dimethylbutylthiocarbonyl, 2,3-dimethylbutylthiocarbonyl, 3,3-dimethyl butylthiocarbonyl, 1-ethylbutlthioycarbonyl, 2-ethylbutylthiocarbonyl, 1,1,2-trimethylpropylthiocarbonyl, 1,2,2-trimethylpropylthiocarbonyl, 1-ethyl-1-methylpropylthiocarbonyl or 1-ethyl-2-methylpropylthiocarbonyl.

The term "$C_1$-$C_6$-alkylsulfinyl" ($C_1$-$C_6$-alkylsulfoxyl: $C_1$-$C_6$-alkyl-S(═O)—), as used herein refers to a straight-chain or branched saturated alkyl group (as mentioned above) having 1 to 6 carbon atoms bonded through the sulfur atom of the sulfinyl group at any position in the alkyl group, for example SO—$CH_3$, SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "$C_1$-$C_6$-alkylamino" refers to a secondary amino group carrying one alkyl group as defined above, e.g. methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino.

The term "di($C_1$-$C_6$-alkyl)amino)" refers to a tertiary amino group carrying two alkyl radicals as defined above, e.g. dimethylamino, diethylamino, di-n-propylamino, diisopropylamino, N-ethyl-N-methylamino, N-(n-propyl)-N-methylamino, N-(isopropyl)-N-methylamino, N-(n-butyl)-N-methylamino, N-(n-pentyl)-N-methylamino, N-(2-butyl)-N-methylamino, N-(isobutyl)-N-methylamino, N-(n-pentyl)-N-methylamino, N-(n-propyl)-N-ethylamino, N-(isopropyl)-N-ethylamino, N-(n-butyl)-N-ethylamino, N-(n-pentyl)-N-ethylamino, N-(2-butyl)-N-ethylamino, N-(isobutyl)-N-ethylamino or N-(n-pentyl)-N-ethylamino.

The term "$C_1$-$C_6$-alkylsulfonyl" ($C_1$-$C_6$-alkyl-S(═O)$_2$—) as used herein refers to a straight-chain or branched saturated alkyl group having 1 to 6 carbon atoms (as mentioned above) which is bonded via the sulfur atom of the sulfonyl group at any position in the alkyl group, for example $SO_2$—$CH_3$, $SO_2$—$C_2H_5$, n-propylsulfonyl, $SO_2$—CH$(CH_3)_2$, n-butylsulfonyl, 1-methylpropylsulfonyl, 2-methylpropylsulfonyl, $SO_2$—C$(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "$C_2$-$C_6$-alkenyl" as used herein and in the alkenyl moieties of $C_2$-$C_6$-alkenyloxy, $C_2$-$C_6$-alkenylamino, $C_2$-$C_6$-alkenylthio, $C_2$-$C_6$-alkenylsulfonyl, ($C_2$-$C_6$-alkenyl)carbonyl, ($C_2$-$C_6$-alkenyloxy)carbonyl and ($C_2$-$C_6$-alkenyl)carbonyloxy refers to a straight-chain or branched unsaturated hydrocarbon group having 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term, "$C_2$-$C_6$-alkenyloxy" as used herein refers to a straight-chain or branched alkenyl group having 2 to 6 carbon atoms (as mentioned above) which is attached via an oxygen atom, such as vinyloxy, allyloxy (propen-3-yloxy), methallyloxy, buten-4-yloxy, etc.

The term "$C_2$-$C_6$-alkenylthio" as used herein refers to a straight-chain or branched alkenyl group having 2 to 6 carbon atoms (as mentioned above) which is attached via a sulfur atom, for example vinylsulfanyl, allylsulfanyl (propen-3-ylthio), methallylsufanyl, buten-4-ylsulfanyl, etc.

The term "$C_2$-$C_6$-alkenylamino" as used herein refers to a straight-chain or branched alkenyl group having 2 to 6 carbon atoms (as mentioned above) which is attached via the nitrogen atom of the amino group, for example vinylamino, allylamino (propen-3-ylamino), methallylamino, buten-4-ylamino, etc.

The term "$C_2$-$C_6$-alkenylsulfonyl" as used herein refers to a straight-chain or branched alkenyl group having 2 to 6 carbon atoms (as mentioned above) which is attached via a sulfonyl ($SO_2$) group, for example vinylsulfonyl, allylsulfonyl (propen-3-ylsulfonyl), methallylsulfonyl, buten-4-ylsulfonyl, etc.

The term "$C_2$-$C_6$-alkynyl" as used herein and in the alkynyl moieties of $C_2$-$C_6$-alkynyloxy, $C_2$-$C_6$-alkynylamino, $C_2$-$C_6$-alkynylthio, $C_2$-$C_6$-alkynylsulfonyl, $C_2$-$C_6$-alkynylcarbonyl, $C_2$-$C_6$-alkynyloxycarbonyl and $C_1$-$C_6$-alkynylcarbonyloxy refers to a straight-chain or branched unsaturated hydrocarbon group having 2 to 6 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term, "$C_2$-$C_6$-alkynyloxy" as used herein refers to a straight-chain or branched alkynyl group having 2 to 6 carbon atoms (as mentioned above) which is attached via an oxygen atom, such as propargyloxy (propyn-3-yloxy), butyn-3-yloxy, and butyn-4-yloxy.

The term "$C_2$-$C_6$-alkynylthio" as used herein refers to a straight-chain or branched alkynyl group having 2 to 6 carbon atoms (as mentioned above) which is attached via a sulfur atom, such as propargylsulfanyl (propyn-3-ylthio), butyn-3-ylsufanyl and butyn-4-ylsulfanyl.

The term "$C_2$-$C_6$-alkynylamino" as used herein refers to a straight-chain or branched alkynyl group having 2 to 6 carbon atoms (as mentioned above) which is attached via the nitrogen atom of an amino group, such as propargylamino (propyn-3-ylamino), butyn-3-amino, and butyn-4-ylamino.

The term "$C_2$-$C_6$-alkynylsulfonyl" as used herein refers to a straight-chain or branched alkynyl group having 2 to 6 carbon atoms (as mentioned above) which is attached via a sulfonyl ($SO_2$) group, such as propargylsulfonyl (propin-3-yltsulfonyl), butin-3-ylsulfonyl and butin-4-ylsulfonyl.

The term "$C_3$-$C_8$-cycloalkyl" as used herein refers to a mono- or bi- or polycyclic hydrocarbon radical having 3 to 8 carbon atoms, in particular 3 to 6 carbon atoms. Examples of monocyclic radicals comprise cyclopropyl, cyclobutyl, cyclopentyl, cyclohexyl, cycloheptyl, cyclooctyl, cyclononyl and cyclodecyl. Examples of bicyclic radicals comprise bicyclo[2.2.1]heptyl, bicyclo[3.1.1]heptyl, bicyclo[2.2.2]octyl and bicyclo[3.2.1]octyl.

The term "5- or 6-membered heteroaromatic ring" as used herein refers to a monocyclic heteroaromatic radical which has 5 or 6 ring members, which may comprise a fused 5, 6 or 7 membered ring thus having a total number of ring members from 8 to 10, wherein in each case 1, 2, 3 or 4 of these ring members are heteroatoms selected, independently from each other, from the group consisting of oxygen, nitrogen and sulfur. The heterocyclic radical may be attached to the remainder of the molecule via a carbon ring member or via a nitrogen ring member. The fused ring comprises $C_5$-$C_7$-cycloalkyl, $C_5$-$C_7$-cycloalkenyl, or 5 to 7 membered heterocyclyl and phenyl.

Examples for monocyclic 5- to 6-membered heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl and isoxazolyl.

Examples for 5- to 6-membered heteroaromatic rings carrying a fused phenyl ring are quinolinyl, isoquinolinyl, indolyl, indolizinyl, isoindolyl, indazolyl, benzofuryl, benzthienyl, benzo[b]thiazolyl, benzoxazolyl, benzthiazolyl, benzoxazolyl, and benzimidazolyl. Examples for 5- to 6-membered heteroaromatic rings carrying a fused cycloalkenyl ring are dihydroindolyl, dihydroindolizinyl, dihydroisoindolyl, dihydrochinolinyl, dihydroisochinolinyl, chromenyl, chromanyl and the like.

The term "mono- or bicyclic 5- to 10-membered heterocyclyl" comprises monocyclic and bicyclic heteroaromatic rings as defined above and monocyclic and bicyclix non-aromatic saturated or partially unsaturated heterocyclic rings having 5, 6, 7, 8, 9 or 10 ring members. Examples for non-aromatic rings include pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, dioxanyl, thiopyranyl, dihydrothiopyranyl, tetrahydrothiopyranyl, morpholinyl, thiazinyl and the like.

The term "5-, 6- or 7-membered carbocycle" comprises monocyclic aromatic rings and nonaromatic saturated or partially unsaturated carbocyclic rings having 5, 6 or 7 ring members. Examples for non-aromatic rings include cyclopentyl, cyclopentenyl, cyclopentadienyl, cyclohexyl, cyclohexenyl, cyclohexadienyl, cycloheptyl, cycloheptenyl, cycloheptadienyl and the like.

As regards the pesticidal activity of the compounds of general formula I, preference is given to those compounds of the formula I, wherein the variables n, m, X, $R^1$, $R^2$, $R^3$, $R^{4a}$, $R^{4b}$, $R^{4c}$, $R^{4d}$, $R^5$, $R^6$, $R^7$, $R^8$, $R^9$, $R^{10}$, $R^c$, Ar and Het have independently of each other or more preferably in combination the following meanings.

Preferred are compounds of the formula I, wherein $R^1$, $R^2$, $R^3$ are, independently of each other, selected from hydrogen, $C_1$-$C_6$-alkyl, $C_1$-$C_6$-haloalkyl, $C_3$-$C_6$-cycloalkyl and $C_3$-$C_6$-halocycloalkyl, wherein 1, 2 or 3 hydrogen atoms in the aforementioned aliphatic radicals may be replaced, independently of one another, by a radical selected from the group consisting of cyano, nitro, hydroxy, mercapto, amino, carboxyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, and wherein $C_3$-$C_6$-cycloalkyl and $C_3$-$C_6$-halocycloalkyl may also carry 1, 2, 3, 4 or 5 radicals selected from $C_1$-$C_6$-alkyl and $C_1$-$C_6$-haloalkyl.

More preferred are compounds of the formula I, wherein $R^1$, $R^2$ and $R^3$ are, independently of each other, selected from hydrogen and $C_1$-$C_6$-alkyl, especially methyl, ethyl, n-propyl, iso-propyl, n-butyl and isobutyl.

Most preferred are compounds of the formula I, wherein $R^1$, $R^2$ and $R^3$ are hydrogen.

Preference is also given to compounds of the formula I wherein $R^{4a}$, $R^{4b}$, $R^{4c}$ and $R^{4d}$ are, independently of each other, selected from hydrogen, halogen, $C_1$-$C_6$-alkyl, especially methyl or ethyl, and $C_1$-$C_6$-haloalkyl. More preference is given to compounds of the formula I wherein $R^{4a}$, $R^{4b}$, $R^{4c}$ and $R^{4d}$ are selected from hydrogen. Likewise, preference is given to compounds I, wherein one of the radicals $R^{4a}$, $R^{4b}$, $R^{4c}$ or $R^{4d}$ is selected from halogen, $C_1$-$C_6$-alkyl, especially methyl or ethyl, and $C_1$-$C_6$-haloalkyl and the other radicals $R^{4a}$, $R^{4b}$, $R^{4c}$ or $R^{4d}$ are hydrogen.

Preference is furthermore given to compounds of the formula I in which $R^5$, $R^6$ are, independently of each other, selected from hydrogen, cyano, nitro, C(=O)$R^c$, wherein $R^c$ is as defined above, $C_1$-$C_6$-alkyl, $C_2$-$C_6$-alkenyl, $C_2$-$C_6$-alkynyl, $C_3$-$C_8$-cycloalkyl, ($C_1$-$C_6$-alkoxy)methylen, $C_1$-$C_6$-alkylsulfanyl, $C_1$-$C_6$-alkylsulfinyl and $C_1$-$C_6$-alkylsulfonyl, wherein the aliphatic moieties in the aforementioned radicals may be unsubstituted, partially or completely halogenated and/or may carry 1, 2 or 3 radicals, which are independently of one another, selected from the group consisting of cyano, nitro, hydroxy, mercapto, amino, carboxyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio and wherein $C_3$-$C_8$-cycloalkyl may also carry 1, 2, 3, 4 or 5 radicals selected from $C_1$-$C_6$-alkyl and $C_1$-$C_6$-haloalkyl. Amongst these, particular preference is given to those compounds I in which wherein $R^5$, $R^6$ are, independently of each other, selected from hydrogen, cyano, nitro, $C_1$-$C_6$-alkyl and C(=O)$R^c$, wherein $R^c$ is as defined above.

If present, $R^c$ is preferably hydrogen, $C_1$-$C_6$ alkyl, $C_2$-$C_6$-alkenyl, $C_2$-$C_6$-alkynyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)-amino, hydrazino, ($C_1$-$C_6$-alkyl)hydrazino, di($C_1$-$C_6$-alkyl)hydrazino, phenyl or a mono- or bicyclic 5- to 10-membered heteroaromatic ring, which contains 1, 2, 3 or 4 heteroatoms selected from O, S and N.

Preference is given to compounds I wherein X is sulfur.

Likewise, preference is given to compounds I wherein X is oxygen.

Likewise, preference is also given to compounds I in which X is $NR^7$ wherein $R^7$ is as defined above.

$R^7$ is preferably hydrogen, cyano, nitro, C(=O)—$R^c$, especially formyl, $C_1$-$C_6$-alkylcarbonyl or benzoyl, $C_1$-$C_6$-alkyl, $C_2$-$C_6$-alkenyl, $C_2$-$C_6$-alkynyl, $C_3$-$C_8$-cycloalkyl, ($C_1$-$C_6$-alkoxy)methylen, $C_1$-$C_6$-alkylsulfanyl, $C_1$-$C_6$-alkylsulfinyl or $C_1$-$C_6$-alkylsulfonyl, wherein the aliphatic moieties in the aforementioned radicals may be unsubstituted, partially or completely halogenated and/or may carry 1, 2 or 3 radicals, which are independently of one another, selected from the group consisting of cyano, nitro, hydroxy, mercapto, amino, carboxyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio and wherein $C_3$-$C_8$-cycloalkyl may also carry 1, 2, 3, 4 or 5 radicals selected from $C_1$-$C_6$-alkyl and $C_1$-$C_6$-haloalkyl.

$R^7$ is in particular selected from hydrogen, cyano, nitro, C(=O)$R^c$, especially benzoyl, formyl or $C_1$-$C_6$-alkylcarbonyl such as acetyl or ethylcarbonyl, $C_1$-$C_6$-alkyl, especially methyl, ethyl, n-propyl, isopropyl, n-butyl, isobutyl, n-pentyl, n-hexyl, with hydrogen, $C_1$-$C_6$-alkyl or a radical C(=O)$R^c$ wherein $R^c$ is H, $C_1$-$C_6$-alkyl or phenyl, being most preferred.

Preference is given to compounds I wherein the carbon atom which carries the radical A has S-configuration.

Preference is also given to compounds I wherein the carbon atom which carries the radical A has R-configuration.

A preferred embodiment of the invention relates to compounds of the formula I in which at least one of the integers m or n is different from 0. If present, $R^{10}$ is preferably selected from halogen, OH, SH, $NH_2$, $SO_3H$, COOH, cyano, $CONH_2$, C(=O)$R^c$, wherein $R^c$ is as defined above, $C_1$-$C_6$-alkyl, $C_3$-$C_8$-cycloalkyl, $C_1$-$C_6$-alkylamino, di($C_1$-$C_6$-alkyl)-amino, wherein the aliphatic moieties in the aforementioned radicals may be unsubstituted, partially or completely halogenated and/or may carry 1, 2 or 3 radicals, which are independently of one another, selected from the group consisting of cyano, nitro, hydroxy, mercapto, amino, carboxyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio and wherein $C_3$-$C_8$-cycloalkyl may also carry 1, 2, 3, 4 or 5 radicals selected from $C_1$-$C_6$-alkyl and $C_1$-$C_6$-haloalkyl.

More preferably, $R^{10}$ is selected from halogen, $C_1$-$C_6$-alkyl, and $C_1$-$C_6$-alkoxy, wherein the two last-mentioned radicals may be unsubstituted or partially or fully halogenated. Particularly preferred radicals $R^{10}$ include fluorine, chlorine, bromine, $C_1$-$C_4$-alkyl, in particular methyl, ethyl, n-propyl, isopropyl, n-butyl or isobutyl, $C_1$-$C_4$-haloalkyl, in particular $C_1$-$C_2$-fluoroalkyl such as difluoromethyl, trifluoromethyl and 2,2,2-trifluoroethyl, $C_1$-$C_4$-alkoxy such as methoxy or ethoxy, and $C_1$-$C_4$-haloalkoxy, especially $C_1$-$C_2$-fluoroalkoxy such as difluoromethoxy or trifluoromethoxy.

A preferred embodiment of the invention relates to compounds of the formula I wherein n is 1, 2 or 3, in particular 1 or 2. In particular Ar is phenyl carrying 1, 2 or 3 radicals $R^{10}$, wherein one radical $R^{10}$ is located in the 3-position relative to the point of attachment to the ethane skeleton. Amongst these, preference is given to compounds of the formula I, wherein Ar is phenyl, which carries one radical $R^{10}$ which is located in the 3-position of the phenyl ring. Preference is also given to compounds of the formula I wherein Ar is phenyl, which carries 2 or 3 radicals $R^{10}$, wherein one radical $R^{10}$ is located in the 3-position and an other radical $R^{10}$ is located in the 5-position of the phenyl ring. Amongst the compounds wherein Ar is phenyl, which carries 3 radicals $R^{10}$, preference is given to those, wherein one radical $R^{10}$ is located in the 3-position, a second radical $R^{10}$ is located in the 5-position and the third radical $R^{10}$ is located in the 4-position of the phenyl ring.

A preferred embodiment of the invention relates to compounds of the formula I wherein Ar is phenyl which may be unsubstituted or substituted by n radicals $R^{10}$ wherein n and $R^{10}$ have the meanings as defined above, in particular the meanings given as being preferred.

Examples of preferred radicals Ar are listed in table A below.

TABLE A

| | Ar |
|---|---|
| Ar-1 | phenyl |
| Ar-2 | 3-fluorophenyl |
| Ar-3 | 3-bromophenyl |
| Ar-4 | 3-chlorophenyl |
| Ar-5 | 3-methylphenyl |
| Ar-6 | 3-ethylphenyl |
| Ar-7 | 3-methoxyphenyl |
| Ar-8 | 3-trifluoromethylphenyl |
| Ar-9 | 3,5-difluorophenyl |
| Ar-10 | 3,5-dibromophenyl |
| Ar-11 | 3,5-dichlorophenyl |
| Ar-12 | 3,5-dimethylphenyl |
| Ar-13 | 3,5-diethylphenyl |
| Ar-14 | 3,5-dimethoxyphenyl |
| Ar-15 | 3,5-di-trifluoromethylphenyl |
| Ar-16 | 3-fluoro-5-chlorophenyl |
| Ar-17 | 3-fluoro-5-bromophenyl |
| Ar-18 | 3-fluoro-5-methylphenyl |
| Ar-19 | 3-fluoro-5-ethylphenyl |
| Ar-20 | 3-fluoro-5-methoxyphenyl |
| Ar-21 | 3-fluoro-5-trifluoromethylphenyl |
| Ar-22 | 3-chloro-5-bromophenyl |
| Ar-23 | 3-chloro-5-methylphenyl |
| Ar-24 | 3-chloro-5-ethylphenyl |
| Ar-25 | 3-chloro-5-methoxyphenyl |
| Ar-26 | 3-chloro-5-trifluoromethylphenyl |
| Ar-27 | 3-bromo-5-methylphenyl |
| Ar-28 | 3-bromo-5-ethylphenyl |
| Ar-29 | 3-bromo-5-methoxyphenyl |
| Ar-30 | 3-bromo-5-trifluoromethylphenyl |
| Ar-31 | 3-methyl-5-ethylphenyl |
| Ar-32 | 3-methyl-5-methoxyphenyl |
| Ar-33 | 3-methyl-5-trifluoromethylphenyl |
| Ar-34 | 3-ethyl-5-methoxyphenyl |
| Ar-35 | 3-ethyl-5-trifluoromethylphenyl |
| Ar-36 | 3-methoxy-5-trifluoromethylphenyl |
| Ar-37 | 3,4,5-trifluorophenyl |
| Ar-38 | 3,4,5-tribromophenyl |
| Ar-39 | 3,4,5-trichlorophenyl |
| Ar-40 | 3,4,5-trimethylphenyl |
| Ar-41 | 3,4,5-triethylphenyl |
| Ar-42 | 3,4,5-trimethoxyphenyl |
| Ar-43 | 3,4,5-tri-trifluoromethylphenyl |
| Ar-44 | 3,4-difluoro-5-chlorophenyl |
| Ar-45 | 3,4-difluoro-5-bromophenyl |
| Ar-46 | 3,4-difluoro-5-methylphenyl |
| Ar-47 | 3,4-difluoro-5-ethylphenyl |
| Ar-48 | 3,4-difluoro-5-methoxyphenyl |
| Ar-49 | 3,4-difluoro-5-trifluoromethylphenyl |
| Ar-50 | 3,5-difluoro-4-chlorophenyl |
| Ar-51 | 3,5-difluoro-4-bromophenyl |
| Ar-52 | 3,5-difluoro-4-methylphenyl |
| Ar-53 | 3,5-difluoro-4-ethylphenyl |
| Ar-54 | 3,5-difluoro-4-methoxyphenyl |
| Ar-55 | 3,5-difluoro-4-trifluoromethylphenyl |
| Ar-56 | 3-fluoro-4,5-dichlorophenyl |
| Ar-57 | 3-fluoro-4-chloro-5-bromophenyl |
| Ar-58 | 3-fluoro-4-chloro-5-methylphenyl |
| Ar-59 | 3-fluoro-4-chloro-5-ethylphenyl |
| Ar-60 | 3-fluoro-4-chloro-5-methoxyphenyl |
| Ar-61 | 3-fluoro-4-chloro-5-trifluoromethylphenyl |
| Ar-62 | 3-fluoro-4-bromo-5-chlorophenyl |
| Ar-63 | 3-fluoro-4,5-dibromophenyl |
| Ar-64 | 3-fluoro-4-bromo-5-methylphenyl |
| Ar-65 | 3-fluoro-4-bromo-5-ethylphenyl |
| Ar-66 | 3-fluoro-4-bromo-5-methoxyphenyl |
| Ar-67 | 3-fluoro-4-bromo-5-trifluoromethylphenyl |
| Ar-68 | 3-fluoro-4-methyl-5-chlorophenyl |
| Ar-69 | 3-fluoro-4-methyl-5-bromophenyl |
| Ar-70 | 3-fluoro-4,5-dimethylphenyl |
| Ar-71 | 3-fluoro-4-methyl-5-ethylphenyl |
| Ar-72 | 3-fluoro-4-methyl-5-methoxyphenyl |
| Ar-73 | 3-fluoro-4-methyl-5-trifluoromethylphenyl |
| Ar-74 | 3-fluoro-4-ethyl-5-chlorophenyl |
| Ar-75 | 3-fluoro-4-ethyl-5-bromophenyl |
| Ar-76 | 3-fluoro-4-ethyl-5-methylphenyl |
| Ar-77 | 3-fluoro-4,5-diethylphenyl |
| Ar-78 | 3-fluoro-4-ethyl-5-methoxyphenyl |
| Ar-79 | 3-fluoro-4-ethyl-5-trifluoromethylphenyl |
| Ar-80 | 3-fluoro-4-methoxy-5-chlorophenyl |
| Ar-81 | 3-fluoro-4-methoxy-5-bromophenyl |
| Ar-82 | 3-fluoro-4-methoxy-5-methylphenyl |
| Ar-83 | 3-fluoro-4-methoxy-5-ethylphenyl |
| Ar-84 | 3-fluoro-4,5-dimethoxyphenyl |
| Ar-85 | 3-fluoro-4-methoxy-5-trifluoromethylphenyl |
| Ar-86 | 3-fluoro-4-trifluoromethyl-5-chlorophenyl |
| Ar-87 | 3-fluoro-4-trifluoromethyl-5-bromophenyl |
| Ar-88 | 3-fluoro-4-trifluoromethyl-5-methylphenyl |
| Ar-89 | 3-fluoro-4-trifluoromethyl-5-ethylphenyl |
| Ar-90 | 3-fluoro-4-trifluoromethyl-5-methoxyphenyl |
| Ar-91 | 3-fluoro-4,5-di-trifluoromethylphenyl |
| Ar-92 | 3,4-dichloro-5-bromophenyl |
| Ar-93 | 3,4-dichloro-5-methylphenyl |
| Ar-94 | 3,4-dichloro-5-ethylphenyl |
| Ar-95 | 3,4-dichloro-5-methoxyphenyl |
| Ar-96 | 3,4-dichloro-5-trifluoromethylphenyl |
| Ar-97 | 3,5-dichloro-4-bromophenyl |
| Ar-98 | 3,5-dichloro-4-methylphenyl |
| Ar-99 | 3,5-dichloro-4-ethylphenyl |
| Ar-100 | 3,5-dichloro-4-methoxyphenyl |
| Ar-101 | 3,5-dichloro-4-trifluoromethylphenyl |
| Ar-102 | 3-chloro-4,5-dibromophenyl |
| Ar-103 | 3-chloro-4-bromo-5-methylphenyl |
| Ar-104 | 3-chloro-4-bromo-5-ethylphenyl |
| Ar-105 | 3-chloro-4-bromo-5-methoxyphenyl |
| Ar-106 | 3-chloro-4-bromo-5-trifluoromethylphenyl |
| Ar-107 | 3-chloro-4-methyl-5-bromophenyl |
| Ar-108 | 3-chloro-4,5-dimethylphenyl |
| Ar-109 | 3-chloro-4-methyl-5-ethylphenyl |
| Ar-110 | 3-chloro-4-methyl-5-methoxyphenyl |
| Ar-111 | 3-chloro-4-methyl-5-trifluoromethylphenyl |
| Ar-112 | 3-chloro-4-ethyl-5-bromophenyl |
| Ar-113 | 3-chloro-4-ethyl-5-methylphenyl |
| Ar-114 | 3-chloro-4,5-diethylphenyl |
| Ar-115 | 3-chloro-4-ethyl-5-methoxyphenyl |
| Ar-116 | 3-chloro-4-ethyl-5-trifluoromethylphenyl |
| Ar-117 | 3-chloro-4-methoxy-5-bromophenyl |
| Ar-118 | 3-chloro-4-methoxy-5-methylphenyl |
| Ar-119 | 3-chloro-4-methoxy-5-ethylphenyl |
| Ar-120 | 3-chloro-4,5-dimethoxyphenyl |
| Ar-121 | 3-chloro-4-methoxy-5-trifluoromethylphenyl |
| Ar-122 | 3-chloro-4-trifluoromethyl-5-bromophenyl |
| Ar-123 | 3-chloro-4-trifluoromethyl-5-methylphenyl |
| Ar-124 | 3-chloro-4-trifluoromethyl-5-ethylphenyl |
| Ar-125 | 3-chloro-4-trifluoromethyl-5-methoxyphenyl |
| Ar-126 | 3-chloro-4,5-di-trifluoromethylphenyl |
| Ar-127 | 3,4-dibromo-5-methylphenyl |
| Ar-128 | 3,4-dibromo-5-ethylphenyl |
| Ar-129 | 3,4-dibromo-5-methoxyphenyl |
| Ar-130 | 3,4-dibromo-5-trifluoromethylphenyl |
| Ar-131 | 3,5-dibromo-4-methylphenyl |
| Ar-132 | 3,5-dibromo-4-ethylphenyl |
| Ar-133 | 3,5-dibromo-4-methoxyphenyl |
| Ar-134 | 3,5-dibromo-4-trifluoromethylphenyl |
| Ar-135 | 3-bromo-4,5-dimethylphenyl |
| Ar-136 | 3-bromo-4-methyl-5-ethylphenyl |
| Ar-137 | 3-bromo-4-methyl-5-methoxyphenyl |
| Ar-138 | 3-bromo-4-methyl-5-trifluoromethylphenyl |
| Ar-139 | 3-bromo-4-ethyl-5-methylphenyl |
| Ar-140 | 3-bromo-4,5-diethylphenyl |
| Ar-141 | 3-bromo-4-ethyl-5-methoxyphenyl |
| Ar-142 | 3-bromo-4-ethyl-5-trifluoromethylphenyl |
| Ar-143 | 3-bromo-4-methoxy-5-methylphenyl |
| Ar-144 | 3-bromo-4-methoxy-5-ethylphenyl |
| Ar-145 | 3-bromo-4,5-dimethoxyphenyl |
| Ar-146 | 3-bromo-4-methoxy-5-trifluoromethylphenyl |
| Ar-147 | 3-bromo-4-trifluoromethyl-5-methylphenyl |
| Ar-148 | 3-bromo-4-trifluoromethyl-5-ethylphenyl |
| Ar-149 | 3-bromo-4-trifluoromethyl-5-methoxyphenyl |
| Ar-150 | 3-bromo-4,5-di-trifluoromethylphenyl |

TABLE A-continued

| | Ar |
|---|---|
| Ar-151 | 3,4-dimethyl-5-ethylphenyl |
| Ar-152 | 3,4-dimethyl-5-methoxyphenyl |
| Ar-153 | 3,4-dimethyl-5-trifluoromethylphenyl |
| Ar-154 | 3,5-dimethyl-4-ethylphenyl |
| Ar-155 | 3,5-dimethyl-4-methoxyphenyl |
| Ar-156 | 3,5-dimethyl-4-trifluoromethylphenyl |
| Ar-157 | 3-methyl-4-ethyl-5-methoxyphenyl |
| Ar-158 | 3-methyl-4-ethyl-5-trifluoromethylphenyl |
| Ar-159 | 3-methyl-4-methoxy-5-ethylphenyl |
| Ar-160 | 3-methyl-4-methoxy-5-trifluoromethylphenyl |
| Ar-161 | 3-methyl-4-trifluoromethyl-5-ethylphenyl |
| Ar-162 | 3-methyl-4-trifluoromethyl-5-methoxyphenyl |
| Ar-163 | 3-methyl-4,5-di-trifluoromethylphenyl |
| Ar-164 | 3,4-diethyl-5-methoxyphenyl |
| Ar-165 | 3,4-diethyl-5-trifluoromethylphenyl |
| Ar-166 | 3,5-diethyl-4-methoxyphenyl |
| Ar-167 | 3,5-diethyl-4-trifluoromethylphenyl |
| Ar-168 | 3-ethyl-4-methoxy-5-trifluoromethylphenyl |
| Ar-169 | 3-ethyl-4,5-dimethoxyphenyl |
| Ar-170 | 3,4-di-trifluoromethyl-5-methoxyphenyl |
| Ar-171 | 3,5-di-trifluoromethyl-4-methoxyphenyl |
| Ar-172 | 3,5-dichloro-4-fluorophenyl |
| Ar-173 | 3-chloro-4-fluoro-5-methylphenyl |
| Ar-174 | 3-chloro-4-fluoro-5-methoxyphenyl |
| Ar-175 | 3-chloro-4-fluoro-5-trifluoromethylphenyl |
| Ar-176 | 3-bromo-4-fluoro-5-methylphenyl |
| Ar-177 | 3-bromo-4-fluoro-5-methoxyphenyl |
| Ar-178 | 3-bromo-4-fluoro-5-trifluoromethylphenyl |
| Ar-179 | 3,5-dimethyl-4-fluorophenyl |
| Ar-180 | 3-methyl-4-fluoro-5-methoxyphenyl |
| Ar-181 | 3-methyl-4-fluoro-5-trifluoromethylphenyl |
| Ar-182 | 3,5-dimethoxy-4-fluorophenyl |
| Ar-183 | 3-methoxy-4-fluoro-5-trifluoromethylphenyl |
| Ar-184 | 3,5-ditrifluoromethyl-4-fluorophenyl |
| Ar-185 | 3-bromo-4-chloro-5-methylphenyl |
| Ar-186 | 3-bromo-4-chloro-5-methoxyphenyl |
| Ar-187 | 3-bromo-4-chloro-5-trifluoromethylphenyl |
| Ar-188 | 3,5-dimethyl-4-chlorophenyl |
| Ar-189 | 3-methyl-4-chloro-5-methoxyphenyl |
| Ar-190 | 3-methyl-4-chloro-5-trifluoromethylphenyl |
| Ar-191 | 3,5-dimethoxy-4-chlorophenyl |
| Ar-192 | 3-methoxy-4-chloro-5-trifluoromethylphenyl |
| Ar-193 | 3,5-ditrifluoromethyl-4-chlorophenyl |
| Ar-194 | 3,5-dimethyl-4-bromophenyl |
| Ar-195 | 3-methyl-4-bromo-5-methoxyphenyl |
| Ar-196 | 3-methyl-4-bromo-5-trifluoromethylphenyl |
| Ar-197 | 3-methoxy-4-bromo-5-trifluoromethylphenyl |
| Ar-198 | 3,5-ditrifluoromethyl-4-bromophenyl |
| Ar-199 | 3,5-dimethoxy-4-methylphenyl |
| Ar-200 | 3-methoxy-4-methyl-5-trifluoromethylphenyl |
| Ar-201 | 3,5-ditrifluoromethyl-4-methylphenyl |
| Ar-202 | 3-methoxy-4-ethyl-5-trifluoromethylphenyl |
| Ar-203 | 3-methyl-4,5-dimethoxyphenyl |
| Ar-204 | 3,4-dimethoxy-5-trifluoromethylphenyl |
| Ar-205 | 3,5-dimethoxy-4-trifluoromethylphenyl |

Het is preferably a C-bound 5- or 6-membered, in particular a 5-membered C-bound heteroaromatic ring as defined above which is unsubstituted or substituted by m radicals $R^8$ and/or may carry at its nitrogen atom, if present, a radical $R^9$ or oxygen, with m being 0, 1, 2 or 3, in particular 0, 1 or 2.

If present, $R^8$ is preferably selected from halogen, OH, SH, $NH_2$, $SO_3H$, COOH, cyano, $CONH_2$, $C(=O)R^c$, $C_1$-$C_6$-alkyl, $C_3$-$C_8$-cycloalkyl, $C_1$-$C_6$-alkylamino, di($C_1$-$C_6$-alkyl)amino, wherein the aliphatic moieties in the aforementioned radicals may be unsubstituted, partially or completely halogenated and/or may carry 1, 2 or 3 radicals, which are independently of one another, selected from the group consisting of cyano, nitro, hydroxy, mercapto, amino, carboxyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio and wherein $C_3$-$C_8$-cycloalkyl may also carry 1, 2, 3, 4 or 5 radicals selected from $C_1$-$C_6$-alkyl and $C_1$-$C_6$-haloalkyl. More preferably, $R^8$ is selected from halogen, especially chlorine, $C_1$-$C_6$-alkyl, in particular $C_1$-$C_4$-alkyl, such as methyl, ethyl, n-propyl, isopropyl, n-butyl, isobutyl or tertbutyl, $C_1$-$C_6$-haloalkyl, in particular $C_1$-$C_4$-haloalkyl, especially $C_1$-$C_2$-fluoroalkyl such as trifluoromethyl, difluoromethyl or 2,2,2-trifluoroethyl, $C_1$-$C_6$-alkoxy, especially methoxy, ethoxy or propoxy, and $C_1$-$C_6$-haloalkoxy, especially $C_1$-$C_2$-fluoroalkyl such as trifluoromethoxy or difluoromethoxy.

If present, $R^9$ is preferably hydrogen or $C_1$-$C_6$-alkyl, such as methyl, ethyl, n-propyl, isopropyl, n-butyl, isobutyl or tert.-butyl, more preferably hydrogen or $C_1$-$C_4$-alkyl, in particular hydrogen, methyl or ethyl.

In particular, Het is unsubstituted or carries 1 or 2 radicals $R^8$. Likewise preference is given to compounds I, wherein Het is unsubstituted or substituted by 1 or 2 radicals $R^8$ and 1 radical $R^9$.

Preference is given to compounds I wherein Het is a 5-membered heteroaromatic ring, in particular a 5-membered, C-bound heteroaromatic ring, as defined above, with Het being unsubstituted or substituted by m radicals $R^8$ and/or carrying at its nitrogen atom, if present, a radical $R^9$ as defined above. Particular preference is given to those 5-membered heteroaromatic radicals Het which are selected from 2-furyl, 3-furyl, 2-thienyl, 3-thienyl, 2-pyrrolyl, 3-pyrrolyl, 2-oxazolyl, 4-oxazolyl, 5-oxazolyl, 2-thiazoyl, 4-thiazolyl, 5-thiazolyl, 2-imidazolyl, 4-imidazolyl, 5-imidazolyl, 3-isoxazolyl, 4-isoxazolyl, 5-isoxazoly, 3-isothiazolyl, 4-isothiazolyl, 5-isothiazoly, 3-pyrazolyl, 4-pyrazolyl, 5-pyrazolyl, 1,3,4-oxadiazol-2-yl, 1,3,4-thiadiazol-2-yl, 1,2,4-oxadiazol-3-yl, 1,2,4-thiadiazol-5-yl, 1,2,4-oxadiazol-5-yl, 1,2,4-thiadiazol-5-yl, 4H-1,2,4-triazol-3-yl, 1H-1,2,4-triazol-3-yl, 2H-1,2,4-triazol-3-yl, 3H-1,2,3-triazol-4-yl, 1H-1,2,3-triazol-4-yl, 1H-1,2,3,4-tetrazol-5-yl, 1,2,3-oxadiazol-4-yl, 1,2,3-oxadiazol-5-yl, 1,2,3-thiadiazol-4-yl and 1,2,3-thiadiazol-5-yl. Het may be unsubstituted or substituted by m radicals $R^8$ and/or may carry at its nitrogen atom, if present, a radical $R^9$ wherein $R^8$, $R^9$ and m are as defined above.

Examples of preferred 5-membered heteroaromatic radicals Het include

Het.1

Het.2

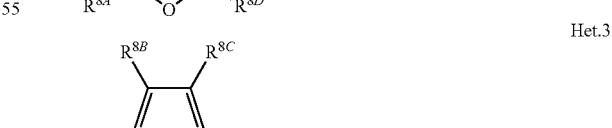

Het.3

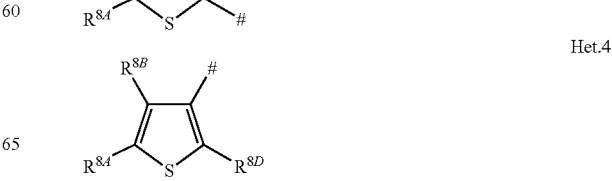

Het.4

-continued
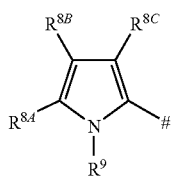 Het.5
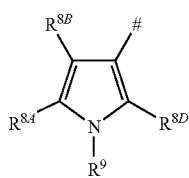 Het.6
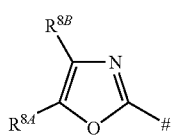 Het.7
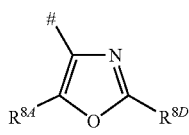 Het.8
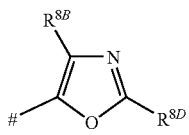 Het.9
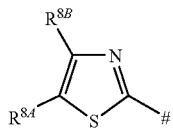 Het.10
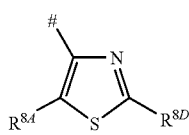 Het.11
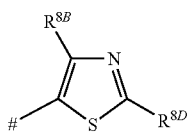 Het.12
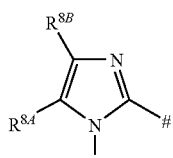 Het.13
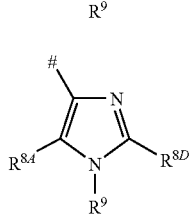 Het.14
-continued
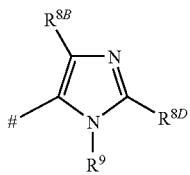 Het.15
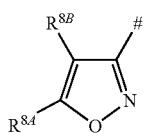 Het.16
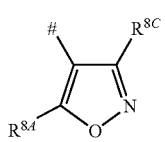 Het.17
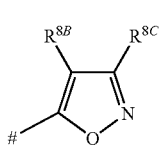 Het.18
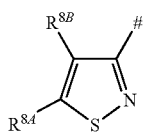 Het.19
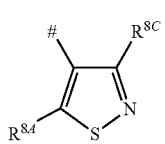 Het.20
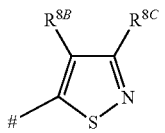 Het.21
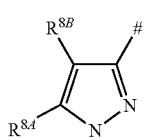 Het.22
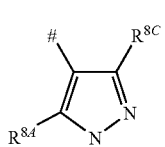 Het.23
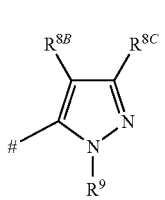 Het.24

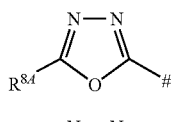 Het.25

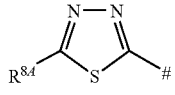 Het.26

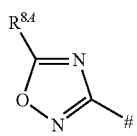 Het.27

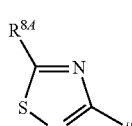 Het.28

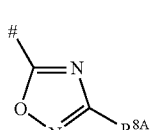 Het.29

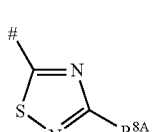 Het.30

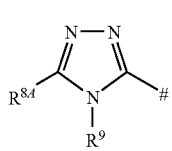 Het.31

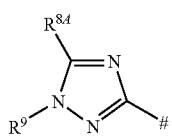 Het.32

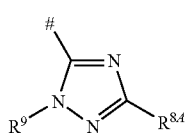 Het.33

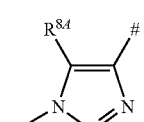 Het.34

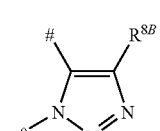 Het.35

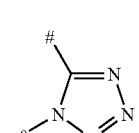 Het.36

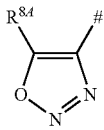 Het.37

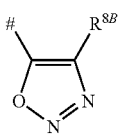 Het.38

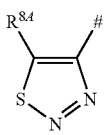 Het.39

Het.40 wherein # denotes the position of attachment in formula I and wherein $R^{8A}$, $R^{8B}$, $R^{8C}$, $R^{8D}$ and $R^{8E}$, independently of each other, are hydrogen or have one of the meanings given for $R^8$, in particular hydrogen and the meanings given for $R^8$ as being preferred, and $R^9$ has the meanings as given above, in particular the meanings given as being preferred.

A preferred embodiment of the invention relates to compounds I wherein Het is selected from the radicals of formulae Het.1, Het.2, Het.3, Het.4, Het.5, Het.6, Het.7, Het.8, Het.9, Het.10, Het.11, Het.12, Het.13, Het.14, Het.15, Het.16, Het.17, Het.18, Het.19, Het.20, Het.21, Het.22, Het.23, Het.24, Het.25, Het.26, Het.27, Het.28, Het.29 and Het.30.

More preferred are compounds I wherein Het is selected from the radicals of formulae Het.1, Het.2, Het.3, Het.4, Het.5, Het.6, Het.22, Het.23 and Het.24.

Especially preferred are compounds I wherein Het is selected from Het.1, Het.2, Het.3 and Het.4.

Likewise especially preferred are Het.22, Het.23 and Het.24.

In particular preferred are compounds I wherein Het is selected from the radicals of formulae Het.1, Het.3, Het.4, Het.6 and Het.23.

Preference is also given to compounds I wherein Het is a 6-membered heteroaromatic ring as defined above. Particular preference is given to those 6-membered heteroaromatic radicals Het which are selected from pyridin-2-yl, N-oxide of pyridin-2-yl, pyridin-3-yl, N-oxide of pyridin-3-yl, pyridin-4-yl, N-oxide of pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl and 1,2,4,5-tetrazin-3-yl and wherein Het is unsubstituted or substituted by m radicals $R^8$. If present, $R^8$ has the meanings given above, especially those meanings given as being preferred.

Examples of preferred 6-membered heteroaromatic radicals Het include

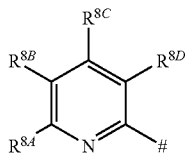
Het.41

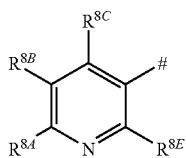
Het.42

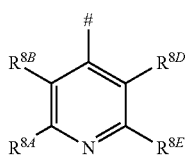
Het.43

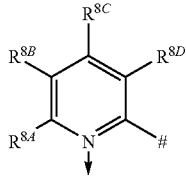
Het.44

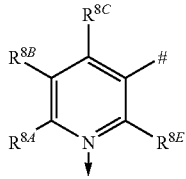
Het.45

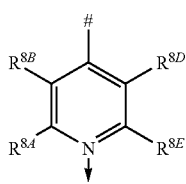
Het.46

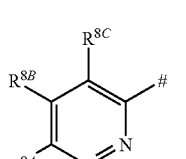
Het.47

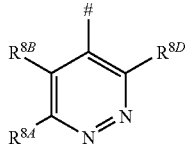
Het.48

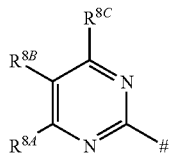
Het.49

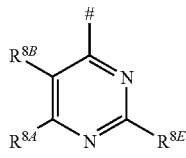
Het.50

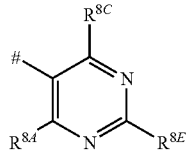
Het.51

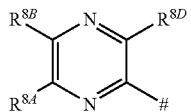
Het.52

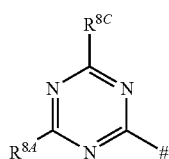
Het.53

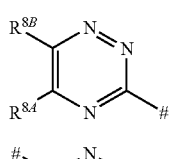
Het.54

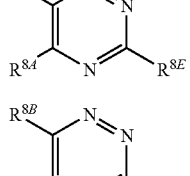
Het.55

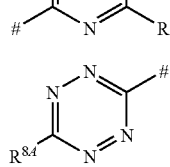
Het.56

Het.57 wherein # denotes the position of attachment in formula I and wherein $R^{8A}$, $R^{8B}$, $R^{8C}$, $R^{8D}$ and $R^{8E}$, independently of each other, are hydrogen or have one of the meanings given for $R^8$, especially hydrogen and the meanings given for $R^8$ as being preferred.

A preferred embodiment of the invention relates to compound I wherein Het is selected from Het.41, Het.42, Het.43, Het.49, Het.50 and Het.51. More preferred are compounds I wherein Het is selected from Het.41, Het.42 and Het.43, in particular from Het.41 and Het.43.

Examples of radicals Het are in particular those in which $R^{8A}$, $R^{8B}$, $R^{8C}$, $R^{8D}$ and $R^{8E}$, and $R^9$, if present, together have the meanings given in one row of table B.

TABLE B

| Radical | Het | R<sup>8A</sup> | R<sup>8B</sup> | R<sup>8C</sup> | R<sup>8D</sup> | R<sup>8E</sup> | R<sup>9</sup> |
|---|---|---|---|---|---|---|---|
| Het-R.1 | Het.1 | H | H | H | / | / | / |
| Het-R.2 | Het.1 | CH$_3$ | H | H | / | / | / |
| Het-R.3 | Het.1 | H | CH$_3$ | H | / | / | / |
| Het-R.4 | Het.1 | H | H | CH$_3$ | / | / | / |
| Het-R.5 | Het.1 | CF$_3$ | H | H | / | / | / |
| Het-R.6 | Het.1 | H | CF$_3$ | H | / | / | / |
| Het-R.7 | Het.1 | H | H | CF$_3$ | / | / | / |
| Het-R.8 | Het.1 | Cl | H | H | / | / | / |
| Het-R.9 | Het.1 | H | Cl | H | / | / | / |
| Het-R.10 | Het.1 | H | H | Cl | / | / | / |
| Het-R.11 | Het.1 | CH$_3$ | CH$_3$ | H | / | / | / |
| Het-R.12 | Het.1 | CH$_3$ | Cl | H | / | / | / |
| Het-R.13 | Het.1 | CH$_3$ | CF$_3$ | H | / | / | / |
| Het-R.14 | Het.1 | CH$_3$ | F | H | / | / | / |
| Het-R.15 | Het.1 | CF$_3$ | CH$_3$ | H | / | / | / |
| Het-R.16 | Het.1 | CF$_3$ | Cl | H | / | / | / |
| Het-R.17 | Het.1 | CF$_3$ | CF$_3$ | H | / | / | / |
| Het-R.18 | Het.1 | CF$_3$ | F | H | / | / | / |
| Het-R.19 | Het.1 | Cl | CH$_3$ | H | / | / | / |
| Het-R.20 | Het.1 | Cl | Cl | H | / | / | / |
| Het-R.21 | Het.1 | Cl | CF$_3$ | H | / | / | / |
| Het-R.22 | Het.1 | Cl | F | H | / | / | / |
| Het-R.23 | Het.1 | F | CH$_3$ | H | / | / | / |
| Het-R.24 | Het.1 | F | Cl | H | / | / | / |
| Het-R.25 | Het.1 | F | CF$_3$ | H | / | / | / |
| Het-R.26 | Het.1 | F | F | H | / | / | / |
| Het-R.27 | Het.1 | CH$_3$ | H | CH$_3$ | / | / | / |
| Het-R.28 | Het.1 | CH$_3$ | H | Cl | / | / | / |
| Het-R.29 | Het.1 | CH$_3$ | H | CF$_3$ | / | / | / |
| Het-R.30 | Het.1 | CH$_3$ | H | F | / | / | / |
| Het-R.31 | Het.1 | CF$_3$ | H | CH$_3$ | / | / | / |
| Het-R.32 | Het.1 | CF$_3$ | H | Cl | / | / | / |
| Het-R.33 | Het.1 | CF$_3$ | H | CF$_3$ | / | / | / |
| Het-R.34 | Het.1 | CF$_3$ | H | F | / | / | / |
| Het-R.35 | Het.1 | Cl | H | CH$_3$ | / | / | / |
| Het-R.36 | Het.1 | Cl | H | Cl | / | / | / |
| Het-R.37 | Het.1 | Cl | H | CF$_3$ | / | / | / |
| Het-R.38 | Het.1 | Cl | H | F | / | / | / |
| Het-R.39 | Het.1 | F | H | CH$_3$ | / | / | / |
| Het-R.40 | Het.1 | F | H | Cl | / | / | / |
| Het-R.41 | Het.1 | F | H | CF$_3$ | / | / | / |
| Het-R.42 | Het.1 | F | H | F | / | / | / |
| Het-R.43 | Het.1 | H | CH$_3$ | CH$_3$ | / | / | / |
| Het-R.44 | Het.1 | H | CH$_3$ | Cl | / | / | / |
| Het-R.45 | Het.1 | H | CH$_3$ | CF$_3$ | / | / | / |
| Het-R.46 | Het.1 | H | CH$_3$ | F | / | / | / |
| Het-R.47 | Het.1 | H | CF$_3$ | CH$_3$ | / | / | / |
| Het-R.48 | Het.1 | H | CF$_3$ | Cl | / | / | / |
| Het-R.49 | Het.1 | H | CF$_3$ | CF$_3$ | / | / | / |
| Het-R.50 | Het.1 | H | CF$_3$ | F | / | / | / |
| Het-R.51 | Het.1 | H | Cl | CH$_3$ | / | / | / |
| Het-R.52 | Het.1 | H | Cl | Cl | / | / | / |
| Het-R.53 | Het.1 | H | Cl | CF$_3$ | / | / | / |
| Het-R.54 | Het.1 | H | Cl | F | / | / | / |
| Het-R.55 | Het.1 | H | F | CH$_3$ | / | / | / |
| Het-R.56 | Het.1 | H | F | Cl | / | / | / |
| Het-R.57 | Het.1 | H | F | CF$_3$ | / | / | / |
| Het-R.58 | Het.1 | H | F | F | / | / | / |
| Het-R.59 | Het.2 | H | H | / | H | / | / |
| Het-R.60 | Het.2 | CH$_3$ | H | / | H | / | / |
| Het-R.61 | Het.2 | H | CH$_3$ | / | H | / | / |
| Het-R.62 | Het.2 | H | H | / | CH$_3$ | / | / |
| Het-R.63 | Het.2 | CF$_3$ | H | / | H | / | / |
| Het-R.64 | Het.2 | H | CF$_3$ | / | H | / | / |
| Het-R.65 | Het.2 | H | H | / | CF$_3$ | / | / |
| Het-R.66 | Het.2 | Cl | H | / | H | / | / |
| Het-R.67 | Het.2 | H | Cl | / | H | / | / |
| Het-R.68 | Het.2 | H | H | / | Cl | / | / |
| Het-R.69 | Het.2 | CH$_3$ | CH$_3$ | / | H | / | / |
| Het-R.70 | Het.2 | CH$_3$ | Cl | / | H | / | / |
| Het-R.71 | Het.2 | CH$_3$ | CF$_3$ | / | H | / | / |
| Het-R.72 | Het.2 | CH$_3$ | F | / | H | / | / |
| Het-R.73 | Het.2 | Cl | CH$_3$ | / | H | / | / |
| Het-R.74 | Het.2 | Cl | Cl | / | H | / | / |
| Het-R.75 | Het.2 | Cl | CF$_3$ | / | H | / | / |
| Het-R.76 | Het.2 | Cl | F | / | H | / | / |
| Het-R.77 | Het.2 | CF$_3$ | CH$_3$ | / | H | / | / |
| Het-R.78 | Het.2 | CF$_3$ | Cl | / | H | / | / |

TABLE B-continued

| Radical | Het | R<sup>8A</sup> | R<sup>8B</sup> | R<sup>8C</sup> | R<sup>8D</sup> | R<sup>8E</sup> | R<sup>9</sup> |
|---|---|---|---|---|---|---|---|
| Het-R.79 | Het.2 | CF$_3$ | CF$_3$ | / | H | / | / |
| Het-R.80 | Het.2 | CF$_3$ | F | / | H | / | / |
| Het-R.81 | Het.2 | F | CH$_3$ | / | H | / | / |
| Het-R.82 | Het.2 | F | Cl | / | H | / | / |
| Het-R.83 | Het.2 | F | CF$_3$ | / | H | / | / |
| Het-R.84 | Het.2 | F | F | / | H | / | / |
| Het-R.85 | Het.2 | CH$_3$ | H | / | CH$_3$ | / | / |
| Het-R.86 | Het.2 | CH$_3$ | H | / | Cl | / | / |
| Het-R.87 | Het.2 | CH$_3$ | H | / | CF$_3$ | / | / |
| Het-R.88 | Het.2 | CH$_3$ | H | / | F | / | / |
| Het-R.89 | Het.2 | Cl | H | / | CH$_3$ | / | / |
| Het-R.90 | Het.2 | Cl | H | / | Cl | / | / |
| Het-R.91 | Het.2 | Cl | H | / | CF$_3$ | / | / |
| Het-R.92 | Het.2 | Cl | H | / | F | / | / |
| Het-R.93 | Het.2 | CF$_3$ | H | / | CH$_3$ | / | / |
| Het-R.94 | Het.2 | CF$_3$ | H | / | Cl | / | / |
| Het-R.95 | Het.2 | CF$_3$ | H | / | CF$_3$ | / | / |
| Het-R.96 | Het.2 | CF$_3$ | H | / | F | / | / |
| Het-R.97 | Het.2 | F | H | / | CH$_3$ | / | / |
| Het-R.98 | Het.2 | F | H | / | Cl | / | / |
| Het-R.99 | Het.2 | F | H | / | CF$_3$ | / | / |
| Het-R.100 | Het.2 | F | H | / | F | / | / |
| Het-R.101 | Het.2 | H | CH$_3$ | / | CH$_3$ | / | / |
| Het-R.102 | Het.2 | H | CH$_3$ | / | Cl | / | / |
| Het-R.103 | Het.2 | H | CH$_3$ | / | CF$_3$ | / | / |
| Het-R.104 | Het.2 | H | CH$_3$ | / | F | / | / |
| Het-R.105 | Het.2 | H | Cl | / | CH$_3$ | / | / |
| Het-R.106 | Het.2 | H | Cl | / | Cl | / | / |
| Het-R.107 | Het.2 | H | Cl | / | CF$_3$ | / | / |
| Het-R.108 | Het.2 | H | Cl | / | F | / | / |
| Het-R.109 | Het.2 | H | CF$_3$ | / | CH$_3$ | / | / |
| Het-R.110 | Het.2 | H | CF$_3$ | / | Cl | / | / |
| Het-R.111 | Het.2 | H | CF$_3$ | / | CF$_3$ | / | / |
| Het-R.112 | Het.2 | H | CF$_3$ | / | F | / | / |
| Het-R.113 | Het.2 | H | F | / | CH$_3$ | / | / |
| Het-R.114 | Het.2 | H | F | / | Cl | / | / |
| Het-R.115 | Het.2 | H | F | / | CF$_3$ | / | / |
| Het-R.116 | Het.2 | H | F | / | F | / | / |
| Het-R.117 | Het.3 | H | H | H | / | / | / |
| Het-R.118 | Het.3 | CH$_3$ | H | H | / | / | / |
| Het-R.119 | Het.3 | H | CH$_3$ | H | / | / | / |
| Het-R.120 | Het.3 | H | H | CH$_3$ | / | / | / |
| Het-R.121 | Het.3 | CF$_3$ | H | H | / | / | / |
| Het-R.122 | Het.3 | H | CF$_3$ | H | / | / | / |
| Het-R.123 | Het.3 | H | H | CF$_3$ | / | / | / |
| Het-R.124 | Het.3 | Cl | H | H | / | / | / |
| Het-R.125 | Het.3 | H | Cl | H | / | / | / |
| Het-R.126 | Het.3 | H | H | Cl | / | / | / |
| Het-R.127 | Het.3 | CH$_3$ | CH$_3$ | H | / | / | / |
| Het-R.128 | Het.3 | CH$_3$ | Cl | H | / | / | / |
| Het-R.129 | Het.3 | CH$_3$ | CF$_3$ | H | / | / | / |
| Het-R.130 | Het.3 | CH$_3$ | F | H | / | / | / |
| Het-R.131 | Het.3 | CF$_3$ | CH$_3$ | H | / | / | / |
| Het-R.132 | Het.3 | CF$_3$ | Cl | H | / | / | / |
| Het-R.133 | Het.3 | CF$_3$ | CF$_3$ | H | / | / | / |
| Het-R.134 | Het.3 | CF$_3$ | F | H | / | / | / |
| Het-R.135 | Het.3 | Cl | CH$_3$ | H | / | / | / |
| Het-R.136 | Het.3 | Cl | Cl | H | / | / | / |
| Het-R.137 | Het.3 | Cl | CF$_3$ | H | / | / | / |
| Het-R.138 | Het.3 | Cl | F | H | / | / | / |
| Het-R.139 | Het.3 | F | CH$_3$ | H | / | / | / |
| Het-R.140 | Het.3 | F | Cl | H | / | / | / |
| Het-R.141 | Het.3 | F | CF$_3$ | H | / | / | / |
| Het-R.142 | Het.3 | F | F | H | / | / | / |
| Het-R.143 | Het.3 | CH$_3$ | H | CH$_3$ | / | / | / |
| Het-R.144 | Het.3 | CH$_3$ | H | Cl | / | / | / |
| Het-R.145 | Het.3 | CH$_3$ | H | CF$_3$ | / | / | / |
| Het-R.146 | Het.3 | CH$_3$ | H | F | / | / | / |
| Het-R.147 | Het.3 | CF$_3$ | H | CH$_3$ | / | / | / |
| Het-R.148 | Het.3 | CF$_3$ | H | Cl | / | / | / |
| Het-R.149 | Het.3 | CF$_3$ | H | CF$_3$ | / | / | / |
| Het-R.150 | Het.3 | CF$_3$ | H | F | / | / | / |
| Het-R.151 | Het.3 | Cl | H | CH$_3$ | / | / | / |
| Het-R.152 | Het.3 | Cl | H | Cl | / | / | / |
| Het-R.153 | Het.3 | Cl | H | CF$_3$ | / | / | / |
| Het-R.154 | Het.3 | Cl | H | F | / | / | / |
| Het-R.155 | Het.3 | F | H | CH$_3$ | / | / | / |
| Het-R.156 | Het.3 | F | H | Cl | / | / | / |

TABLE B-continued

| Radical | Het | $R^{8A}$ | $R^{8B}$ | $R^{8C}$ | $R^{8D}$ | $R^{8E}$ | $R^9$ |
|---|---|---|---|---|---|---|---|
| Het-R.157 | Het.3 | F | H | CF$_3$ | / | / | / |
| Het-R.158 | Het.3 | F | H | F | / | / | / |
| Het-R.159 | Het.3 | H | CH$_3$ | CH$_3$ | / | / | / |
| Het-R.160 | Het.3 | H | CH$_3$ | Cl | / | / | / |
| Het-R.161 | Het.3 | H | CH$_3$ | CF$_3$ | / | / | / |
| Het-R.162 | Het.3 | H | CH$_3$ | F | / | / | / |
| Het-R.163 | Het.3 | H | CF$_3$ | CH$_3$ | / | / | / |
| Het-R.164 | Het.3 | H | CF$_3$ | Cl | / | / | / |
| Het-R.165 | Het.3 | H | CF$_3$ | CF$_3$ | / | / | / |
| Het-R.166 | Het.3 | H | CF$_3$ | F | / | / | / |
| Het-R.167 | Het.3 | H | Cl | CH$_3$ | / | / | / |
| Het-R.168 | Het.3 | H | Cl | Cl | / | / | / |
| Het-R.169 | Het.3 | H | Cl | CF$_3$ | / | / | / |
| Het-R.170 | Het.3 | H | Cl | F | / | / | / |
| Het-R.171 | Het.3 | H | F | CH$_3$ | / | / | / |
| Het-R.172 | Het.3 | H | F | Cl | / | / | / |
| Het-R.173 | Het.3 | H | F | CF$_3$ | / | / | / |
| Het-R.174 | Het.3 | H | F | F | / | / | / |
| Het-R.175 | Het.4 | H | H | / | H | / | / |
| Het-R.176 | Het.4 | CH$_3$ | H | / | H | / | / |
| Het-R.177 | Het.4 | H | CH$_3$ | / | H | / | / |
| Het-R.178 | Het.4 | H | H | / | CH$_3$ | / | / |
| Het-R.179 | Het.4 | CF$_3$ | H | / | H | / | / |
| Het-R.180 | Het.4 | H | CF$_3$ | / | H | / | / |
| Het-R.181 | Het.4 | H | H | / | CF$_3$ | / | / |
| Het-R.182 | Het.4 | Cl | H | / | H | / | / |
| Het-R.183 | Het.4 | H | Cl | / | H | / | / |
| Het-R.184 | Het.4 | H | H | / | Cl | / | / |
| Het-R.185 | Het.4 | CH$_3$ | CH$_3$ | / | H | / | / |
| Het-R.186 | Het.4 | CH$_3$ | Cl | / | H | / | / |
| Het-R.187 | Het.4 | CH$_3$ | CF$_3$ | / | H | / | / |
| Het-R.188 | Het.4 | CH$_3$ | F | / | H | / | / |
| Het-R.189 | Het.4 | Cl | CH$_3$ | / | H | / | / |
| Het-R.190 | Het.4 | Cl | Cl | / | H | / | / |
| Het-R.191 | Het.4 | Cl | CF$_3$ | / | H | / | / |
| Het-R.192 | Het.4 | Cl | F | / | H | / | / |
| Het-R.193 | Het.4 | CF$_3$ | CH$_3$ | / | H | / | / |
| Het-R.194 | Het.4 | CF$_3$ | Cl | / | H | / | / |
| Het-R.195 | Het.4 | CF$_3$ | CF$_3$ | / | H | / | / |
| Het-R.196 | Het.4 | CF$_3$ | F | / | H | / | / |
| Het-R.197 | Het.4 | F | CH$_3$ | / | H | / | / |
| Het-R.198 | Het.4 | F | Cl | / | H | / | / |
| Het-R.199 | Het.4 | F | CF$_3$ | / | H | / | / |
| Het-R.200 | Het.4 | F | F | / | H | / | / |
| Het-R.201 | Het.4 | CH$_3$ | H | / | CH$_3$ | / | / |
| Het-R.202 | Het.4 | CH$_3$ | H | / | Cl | / | / |
| Het-R.203 | Het.4 | CH$_3$ | H | / | CF$_3$ | / | / |
| Het-R.204 | Het.4 | CH$_3$ | H | / | F | / | / |
| Het-R.205 | Het.4 | Cl | H | / | CH$_3$ | / | / |
| Het-R.206 | Het.4 | Cl | H | / | Cl | / | / |
| Het-R.207 | Het.4 | Cl | H | / | CF$_3$ | / | / |
| Het-R.208 | Het.4 | Cl | H | / | F | / | / |
| Het-R.209 | Het.4 | CF$_3$ | H | / | CH$_3$ | / | / |
| Het-R.210 | Het.4 | CF$_3$ | H | / | Cl | / | / |
| Het-R.211 | Het.4 | CF$_3$ | H | / | CF$_3$ | / | / |
| Het-R.212 | Het.4 | CF$_3$ | H | / | F | / | / |
| Het-R.213 | Het.4 | F | H | / | CH$_3$ | / | / |
| Het-R.214 | Het.4 | F | H | / | Cl | / | / |
| Het-R.215 | Het.4 | F | H | / | CF$_3$ | / | / |
| Het-R.216 | Het.4 | F | H | / | F | / | / |
| Het-R.217 | Het.4 | H | CH$_3$ | / | CH$_3$ | / | / |
| Het-R.218 | Het.4 | H | CH$_3$ | / | Cl | / | / |
| Het-R.219 | Het.4 | H | CH$_3$ | / | CF$_3$ | / | / |
| Het-R.220 | Het.4 | H | CH$_3$ | / | F | / | / |
| Het-R.221 | Het.4 | H | Cl | / | CH$_3$ | / | / |
| Het-R.222 | Het.4 | H | Cl | / | Cl | / | / |
| Het-R.223 | Het.4 | H | Cl | / | CF$_3$ | / | / |
| Het-R.224 | Het.4 | H | Cl | / | F | / | / |
| Het-R.225 | Het.4 | H | CF$_3$ | / | CH$_3$ | / | / |
| Het-R.226 | Het.4 | H | CF$_3$ | / | Cl | / | / |
| Het-R.227 | Het.4 | H | CF$_3$ | / | CF$_3$ | / | / |
| Het-R.228 | Het.4 | H | CF$_3$ | / | F | / | / |
| Het-R.229 | Het.4 | H | F | / | CH$_3$ | / | / |
| Het-R.230 | Het.4 | H | F | / | Cl | / | / |
| Het-R.231 | Het.4 | H | F | / | CF$_3$ | / | / |
| Het-R.232 | Het.4 | H | F | / | F | / | / |
| Het-R.233 | Het.5 | H | H | H | / | / | H |
| Het-R.234 | Het.5 | CH$_3$ | H | H | / | / | H |
| Het-R.235 | Het.5 | H | CH$_3$ | H | / | / | H |
| Het-R.236 | Het.5 | H | H | CH$_3$ | / | / | H |
| Het-R.237 | Het.5 | CF$_3$ | H | H | / | / | H |
| Het-R.238 | Het.5 | H | CF$_3$ | H | / | / | H |
| Het-R.239 | Het.5 | H | H | CF$_3$ | / | / | H |
| Het-R.240 | Het.5 | Cl | H | H | / | / | H |
| Het-R.241 | Het.5 | H | Cl | H | / | / | H |
| Het-R.242 | Het.5 | H | H | Cl | / | / | H |
| Het-R.243 | Het.5 | H | H | H | / | / | CH$_3$ |
| Het-R.244 | Het.5 | CH$_3$ | H | H | / | / | CH$_3$ |
| Het-R.245 | Het.5 | H | CH$_3$ | H | / | / | CH$_3$ |
| Het-R.246 | Het.5 | H | H | CH$_3$ | / | / | CH$_3$ |
| Het-R.247 | Het.5 | CF$_3$ | H | H | / | / | CH$_3$ |
| Het-R.248 | Het.5 | H | CF$_3$ | H | / | / | CH$_3$ |
| Het-R.249 | Het.5 | H | H | CF$_3$ | / | / | CH$_3$ |
| Het-R.250 | Het.5 | Cl | H | H | / | / | CH$_3$ |
| Het-R.251 | Het.5 | H | Cl | H | / | / | CH$_3$ |
| Het-R.252 | Het.5 | H | H | Cl | / | / | CH$_3$ |
| Het-R.253 | Het.5 | CH$_3$ | CH$_3$ | H | / | / | CH$_3$ |
| Het-R.254 | Het.5 | CH$_3$ | Cl | H | / | / | CH$_3$ |
| Het-R.255 | Het.5 | CH$_3$ | CF$_3$ | H | / | / | CH$_3$ |
| Het-R.256 | Het.5 | CH$_3$ | F | H | / | / | CH$_3$ |
| Het-R.257 | Het.5 | CF$_3$ | CH$_3$ | H | / | / | CH$_3$ |
| Het-R.258 | Het.5 | CF$_3$ | Cl | H | / | / | CH$_3$ |
| Het-R.259 | Het.5 | CF$_3$ | CF$_3$ | H | / | / | CH$_3$ |
| Het-R.260 | Het.5 | CF$_3$ | F | H | / | / | CH$_3$ |
| Het-R.261 | Het.5 | Cl | CH$_3$ | H | / | / | CH$_3$ |
| Het-R.262 | Het.5 | Cl | Cl | H | / | / | CH$_3$ |
| Het-R.263 | Het.5 | Cl | CF$_3$ | H | / | / | CH$_3$ |
| Het-R.264 | Het.5 | Cl | F | H | / | / | CH$_3$ |
| Het-R.265 | Het.5 | F | CH$_3$ | H | / | / | CH$_3$ |
| Het-R.266 | Het.5 | F | Cl | H | / | / | CH$_3$ |
| Het-R.267 | Het.5 | F | CF$_3$ | H | / | / | CH$_3$ |
| Het-R.268 | Het.5 | F | F | H | / | / | CH$_3$ |
| Het-R.269 | Het.5 | CH$_3$ | H | CH$_3$ | / | / | CH$_3$ |
| Het-R.270 | Het.5 | CH$_3$ | H | Cl | / | / | CH$_3$ |
| Het-R.271 | Het.5 | CH$_3$ | H | CF$_3$ | / | / | CH$_3$ |
| Het-R.272 | Het.5 | CH$_3$ | H | F | / | / | CH$_3$ |
| Het-R.273 | Het.5 | CF$_3$ | H | CH$_3$ | / | / | CH$_3$ |
| Het-R.274 | Het.5 | CF$_3$ | H | Cl | / | / | CH$_3$ |
| Het-R.275 | Het.5 | CF$_3$ | H | CF$_3$ | / | / | CH$_3$ |
| Het-R.276 | Het.5 | CF$_3$ | H | F | / | / | CH$_3$ |
| Het-R.277 | Het.5 | Cl | H | CH$_3$ | / | / | CH$_3$ |
| Het-R.278 | Het.5 | Cl | H | Cl | / | / | CH$_3$ |
| Het-R.279 | Het.5 | Cl | H | CF$_3$ | / | / | CH$_3$ |
| Het-R.280 | Het.5 | Cl | H | F | / | / | CH$_3$ |
| Het-R.281 | Het.5 | F | H | CH$_3$ | / | / | CH$_3$ |
| Het-R.282 | Het.5 | F | H | Cl | / | / | CH$_3$ |
| Het-R.283 | Het.5 | F | H | CF$_3$ | / | / | CH$_3$ |
| Het-R.284 | Het.5 | F | H | F | / | / | CH$_3$ |
| Het-R.285 | Het.5 | H | CH$_3$ | CH$_3$ | / | / | CH$_3$ |
| Het-R.286 | Het.5 | H | CH$_3$ | Cl | / | / | CH$_3$ |
| Het-R.287 | Het.5 | H | CH$_3$ | CF$_3$ | / | / | CH$_3$ |
| Het-R.288 | Het.5 | H | CH$_3$ | F | / | / | CH$_3$ |
| Het-R.289 | Het.5 | H | CF$_3$ | CH$_3$ | / | / | CH$_3$ |
| Het-R.290 | Het.5 | H | CF$_3$ | Cl | / | / | CH$_3$ |
| Het-R.291 | Het.5 | H | CF$_3$ | CF$_3$ | / | / | CH$_3$ |
| Het-R.292 | Het.5 | H | CF$_3$ | F | / | / | CH$_3$ |
| Het-R.293 | Het.5 | H | Cl | CH$_3$ | / | / | CH$_3$ |
| Het-R.294 | Het.5 | H | Cl | Cl | / | / | CH$_3$ |
| Het-R.295 | Het.5 | H | Cl | CF$_3$ | / | / | CH$_3$ |
| Het-R.296 | Het.5 | H | Cl | F | / | / | CH$_3$ |
| Het-R.297 | Het.5 | H | F | CH$_3$ | / | / | CH$_3$ |
| Het-R.298 | Het.5 | H | F | Cl | / | / | CH$_3$ |
| Het-R.299 | Het.5 | H | F | CF$_3$ | / | / | CH$_3$ |
| Het-R.300 | Het.5 | H | F | F | / | / | CH$_3$ |
| Het-R.301 | Het.6 | H | H | / | H | / | H |
| Het-R.302 | Het.6 | CH$_3$ | H | / | H | / | H |
| Het-R.303 | Het.6 | H | CH$_3$ | / | H | / | H |
| Het-R.304 | Het.6 | H | H | / | CH$_3$ | / | H |
| Het-R.305 | Het.6 | CF$_3$ | H | / | H | / | H |
| Het-R.306 | Het.6 | H | CF$_3$ | / | H | / | H |
| Het-R.307 | Het.6 | H | H | / | CF$_3$ | / | H |
| Het-R.308 | Het.6 | Cl | H | / | H | / | H |
| Het-R.309 | Het.6 | H | Cl | / | H | / | H |
| Het-R.310 | Het.6 | H | H | / | Cl | / | H |
| Het-R.311 | Het.6 | H | H | / | H | / | CH$_3$ |
| Het-R.312 | Het.6 | CH$_3$ | H | / | H | / | CH$_3$ |

TABLE B-continued

| Radical | Het | R$^{8A}$ | R$^{8B}$ | R$^{8C}$ | R$^{8D}$ | R$^{8E}$ | R$^9$ |
|---|---|---|---|---|---|---|---|
| Het-R.313 | Het.6 | H | CH$_3$ | / | H | / | CH$_3$ |
| Het-R.314 | Het.6 | H | H | / | CH$_3$ | / | CH$_3$ |
| Het-R.315 | Het.6 | CF$_3$ | H | / | H | / | CH$_3$ |
| Het-R.316 | Het.6 | H | CF$_3$ | / | H | / | CH$_3$ |
| Het-R.317 | Het.6 | H | H | / | CF$_3$ | / | CH$_3$ |
| Het-R.318 | Het.6 | Cl | H | / | H | / | CH$_3$ |
| Het-R.319 | Het.6 | H | Cl | / | H | / | CH$_3$ |
| Het-R.320 | Het.6 | H | H | / | Cl | / | CH$_3$ |
| Het-R.321 | Het.6 | CH$_3$ | CH$_3$ | / | H | / | CH$_3$ |
| Het-R.322 | Het.6 | CH$_3$ | Cl | / | H | / | CH$_3$ |
| Het-R.323 | Het.6 | CH$_3$ | CF$_3$ | / | H | / | CH$_3$ |
| Het-R.324 | Het.6 | CH$_3$ | F | / | H | / | CH$_3$ |
| Het-R.325 | Het.6 | Cl | CH$_3$ | / | H | / | CH$_3$ |
| Het-R.326 | Het.6 | Cl | Cl | / | H | / | CH$_3$ |
| Het-R.327 | Het.6 | Cl | CF$_3$ | / | H | / | CH$_3$ |
| Het-R.328 | Het.6 | Cl | F | / | H | / | CH$_3$ |
| Het-R.329 | Het.6 | CF$_3$ | CH$_3$ | / | H | / | CH$_3$ |
| Het-R.330 | Het.6 | CF$_3$ | Cl | / | H | / | CH$_3$ |
| Het-R.331 | Het.6 | CF$_3$ | CF$_3$ | / | H | / | CH$_3$ |
| Het-R.332 | Het.6 | CF$_3$ | F | / | H | / | CH$_3$ |
| Het-R.333 | Het.6 | F | CH$_3$ | / | H | / | CH$_3$ |
| Het-R.334 | Het.6 | F | Cl | / | H | / | CH$_3$ |
| Het-R.335 | Het.6 | F | CF$_3$ | / | H | / | CH$_3$ |
| Het-R.336 | Het.6 | F | F | / | H | / | CH$_3$ |
| Het-R.337 | Het.6 | CH$_3$ | H | / | CH$_3$ | / | CH$_3$ |
| Het-R.338 | Het.6 | CH$_3$ | H | / | Cl | / | CH$_3$ |
| Het-R.339 | Het.6 | CH$_3$ | H | / | CF$_3$ | / | CH$_3$ |
| Het-R.340 | Het.6 | CH$_3$ | H | / | F | / | CH$_3$ |
| Het-R.341 | Het.6 | Cl | H | / | CH$_3$ | / | CH$_3$ |
| Het-R.342 | Het.6 | Cl | H | / | Cl | / | CH$_3$ |
| Het-R.343 | Het.6 | Cl | H | / | CF$_3$ | / | CH$_3$ |
| Het-R.344 | Het.6 | Cl | H | / | F | / | CH$_3$ |
| Het-R.345 | Het.6 | CF$_3$ | H | / | CH$_3$ | / | CH$_3$ |
| Het-R.346 | Het.6 | CF$_3$ | H | / | Cl | / | CH$_3$ |
| Het-R.347 | Het.6 | CF$_3$ | H | / | CF$_3$ | / | CH$_3$ |
| Het-R.348 | Het.6 | CF$_3$ | H | / | F | / | CH$_3$ |
| Het-R.349 | Het.6 | F | H | / | CH$_3$ | / | CH$_3$ |
| Het-R.350 | Het.6 | F | H | / | Cl | / | CH$_3$ |
| Het-R.351 | Het.6 | F | H | / | CF$_3$ | / | CH$_3$ |
| Het-R.352 | Het.6 | F | H | / | F | / | CH$_3$ |
| Het-R.353 | Het.6 | H | CH$_3$ | / | CH$_3$ | / | CH$_3$ |
| Het-R.354 | Het.6 | H | CH$_3$ | / | Cl | / | CH$_3$ |
| Het-R.355 | Het.6 | H | CH$_3$ | / | CF$_3$ | / | CH$_3$ |
| Het-R.356 | Het.6 | H | CH$_3$ | / | F | / | CH$_3$ |
| Het-R.357 | Het.6 | H | Cl | / | CH$_3$ | / | CH$_3$ |
| Het-R.358 | Het.6 | H | Cl | / | Cl | / | CH$_3$ |
| Het-R.359 | Het.6 | H | Cl | / | CF$_3$ | / | CH$_3$ |
| Het-R.360 | Het.6 | H | Cl | / | F | / | CH$_3$ |
| Het-R.361 | Het.6 | H | CF$_3$ | / | CH$_3$ | / | CH$_3$ |
| Het-R.362 | Het.6 | H | CF$_3$ | / | Cl | / | CH$_3$ |
| Het-R.363 | Het.6 | H | CF$_3$ | / | CF$_3$ | / | CH$_3$ |
| Het-R.364 | Het.6 | H | CF$_3$ | / | F | / | CH$_3$ |
| Het-R.365 | Het.6 | H | F | / | CH$_3$ | / | CH$_3$ |
| Het-R.366 | Het.6 | H | F | / | Cl | / | CH$_3$ |
| Het-R.367 | Het.6 | H | F | / | CF$_3$ | / | CH$_3$ |
| Het-R.368 | Het.6 | H | F | / | F | / | CH$_3$ |
| Het-R.369 | Het.7 | H | H | / | / | / | / |
| Het-R.370 | Het.7 | H | CH$_3$ | / | / | / | / |
| Het-R.371 | Het.7 | CH$_3$ | H | / | / | / | / |
| Het-R.372 | Het.7 | H | CF$_3$ | / | / | / | / |
| Het-R.373 | Het.7 | CF$_3$ | H | / | / | / | / |
| Het-R.374 | Het.7 | H | Cl | / | / | / | / |
| Het-R.375 | Het.7 | Cl | H | / | / | / | / |
| Het-R.376 | Het.8 | H | / | / | H | / | / |
| Het-R.377 | Het.8 | CH$_3$ | / | / | H | / | / |
| Het-R.378 | Het.8 | H | / | / | CH$_3$ | / | / |
| Het-R.379 | Het.8 | CF$_3$ | / | / | H | / | / |
| Het-R.380 | Het.8 | H | / | / | CF$_3$ | / | / |
| Het-R.381 | Het.8 | Cl | / | / | H | / | / |
| Het-R.382 | Het.8 | H | / | / | Cl | / | / |
| Het-R.383 | Het.9 | / | H | / | H | / | / |
| Het-R.384 | Het.9 | / | H | / | CH$_3$ | / | / |
| Het-R.385 | Het.9 | / | CH$_3$ | / | H | / | / |
| Het-R.386 | Het.9 | / | H | / | CF$_3$ | / | / |
| Het-R.387 | Het.9 | / | CF$_3$ | / | H | / | / |
| Het-R.388 | Het.9 | / | H | / | Cl | / | / |
| Het-R.389 | Het.9 | / | Cl | / | H | / | / |
| Het-R.390 | Het.10 | H | H | / | / | / | / |
| Het-R.391 | Het.10 | H | CH$_3$ | / | / | / | / |
| Het-R.392 | Het.10 | CH$_3$ | H | / | / | / | / |
| Het-R.393 | Het.10 | H | CF$_3$ | / | / | / | / |
| Het-R.394 | Het.10 | CF$_3$ | H | / | / | / | / |
| Het-R.395 | Het.10 | H | Cl | / | / | / | / |
| Het-R.396 | Het.10 | Cl | H | / | / | / | / |
| Het-R.397 | Het.11 | H | / | / | H | / | / |
| Het-R.398 | Het.11 | CH$_3$ | / | / | H | / | / |
| Het-R.399 | Het.11 | H | / | / | CH$_3$ | / | / |
| Het-R.400 | Het.11 | CF$_3$ | / | / | H | / | / |
| Het-R.401 | Het.11 | H | / | / | CF$_3$ | / | / |
| Het-R.402 | Het.11 | Cl | / | / | H | / | / |
| Het-R.403 | Het.11 | H | / | / | Cl | / | / |
| Het-R.404 | Het.12 | / | H | / | H | / | / |
| Het-R.405 | Het.12 | / | H | / | CH$_3$ | / | / |
| Het-R.406 | Het.12 | / | CH$_3$ | / | H | / | / |
| Het-R.407 | Het.12 | / | H | / | CF$_3$ | / | / |
| Het-R.408 | Het.12 | / | CF$_3$ | / | H | / | / |
| Het-R.409 | Het.12 | / | H | / | Cl | / | / |
| Het-R.410 | Het.12 | / | Cl | / | H | / | / |
| Het-R.411 | Het.13 | H | H | / | / | / | H |
| Het-R.412 | Het.13 | H | CH$_3$ | / | / | / | H |
| Het-R.413 | Het.13 | CH$_3$ | H | / | / | / | H |
| Het-R.414 | Het.13 | H | CF$_3$ | / | / | / | H |
| Het-R.415 | Het.13 | CF$_3$ | H | / | / | / | H |
| Het-R.416 | Het.13 | H | Cl | / | / | / | H |
| Het-R.417 | Het.13 | Cl | H | / | / | / | H |
| Het-R.418 | Het.13 | H | H | / | / | / | CH$_3$ |
| Het-R.419 | Het.13 | H | CH$_3$ | / | / | / | CH$_3$ |
| Het-R.420 | Het.13 | CH$_3$ | H | / | / | / | CH$_3$ |
| Het-R.421 | Het.13 | H | CF$_3$ | / | / | / | CH$_3$ |
| Het-R.422 | Het.13 | CF$_3$ | H | / | / | / | CH$_3$ |
| Het-R.423 | Het.13 | H | Cl | / | / | / | CH$_3$ |
| Het-R.424 | Het.13 | Cl | H | / | / | / | CH$_3$ |
| Het-R.425 | Het.14 | H | / | / | H | / | H |
| Het-R.426 | Het.14 | CH$_3$ | / | / | H | / | H |
| Het-R.427 | Het.14 | H | / | / | CH$_3$ | / | H |
| Het-R.428 | Het.14 | CF$_3$ | / | / | H | / | H |
| Het-R.429 | Het.14 | H | / | / | CF$_3$ | / | H |
| Het-R.430 | Het.14 | Cl | / | / | H | / | H |
| Het-R.431 | Het.14 | H | / | / | Cl | / | H |
| Het-R.432 | Het.14 | H | / | / | H | / | CH$_3$ |
| Het-R.433 | Het.14 | CH$_3$ | / | / | H | / | CH$_3$ |
| Het-R.434 | Het.14 | H | / | / | CH$_3$ | / | CH$_3$ |
| Het-R.435 | Het.14 | CF$_3$ | / | / | H | / | CH$_3$ |
| Het-R.436 | Het.14 | H | / | / | CF$_3$ | / | CH$_3$ |
| Het-R.437 | Het.14 | Cl | / | / | H | / | CH$_3$ |
| Het-R.438 | Het.14 | H | / | / | Cl | / | CH$_3$ |
| Het-R.439 | Het.15 | / | H | / | H | / | H |
| Het-R.440 | Het.15 | / | H | / | CH$_3$ | / | H |
| Het-R.441 | Het.15 | / | CH$_3$ | / | H | / | H |
| Het-R.442 | Het.15 | / | H | / | CF$_3$ | / | H |
| Het-R.443 | Het.15 | / | CF$_3$ | / | H | / | H |
| Het-R.444 | Het.15 | / | H | / | Cl | / | H |
| Het-R.445 | Het.15 | / | Cl | / | H | / | H |
| Het-R.446 | Het.15 | / | H | / | H | / | CH$_3$ |
| Het-R.447 | Het.15 | / | H | / | CH$_3$ | / | CH$_3$ |
| Het-R.448 | Het.15 | / | CH$_3$ | / | H | / | CH$_3$ |
| Het-R.449 | Het.15 | / | H | / | CF$_3$ | / | CH$_3$ |
| Het-R.450 | Het.15 | / | CF$_3$ | / | H | / | CH$_3$ |
| Het-R.451 | Het.15 | / | H | / | Cl | / | CH$_3$ |
| Het-R.452 | Het.15 | / | Cl | / | H | / | CH$_3$ |
| Het-R.453 | Het.16 | H | H | / | / | / | / |
| Het-R.454 | Het.16 | H | CH$_3$ | / | / | / | / |
| Het-R.455 | Het.16 | CH$_3$ | H | / | / | / | / |
| Het-R.456 | Het.16 | H | CF$_3$ | / | / | / | / |
| Het-R.457 | Het.16 | CF$_3$ | H | / | / | / | / |
| Het-R.458 | Het.16 | H | Cl | / | / | / | / |
| Het-R.459 | Het.16 | Cl | H | / | / | / | / |
| Het-R.460 | Het.17 | H | / | H | / | / | / |
| Het-R.461 | Het.17 | CH$_3$ | / | H | / | / | / |
| Het-R.462 | Het.17 | H | / | CH$_3$ | / | / | / |
| Het-R.463 | Het.17 | CF$_3$ | / | H | / | / | / |
| Het-R.464 | Het.17 | H | / | CF$_3$ | / | / | / |
| Het-R.465 | Het.17 | Cl | / | H | / | / | / |
| Het-R.466 | Het.17 | H | / | Cl | / | / | / |
| Het-R.467 | Het.18 | / | H | H | / | / | / |
| Het-R.468 | Het.18 | / | CH$_3$ | H | / | / | / |

TABLE B-continued

| Radical | Het | R$^{8A}$ | R$^{8B}$ | R$^{8C}$ | R$^{8D}$ | R$^{8E}$ | R$^9$ |
|---|---|---|---|---|---|---|---|
| Het-R.469 | Het.18 | / | H | CH$_3$ | / | / | / |
| Het-R.470 | Het.18 | / | CF$_3$ | H | / | / | / |
| Het-R.471 | Het.18 | / | H | CF$_3$ | / | / | / |
| Het-R.472 | Het.18 | / | Cl | H | / | / | / |
| Het-R.473 | Het.18 | / | H | Cl | / | / | / |
| Het-R.474 | Het.19 | H | H | / | / | / | / |
| Het-R.475 | Het.19 | H | CH$_3$ | / | / | / | / |
| Het-R.476 | Het.19 | CH$_3$ | H | / | / | / | / |
| Het-R.477 | Het.19 | H | CF$_3$ | / | / | / | / |
| Het-R.478 | Het.19 | CF$_3$ | H | / | / | / | / |
| Het-R.479 | Het.19 | H | Cl | / | / | / | / |
| Het-R.480 | Het.19 | Cl | H | / | / | / | / |
| Het-R.481 | Het.20 | H | / | H | / | / | / |
| Het-R.482 | Het.20 | CH$_3$ | / | H | / | / | / |
| Het-R.483 | Het.20 | H | / | CH$_3$ | / | / | / |
| Het-R.484 | Het.20 | CF$_3$ | / | H | / | / | / |
| Het-R.485 | Het.20 | H | / | CF$_3$ | / | / | / |
| Het-R.486 | Het.20 | Cl | / | H | / | / | / |
| Het-R.487 | Het.20 | H | / | Cl | / | / | / |
| Het-R.488 | Het.21 | / | H | H | / | / | / |
| Het-R.489 | Het.21 | / | CH$_3$ | H | / | / | / |
| Het-R.490 | Het.21 | / | H | CH$_3$ | / | / | / |
| Het-R.491 | Het.21 | / | CF$_3$ | H | / | / | / |
| Het-R.492 | Het.21 | / | H | CF$_3$ | / | / | / |
| Het-R.493 | Het.21 | / | Cl | H | / | / | / |
| Het-R.494 | Het.21 | / | H | Cl | / | / | / |
| Het-R.495 | Het.22 | H | H | / | / | / | H |
| Het-R.496 | Het.22 | H | CH$_3$ | / | / | / | H |
| Het-R.497 | Het.22 | CH$_3$ | H | / | / | / | H |
| Het-R.498 | Het.22 | H | CF$_3$ | / | / | / | H |
| Het-R.499 | Het.22 | CF$_3$ | H | / | / | / | H |
| Het-R.500 | Het.22 | H | Cl | / | / | / | H |
| Het-R.501 | Het.22 | Cl | H | / | / | / | H |
| Het-R.502 | Het.22 | H | H | / | / | / | CH$_3$ |
| Het-R.503 | Het.22 | H | CH$_3$ | / | / | / | CH$_3$ |
| Het-R.504 | Het.22 | CH$_3$ | H | / | / | / | CH$_3$ |
| Het-R.505 | Het.22 | H | CF$_3$ | / | / | / | CH$_3$ |
| Het-R.506 | Het.22 | CF$_3$ | H | / | / | / | CH$_3$ |
| Het-R.507 | Het.22 | H | Cl | / | / | / | CH$_3$ |
| Het-R.508 | Het.22 | Cl | H | / | / | / | CH$_3$ |
| Het-R.509 | Het.23 | H | / | H | / | / | H |
| Het-R.510 | Het.23 | CH$_3$ | / | H | / | / | H |
| Het-R.511 | Het.23 | H | / | CH$_3$ | / | / | H |
| Het-R.512 | Het.23 | CF$_3$ | / | H | / | / | H |
| Het-R.513 | Het.23 | H | / | CF$_3$ | / | / | H |
| Het-R.514 | Het.23 | Cl | / | H | / | / | H |
| Het-R.515 | Het.23 | H | / | Cl | / | / | H |
| Het-R.516 | Het.23 | H | / | H | / | / | CH$_3$ |
| Het-R.517 | Het.23 | CH$_3$ | / | H | / | / | CH$_3$ |
| Het-R.518 | Het.23 | H | / | CH$_3$ | / | / | CH$_3$ |
| Het-R.519 | Het.23 | CF$_3$ | / | H | / | / | CH$_3$ |
| Het-R.520 | Het.23 | H | / | CF$_3$ | / | / | CH$_3$ |
| Het-R.521 | Het.23 | Cl | / | H | / | / | CH$_3$ |
| Het-R.522 | Het.23 | H | / | Cl | / | / | CH$_3$ |
| Het-R.523 | Het.24 | / | H | H | / | / | H |
| Het-R.524 | Het.24 | / | CH$_3$ | H | / | / | H |
| Het-R.525 | Het.24 | / | H | CH$_3$ | / | / | H |
| Het-R.526 | Het.24 | / | CF$_3$ | H | / | / | H |
| Het-R.527 | Het.24 | / | H | CF$_3$ | / | / | H |
| Het-R.528 | Het.24 | / | Cl | H | / | / | H |
| Het-R.529 | Het.24 | / | H | Cl | / | / | H |
| Het-R.530 | Het.24 | / | H | H | / | / | CH$_3$ |
| Het-R.531 | Het.24 | / | CH$_3$ | H | / | / | CH$_3$ |
| Het-R.532 | Het.24 | / | H | CH$_3$ | / | / | CH$_3$ |
| Het-R.533 | Het.24 | / | CF$_3$ | H | / | / | CH$_3$ |
| Het-R.534 | Het.24 | / | H | CF$_3$ | / | / | CH$_3$ |
| Het-R.535 | Het.24 | / | Cl | H | / | / | CH$_3$ |
| Het-R.536 | Het.24 | / | H | Cl | / | / | CH$_3$ |
| Het-R.537 | Het.25 | H | / | / | / | / | / |
| Het-R.538 | Het.25 | CH$_3$ | / | / | / | / | / |
| Het-R.539 | Het.25 | CF$_3$ | / | / | / | / | / |
| Het-R.540 | Het.25 | Cl | / | / | / | / | / |
| Het-R.541 | Het.26 | H | / | / | / | / | / |
| Het-R.542 | Het.26 | CH$_3$ | / | / | / | / | / |
| Het-R.543 | Het.26 | CF$_3$ | / | / | / | / | / |
| Het-R.544 | Het.26 | Cl | / | / | / | / | / |
| Het-R.545 | Het.27 | H | / | / | / | / | / |
| Het-R.546 | Het.27 | CH$_3$ | / | / | / | / | / |
| Het-R.547 | Het.27 | CF$_3$ | / | / | / | / | / |
| Het-R.548 | Het.27 | Cl | / | / | / | / | / |
| Het-R.549 | Het.28 | H | / | / | / | / | / |
| Het-R.550 | Het.28 | CH$_3$ | / | / | / | / | / |
| Het-R.551 | Het.28 | CF$_3$ | / | / | / | / | / |
| Het-R.552 | Het.28 | Cl | / | / | / | / | / |
| Het-R.553 | Het.29 | H | / | / | / | / | / |
| Het-R.554 | Het.29 | CH$_3$ | / | / | / | / | / |
| Het-R.555 | Het.29 | CF$_3$ | / | / | / | / | / |
| Het-R.556 | Het.29 | Cl | / | / | / | / | / |
| Het-R.557 | Het.30 | H | / | / | / | / | / |
| Het-R.558 | Het.30 | CH$_3$ | / | / | / | / | / |
| Het-R.559 | Het.30 | CF$_3$ | / | / | / | / | / |
| Het-R.560 | Het.30 | Cl | / | / | / | / | / |
| Het-R.561 | Het.31 | H | / | / | / | / | H |
| Het-R.562 | Het.31 | CH$_3$ | / | / | / | / | H |
| Het-R.563 | Het.31 | CF$_3$ | / | / | / | / | H |
| Het-R.564 | Het.31 | Cl | / | / | / | / | H |
| Het-R.565 | Het.31 | H | / | / | / | / | CH$_3$ |
| Het-R.566 | Het.31 | CH$_3$ | / | / | / | / | CH$_3$ |
| Het-R.567 | Het.31 | CF$_3$ | / | / | / | / | CH$_3$ |
| Het-R.568 | Het.31 | Cl | / | / | / | / | CH$_3$ |
| Het-R.569 | Het.32 | H | / | / | / | / | H |
| Het-R.570 | Het.32 | CH$_3$ | / | / | / | / | H |
| Het-R.571 | Het.32 | CF$_3$ | / | / | / | / | H |
| Het-R.572 | Het.32 | Cl | / | / | / | / | H |
| Het-R.573 | Het.32 | H | / | / | / | / | CH$_3$ |
| Het-R.574 | Het.32 | CH$_3$ | / | / | / | / | CH$_3$ |
| Het-R.575 | Het.32 | CF$_3$ | / | / | / | / | CH$_3$ |
| Het-R.576 | Het.32 | Cl | / | / | / | / | CH$_3$ |
| Het-R.577 | Het.33 | H | / | / | / | / | H |
| Het-R.578 | Het.33 | CH$_3$ | / | / | / | / | H |
| Het-R.579 | Het.33 | CF$_3$ | / | / | / | / | H |
| Het-R.580 | Het.33 | Cl | / | / | / | / | H |
| Het-R.581 | Het.33 | H | / | / | / | / | CH$_3$ |
| Het-R.582 | Het.33 | CH$_3$ | / | / | / | / | CH$_3$ |
| Het-R.583 | Het.33 | CF$_3$ | / | / | / | / | CH$_3$ |
| Het-R.584 | Het.33 | Cl | / | / | / | / | CH$_3$ |
| Het-R.585 | Het.34 | H | / | / | / | / | H |
| Het-R.586 | Het.34 | CH$_3$ | / | / | / | / | H |
| Het-R.587 | Het.34 | CF$_3$ | / | / | / | / | H |
| Het-R.588 | Het.34 | Cl | / | / | / | / | H |
| Het-R.589 | Het.34 | H | / | / | / | / | CH$_3$ |
| Het-R.590 | Het.34 | CH$_3$ | / | / | / | / | CH$_3$ |
| Het-R.591 | Het.34 | CF$_3$ | / | / | / | / | CH$_3$ |
| Het-R.592 | Het.34 | Cl | / | / | / | / | CH$_3$ |
| Het-R.593 | Het.35 | / | H | / | / | / | H |
| Het-R.594 | Het.35 | / | CH$_3$ | / | / | / | H |
| Het-R.595 | Het.35 | / | CF$_3$ | / | / | / | H |
| Het-R.596 | Het.35 | / | Cl | / | / | / | H |
| Het-R.597 | Het.35 | / | H | / | / | / | CH$_3$ |
| Het-R.598 | Het.35 | / | CH$_3$ | / | / | / | CH$_3$ |
| Het-R.599 | Het.35 | / | CF$_3$ | / | / | / | CH$_3$ |
| Het-R.600 | Het.35 | / | Cl | / | / | / | CH$_3$ |
| Het-R.601 | Het.36 | / | / | / | / | / | H |
| Het-R.602 | Het.36 | / | / | / | / | / | CH$_3$ |
| Het-R.603 | Het.37 | H | / | / | / | / | / |
| Het-R.604 | Het.37 | CH$_3$ | / | / | / | / | / |
| Het-R.605 | Het.37 | CF$_3$ | / | / | / | / | / |
| Het-R.606 | Het.37 | Cl | / | / | / | / | / |
| Het-R.607 | Het.38 | / | H | / | / | / | / |
| Het-R.608 | Het.38 | / | CH$_3$ | / | / | / | / |
| Het-R.609 | Het.38 | / | CF$_3$ | / | / | / | / |
| Het-R.610 | Het.38 | / | Cl | / | / | / | / |
| Het-R.611 | Het.39 | H | / | / | / | / | / |
| Het-R.612 | Het.39 | CH$_3$ | / | / | / | / | / |
| Het-R.613 | Het.39 | CF$_3$ | / | / | / | / | / |
| Het-R.614 | Het.39 | Cl | / | / | / | / | / |
| Het-R.615 | Het.40 | / | H | / | / | / | / |
| Het-R.616 | Het.40 | / | CH$_3$ | / | / | / | / |
| Het-R.617 | Het.40 | / | CF$_3$ | / | / | / | / |
| Het-R.618 | Het.40 | / | Cl | / | / | / | / |
| Het-R.619 | Het.41 | H | H | H | H | / | / |
| Het-R.620 | Het.41 | CH$_3$ | H | H | H | / | / |
| Het-R.621 | Het.41 | H | CH$_3$ | H | H | / | / |
| Het-R.622 | Het.41 | H | H | CH$_3$ | H | / | / |
| Het-R.623 | Het.41 | H | H | H | CH$_3$ | / | / |
| Het-R.624 | Het.41 | CF$_3$ | H | H | H | / | / |

TABLE B-continued

| Radical | Het | $R^{8A}$ | $R^{8B}$ | $R^{8C}$ | $R^{8D}$ | $R^{8E}$ | $R^9$ |
|---|---|---|---|---|---|---|---|
| Het-R.625 | Het.41 | H | CF$_3$ | H | H | / | / |
| Het-R.626 | Het.41 | H | H | CF$_3$ | H | / | / |
| Het-R.627 | Het.41 | H | H | H | CF$_3$ | / | / |
| Het-R.628 | Het.41 | Cl | H | H | H | / | / |
| Het-R.629 | Het.41 | H | Cl | H | H | / | / |
| Het-R.630 | Het.41 | H | H | Cl | H | / | / |
| Het-R.631 | Het.41 | H | H | H | Cl | / | / |
| Het-R.632 | Het.41 | CH$_3$ | CH$_3$ | H | H | / | / |
| Het-R.633 | Het.41 | CH$_3$ | Cl | H | H | / | / |
| Het-R.634 | Het.41 | CH$_3$ | CF$_3$ | H | H | / | / |
| Het-R.635 | Het.41 | CH$_3$ | F | H | H | / | / |
| Het-R.636 | Het.41 | CF$_3$ | CH$_3$ | H | H | / | / |
| Het-R.637 | Het.41 | CF$_3$ | Cl | H | H | / | / |
| Het-R.638 | Het.41 | CF$_3$ | CF$_3$ | H | H | / | / |
| Het-R.639 | Het.41 | CF$_3$ | F | H | H | / | / |
| Het-R.640 | Het.41 | Cl | CH$_3$ | H | H | / | / |
| Het-R.641 | Het.41 | Cl | Cl | H | H | / | / |
| Het-R.642 | Het.41 | Cl | CF$_3$ | H | H | / | / |
| Het-R.643 | Het.41 | Cl | F | H | H | / | / |
| Het-R.644 | Het.41 | F | CH$_3$ | H | H | / | / |
| Het-R.645 | Het.41 | F | Cl | H | H | / | / |
| Het-R.646 | Het.41 | F | CF$_3$ | H | H | / | / |
| Het-R.647 | Het.41 | F | F | H | H | / | / |
| Het-R.648 | Het.41 | CH$_3$ | H | CH$_3$ | H | / | / |
| Het-R.649 | Het.41 | CH$_3$ | H | Cl | H | / | / |
| Het-R.650 | Het.41 | CH$_3$ | H | CF$_3$ | H | / | / |
| Het-R.651 | Het.41 | CH$_3$ | H | F | H | / | / |
| Het-R.652 | Het.41 | CF$_3$ | H | CH$_3$ | H | / | / |
| Het-R.653 | Het.41 | CF$_3$ | H | Cl | H | / | / |
| Het-R.654 | Het.41 | CF$_3$ | H | CF$_3$ | H | / | / |
| Het-R.655 | Het.41 | CF$_3$ | H | F | H | / | / |
| Het-R.656 | Het.41 | Cl | H | CH$_3$ | H | / | / |
| Het-R.657 | Het.41 | Cl | H | Cl | H | / | / |
| Het-R.658 | Het.41 | Cl | H | CF$_3$ | H | / | / |
| Het-R.659 | Het.41 | Cl | H | F | H | / | / |
| Het-R.660 | Het.41 | F | H | CH$_3$ | H | / | / |
| Het-R.661 | Het.41 | F | H | Cl | H | / | / |
| Het-R.662 | Het.41 | F | H | CF$_3$ | H | / | / |
| Het-R.663 | Het.41 | F | H | F | H | / | / |
| Het-R.664 | Het.41 | H | CH$_3$ | CH$_3$ | H | / | / |
| Het-R.665 | Het.41 | H | CH$_3$ | Cl | H | / | / |
| Het-R.666 | Het.41 | H | CH$_3$ | CF$_3$ | H | / | / |
| Het-R.667 | Het.41 | H | CH$_3$ | F | H | / | / |
| Het-R.668 | Het.41 | H | CF$_3$ | CH$_3$ | H | / | / |
| Het-R.669 | Het.41 | H | CF$_3$ | Cl | H | / | / |
| Het-R.670 | Het.41 | H | CF$_3$ | CF$_3$ | H | / | / |
| Het-R.671 | Het.41 | H | CF$_3$ | F | H | / | / |
| Het-R.672 | Het.41 | H | Cl | CH$_3$ | H | / | / |
| Het-R.673 | Het.41 | H | Cl | Cl | H | / | / |
| Het-R.674 | Het.41 | H | Cl | CF$_3$ | H | / | / |
| Het-R.675 | Het.41 | H | Cl | F | H | / | / |
| Het-R.676 | Het.41 | H | F | CH$_3$ | H | / | / |
| Het-R.677 | Het.41 | H | F | Cl | H | / | / |
| Het-R.678 | Het.41 | H | F | CF$_3$ | H | / | / |
| Het-R.679 | Het.41 | H | F | F | H | / | / |
| Het-R.680 | Het.41 | H | CH$_3$ | CH$_3$ | H | / | / |
| Het-R.681 | Het.41 | H | CH$_3$ | Cl | H | / | / |
| Het-R.682 | Het.41 | H | CH$_3$ | CF$_3$ | H | / | / |
| Het-R.683 | Het.41 | H | CH$_3$ | F | H | / | / |
| Het-R.684 | Het.41 | H | CF$_3$ | CH$_3$ | H | / | / |
| Het-R.685 | Het.41 | H | CF$_3$ | Cl | H | / | / |
| Het-R.686 | Het.41 | H | CF$_3$ | CF$_3$ | H | / | / |
| Het-R.687 | Het.41 | H | CF$_3$ | F | H | / | / |
| Het-R.688 | Het.41 | H | Cl | CH$_3$ | H | / | / |
| Het-R.689 | Het.41 | H | Cl | Cl | H | / | / |
| Het-R.690 | Het.41 | H | Cl | CF$_3$ | H | / | / |
| Het-R.691 | Het.41 | H | Cl | F | H | / | / |
| Het-R.692 | Het.41 | H | F | CH$_3$ | H | / | / |
| Het-R.693 | Het.41 | H | F | Cl | H | / | / |
| Het-R.694 | Het.41 | H | F | CF$_3$ | H | / | / |
| Het-R.695 | Het.41 | H | F | F | H | / | / |
| Het-R.696 | Het.41 | CH$_3$ | H | H | CH$_3$ | / | / |
| Het-R.697 | Het.41 | CH$_3$ | H | H | Cl | / | / |
| Het-R.698 | Het.41 | CH$_3$ | H | H | CF$_3$ | / | / |
| Het-R.699 | Het.41 | CH$_3$ | H | H | F | / | / |
| Het-R.700 | Het.41 | CF$_3$ | H | H | CH$_3$ | / | / |
| Het-R.701 | Het.41 | CF$_3$ | H | H | Cl | / | / |
| Het-R.702 | Het.41 | CF$_3$ | H | H | CF$_3$ | / | / |
| Het-R.703 | Het.41 | CF$_3$ | H | H | F | / | / |
| Het-R.704 | Het.41 | Cl | H | H | CH$_3$ | / | / |
| Het-R.705 | Het.41 | Cl | H | H | Cl | / | / |
| Het-R.706 | Het.41 | Cl | H | H | CF$_3$ | / | / |
| Het-R.707 | Het.41 | Cl | H | H | F | / | / |
| Het-R.708 | Het.41 | F | H | H | CH$_3$ | / | / |
| Het-R.709 | Het.41 | F | H | H | Cl | / | / |
| Het-R.710 | Het.41 | F | H | H | CF$_3$ | / | / |
| Het-R.711 | Het.41 | F | H | H | F | / | / |
| Het-R.712 | Het.41 | H | CH$_3$ | H | CH$_3$ | / | / |
| Het-R.713 | Het.41 | H | CH$_3$ | H | Cl | / | / |
| Het-R.714 | Het.41 | H | CH$_3$ | H | CF$_3$ | / | / |
| Het-R.715 | Het.41 | H | CH$_3$ | H | F | / | / |
| Het-R.716 | Het.41 | H | CF$_3$ | H | CH$_3$ | / | / |
| Het-R.717 | Het.41 | H | CF$_3$ | H | Cl | / | / |
| Het-R.718 | Het.41 | H | CF$_3$ | H | CF$_3$ | / | / |
| Het-R.719 | Het.41 | H | CF$_3$ | H | F | / | / |
| Het-R.720 | Het.41 | H | Cl | H | CH$_3$ | / | / |
| Het-R.721 | Het.41 | H | Cl | H | Cl | / | / |
| Het-R.722 | Het.41 | H | Cl | H | CF$_3$ | / | / |
| Het-R.723 | Het.41 | H | Cl | H | F | / | / |
| Het-R.724 | Het.41 | H | F | H | CH$_3$ | / | / |
| Het-R.725 | Het.41 | H | F | H | Cl | / | / |
| Het-R.726 | Het.41 | H | F | H | CF$_3$ | / | / |
| Het-R.727 | Het.41 | H | F | H | F | / | / |
| Het-R.728 | Het.42 | H | H | H | / | H | / |
| Het-R.729 | Het.42 | CH$_3$ | H | H | / | H | / |
| Het-R.730 | Het.42 | H | CH$_3$ | H | / | H | / |
| Het-R.731 | Het.42 | H | H | CH$_3$ | / | H | / |
| Het-R.732 | Het.42 | H | H | H | / | CH$_3$ | / |
| Het-R.733 | Het.42 | CF$_3$ | H | H | / | H | / |
| Het-R.734 | Het.42 | H | CF$_3$ | H | / | H | / |
| Het-R.735 | Het.42 | H | H | CF$_3$ | / | H | / |
| Het-R.736 | Het.42 | H | H | H | / | CF$_3$ | / |
| Het-R.737 | Het.42 | Cl | H | H | / | H | / |
| Het-R.738 | Het.42 | H | Cl | H | / | H | / |
| Het-R.739 | Het.42 | H | H | Cl | / | H | / |
| Het-R.740 | Het.42 | H | H | H | / | Cl | / |
| Het-R.741 | Het.42 | CH$_3$ | CH$_3$ | H | / | H | / |
| Het-R.742 | Het.42 | CH$_3$ | Cl | H | / | H | / |
| Het-R.743 | Het.42 | CH$_3$ | CF$_3$ | H | / | H | / |
| Het-R.744 | Het.42 | CH$_3$ | F | H | / | H | / |
| Het-R.745 | Het.42 | CF$_3$ | CH$_3$ | H | / | H | / |
| Het-R.746 | Het.42 | CF$_3$ | Cl | H | / | H | / |
| Het-R.747 | Het.42 | CF$_3$ | CF$_3$ | H | / | H | / |
| Het-R.748 | Het.42 | CF$_3$ | F | H | / | H | / |
| Het-R.749 | Het.42 | Cl | CH$_3$ | H | / | H | / |
| Het-R.750 | Het.42 | Cl | Cl | H | / | H | / |
| Het-R.751 | Het.42 | Cl | CF$_3$ | H | / | H | / |
| Het-R.752 | Het.42 | Cl | F | H | / | H | / |
| Het-R.753 | Het.42 | F | CH$_3$ | H | / | H | / |
| Het-R.754 | Het.42 | F | Cl | H | / | H | / |
| Het-R.755 | Het.42 | F | CF$_3$ | H | / | H | / |
| Het-R.756 | Het.42 | F | F | H | / | H | / |
| Het-R.757 | Het.42 | CH$_3$ | H | CH$_3$ | / | H | / |
| Het-R.758 | Het.42 | CH$_3$ | H | Cl | / | H | / |
| Het-R.759 | Het.42 | CH$_3$ | H | CF$_3$ | / | H | / |
| Het-R.760 | Het.42 | CH$_3$ | H | F | / | H | / |
| Het-R.761 | Het.42 | CF$_3$ | H | CH$_3$ | / | H | / |
| Het-R.762 | Het.42 | CF$_3$ | H | Cl | / | H | / |
| Het-R.763 | Het.42 | CF$_3$ | H | CF$_3$ | / | H | / |
| Het-R.764 | Het.42 | CF$_3$ | H | F | / | H | / |
| Het-R.765 | Het.42 | Cl | H | CH$_3$ | / | H | / |
| Het-R.766 | Het.42 | Cl | H | Cl | / | H | / |
| Het-R.767 | Het.42 | Cl | H | CF$_3$ | / | H | / |
| Het-R.768 | Het.42 | Cl | H | F | / | H | / |
| Het-R.769 | Het.42 | F | H | CH$_3$ | / | H | / |
| Het-R.770 | Het.42 | F | H | Cl | / | H | / |
| Het-R.771 | Het.42 | F | H | CF$_3$ | / | H | / |
| Het-R.772 | Het.42 | F | H | F | / | H | / |
| Het-R.773 | Het.42 | H | CH$_3$ | CH$_3$ | / | H | / |
| Het-R.774 | Het.42 | H | CH$_3$ | Cl | / | H | / |
| Het-R.775 | Het.42 | H | CH$_3$ | CF$_3$ | / | H | / |
| Het-R.776 | Het.42 | H | CH$_3$ | F | / | H | / |
| Het-R.777 | Het.42 | H | CF$_3$ | CH$_3$ | / | H | / |
| Het-R.778 | Het.42 | H | CF$_3$ | Cl | / | H | / |
| Het-R.779 | Het.42 | H | CF$_3$ | CF$_3$ | / | H | / |
| Het-R.780 | Het.42 | H | CF$_3$ | F | / | H | / |

TABLE B-continued

| Radical | Het | R$^{8A}$ | R$^{8B}$ | R$^{8C}$ | R$^{8D}$ | R$^{8E}$ | R$^9$ |
|---|---|---|---|---|---|---|---|
| Het-R.781 | Het.42 | H | Cl | CH$_3$ | / | H | / |
| Het-R.782 | Het.42 | H | Cl | Cl | / | H | / |
| Het-R.783 | Het.42 | H | Cl | CF$_3$ | / | H | / |
| Het-R.784 | Het.42 | H | Cl | F | / | H | / |
| Het-R.785 | Het.42 | H | F | CH$_3$ | / | H | / |
| Het-R.786 | Het.42 | H | F | Cl | / | H | / |
| Het-R.787 | Het.42 | H | F | CF$_3$ | / | H | / |
| Het-R.788 | Het.42 | H | F | F | / | H | / |
| Het-R.789 | Het.42 | H | CH$_3$ | H | / | CH$_3$ | / |
| Het-R.790 | Het.42 | H | CH$_3$ | H | / | Cl | / |
| Het-R.791 | Het.42 | H | CH$_3$ | H | / | CF$_3$ | / |
| Het-R.792 | Het.42 | H | CH$_3$ | H | / | F | / |
| Het-R.793 | Het.42 | H | CF$_3$ | H | / | CH$_3$ | / |
| Het-R.794 | Het.42 | H | CF$_3$ | H | / | Cl | / |
| Het-R.795 | Het.42 | H | CF$_3$ | H | / | CF$_3$ | / |
| Het-R.796 | Het.42 | H | CF$_3$ | H | / | F | / |
| Het-R.797 | Het.42 | H | Cl | H | / | CH$_3$ | / |
| Het-R.798 | Het.42 | H | Cl | H | / | Cl | / |
| Het-R.799 | Het.42 | H | Cl | H | / | CF$_3$ | / |
| Het-R.800 | Het.42 | H | Cl | H | / | F | / |
| Het-R.801 | Het.42 | H | F | H | / | CH$_3$ | / |
| Het-R.802 | Het.42 | H | F | H | / | Cl | / |
| Het-R.803 | Het.42 | H | F | H | / | CF$_3$ | / |
| Het-R.804 | Het.42 | H | F | H | / | F | / |
| Het-R.805 | Het.43 | H | H | / | H | H | / |
| Het-R.806 | Het.43 | CH$_3$ | H | / | H | H | / |
| Het-R.807 | Het.43 | H | CH$_3$ | / | H | H | / |
| Het-R.808 | Het.43 | H | H | / | CH$_3$ | H | / |
| Het-R.809 | Het.43 | H | H | / | H | CH$_3$ | / |
| Het-R.810 | Het.43 | CF$_3$ | H | / | H | H | / |
| Het-R.811 | Het.43 | H | CF$_3$ | / | H | H | / |
| Het-R.812 | Het.43 | H | H | / | CF$_3$ | H | / |
| Het-R.813 | Het.43 | H | H | / | H | CF$_3$ | / |
| Het-R.814 | Het.43 | Cl | H | / | H | H | / |
| Het-R.815 | Het.43 | H | Cl | / | H | H | / |
| Het-R.816 | Het.43 | H | H | / | Cl | H | / |
| Het-R.817 | Het.43 | H | H | / | H | Cl | / |
| Het-R.818 | Het.43 | CH$_3$ | CH$_3$ | / | H | H | / |
| Het-R.819 | Het.43 | CH$_3$ | Cl | / | H | H | / |
| Het-R.820 | Het.43 | CH$_3$ | CF$_3$ | / | H | H | / |
| Het-R.821 | Het.43 | CH$_3$ | F | / | H | H | / |
| Het-R.822 | Het.43 | Cl | CH$_3$ | / | H | H | / |
| Het-R.823 | Het.43 | Cl | Cl | / | H | H | / |
| Het-R.824 | Het.43 | Cl | CF$_3$ | / | H | H | / |
| Het-R.825 | Het.43 | Cl | F | / | H | H | / |
| Het-R.826 | Het.43 | CF$_3$ | CH$_3$ | / | H | H | / |
| Het-R.827 | Het.43 | CF$_3$ | Cl | / | H | H | / |
| Het-R.828 | Het.43 | CF$_3$ | CF$_3$ | / | H | H | / |
| Het-R.829 | Het.43 | CF$_3$ | F | / | H | H | / |
| Het-R.830 | Het.43 | F | CH$_3$ | / | H | H | / |
| Het-R.831 | Het.43 | F | Cl | / | H | H | / |
| Het-R.832 | Het.43 | F | CF$_3$ | / | H | H | / |
| Het-R.833 | Het.43 | F | F | / | H | H | / |
| Het-R.834 | Het.43 | CH$_3$ | H | / | CH$_3$ | H | / |
| Het-R.835 | Het.43 | CH$_3$ | H | / | Cl | H | / |
| Het-R.836 | Het.43 | CH$_3$ | H | / | CF$_3$ | H | / |
| Het-R.837 | Het.43 | CH$_3$ | H | / | F | H | / |
| Het-R.838 | Het.43 | Cl | H | / | CH$_3$ | H | / |
| Het-R.839 | Het.43 | Cl | H | / | Cl | H | / |
| Het-R.840 | Het.43 | Cl | H | / | CF$_3$ | H | / |
| Het-R.841 | Het.43 | Cl | H | / | F | H | / |
| Het-R.842 | Het.43 | CF$_3$ | H | / | CH$_3$ | H | / |
| Het-R.843 | Het.43 | CF$_3$ | H | / | Cl | H | / |
| Het-R.844 | Het.43 | CF$_3$ | H | / | CF$_3$ | H | / |
| Het-R.845 | Het.43 | CF$_3$ | H | / | F | H | / |
| Het-R.846 | Het.43 | F | H | / | CH$_3$ | H | / |
| Het-R.847 | Het.43 | F | H | / | Cl | H | / |
| Het-R.848 | Het.43 | F | H | / | CF$_3$ | H | / |
| Het-R.849 | Het.43 | F | H | / | F | H | / |
| Het-R.850 | Het.43 | H | CH$_3$ | / | CH$_3$ | H | / |
| Het-R.851 | Het.43 | H | CH$_3$ | / | Cl | H | / |
| Het-R.852 | Het.43 | H | CH$_3$ | / | CF$_3$ | H | / |
| Het-R.853 | Het.43 | H | CH$_3$ | / | F | H | / |
| Het-R.854 | Het.43 | H | Cl | / | CH$_3$ | H | / |
| Het-R.855 | Het.43 | H | Cl | / | Cl | H | / |
| Het-R.856 | Het.43 | H | Cl | / | CF$_3$ | H | / |
| Het-R.857 | Het.43 | H | Cl | / | F | H | / |
| Het-R.858 | Het.43 | H | CF$_3$ | / | CH$_3$ | H | / |
| Het-R.859 | Het.43 | H | CF$_3$ | / | Cl | H | / |
| Het-R.860 | Het.43 | H | CF$_3$ | / | CF$_3$ | H | / |
| Het-R.861 | Het.43 | H | CF$_3$ | / | F | H | / |
| Het-R.862 | Het.43 | H | F | / | CH$_3$ | H | / |
| Het-R.863 | Het.43 | H | F | / | Cl | H | / |
| Het-R.864 | Het.43 | H | F | / | CF$_3$ | H | / |
| Het-R.865 | Het.43 | H | F | / | F | H | / |
| Het-R.866 | Het.43 | H | CH$_3$ | / | H | CH$_3$ | / |
| Het-R.867 | Het.43 | H | CH$_3$ | / | H | Cl | / |
| Het-R.868 | Het.43 | H | CH$_3$ | / | H | CF$_3$ | / |
| Het-R.869 | Het.43 | H | CH$_3$ | / | H | F | / |
| Het-R.870 | Het.43 | H | Cl | / | H | CH$_3$ | / |
| Het-R.871 | Het.43 | H | Cl | / | H | Cl | / |
| Het-R.872 | Het.43 | H | Cl | / | H | CF$_3$ | / |
| Het-R.873 | Het.43 | H | Cl | / | H | F | / |
| Het-R.874 | Het.43 | H | CF$_3$ | / | H | CH$_3$ | / |
| Het-R.875 | Het.43 | H | CF$_3$ | / | H | Cl | / |
| Het-R.876 | Het.43 | H | CF$_3$ | / | H | CF$_3$ | / |
| Het-R.877 | Het.43 | H | CF$_3$ | / | H | F | / |
| Het-R.878 | Het.43 | H | F | / | H | CH$_3$ | / |
| Het-R.879 | Het.43 | H | F | / | H | Cl | / |
| Het-R.880 | Het.43 | H | F | / | H | CF$_3$ | / |
| Het-R.881 | Het.43 | H | F | / | H | F | / |
| Het-R.882 | Het.43 | H | H | / | CH$_3$ | CH$_3$ | / |
| Het-R.883 | Het.43 | H | H | / | CH$_3$ | Cl | / |
| Het-R.884 | Het.43 | H | H | / | CH$_3$ | CF$_3$ | / |
| Het-R.885 | Het.43 | H | H | / | CH$_3$ | F | / |
| Het-R.886 | Het.43 | H | H | / | Cl | CH$_3$ | / |
| Het-R.887 | Het.43 | H | H | / | Cl | Cl | / |
| Het-R.888 | Het.43 | H | H | / | Cl | CF$_3$ | / |
| Het-R.889 | Het.43 | H | H | / | Cl | F | / |
| Het-R.890 | Het.43 | H | H | / | CF$_3$ | CH$_3$ | / |
| Het-R.891 | Het.43 | H | H | / | CF$_3$ | Cl | / |
| Het-R.892 | Het.43 | H | H | / | CF$_3$ | CF$_3$ | / |
| Het-R.893 | Het.43 | H | H | / | CF$_3$ | F | / |
| Het-R.894 | Het.43 | H | H | / | F | CH$_3$ | / |
| Het-R.895 | Het.43 | H | H | / | F | Cl | / |
| Het-R.896 | Het.43 | H | H | / | F | CF$_3$ | / |
| Het-R.897 | Het.43 | H | H | / | F | F | / |
| Het-R.898 | Het.44 | H | H | H | H | / | / |
| Het-R.899 | Het.44 | CH$_3$ | H | H | H | / | / |
| Het-R.900 | Het.44 | H | CH$_3$ | H | H | / | / |
| Het-R.901 | Het.44 | H | H | CH$_3$ | H | / | / |
| Het-R.902 | Het.44 | H | H | H | CH$_3$ | / | / |
| Het-R.903 | Het.44 | CF$_3$ | H | H | H | / | / |
| Het-R.904 | Het.44 | H | CF$_3$ | H | H | / | / |
| Het-R.905 | Het.44 | H | H | CF$_3$ | H | / | / |
| Het-R.906 | Het.44 | H | H | H | CF$_3$ | / | / |
| Het-R.907 | Het.44 | Cl | H | H | H | / | / |
| Het-R.908 | Het.44 | H | Cl | H | H | / | / |
| Het-R.909 | Het.44 | H | H | Cl | H | / | / |
| Het-R.910 | Het.44 | H | H | H | Cl | / | / |
| Het-R.911 | Het.45 | H | H | H | / | H | / |
| Het-R.912 | Het.45 | CH$_3$ | H | H | / | H | / |
| Het-R.913 | Het.45 | H | CH$_3$ | H | / | H | / |
| Het-R.914 | Het.45 | H | H | CH$_3$ | / | H | / |
| Het-R.915 | Het.45 | H | H | H | / | CH$_3$ | / |
| Het-R.916 | Het.45 | CF$_3$ | H | H | / | H | / |
| Het-R.917 | Het.45 | H | CF$_3$ | H | / | H | / |
| Het-R.918 | Het.45 | H | H | CF$_3$ | / | H | / |
| Het-R.919 | Het.45 | H | H | H | / | CF$_3$ | / |
| Het-R.920 | Het.45 | Cl | H | H | / | H | / |
| Het-R.921 | Het.45 | H | Cl | H | / | H | / |
| Het-R.922 | Het.45 | H | H | Cl | / | H | / |
| Het-R.923 | Het.45 | H | H | H | / | Cl | / |
| Het-R.924 | Het.46 | H | H | / | H | H | / |
| Het-R.925 | Het.46 | CH$_3$ | H | / | H | H | / |
| Het-R.926 | Het.46 | H | CH$_3$ | / | H | H | / |
| Het-R.927 | Het.46 | H | H | / | CH$_3$ | H | / |
| Het-R.928 | Het.46 | H | H | / | H | CH$_3$ | / |
| Het-R.929 | Het.46 | CF$_3$ | H | / | H | H | / |
| Het-R.930 | Het.46 | H | CF$_3$ | / | H | H | / |
| Het-R.931 | Het.46 | H | H | / | CF$_3$ | H | / |
| Het-R.932 | Het.46 | H | H | / | H | CF$_3$ | / |
| Het-R.933 | Het.46 | Cl | H | / | H | H | / |
| Het-R.934 | Het.46 | H | Cl | / | H | H | / |
| Het-R.935 | Het.46 | H | H | / | Cl | H | / |
| Het-R.936 | Het.46 | H | H | / | H | Cl | / |

TABLE B-continued

| Radical | Het | R$^{8A}$ | R$^{8B}$ | R$^{8C}$ | R$^{8D}$ | R$^{8E}$ | R$^9$ |
|---|---|---|---|---|---|---|---|
| Het-R.937 | Het.47 | H | H | H | / | / | / |
| Het-R.938 | Het.47 | CH$_3$ | H | H | / | / | / |
| Het-R.939 | Het.47 | H | CH$_3$ | H | / | / | / |
| Het-R.940 | Het.47 | H | H | CH$_3$ | / | / | / |
| Het-R.941 | Het.47 | CF$_3$ | H | H | / | / | / |
| Het-R.942 | Het.47 | H | CF$_3$ | H | / | / | / |
| Het-R.943 | Het.47 | H | H | CF$_3$ | / | / | / |
| Het-R.944 | Het.47 | Cl | H | H | / | / | / |
| Het-R.945 | Het.47 | H | Cl | H | / | / | / |
| Het-R.946 | Het.47 | H | H | Cl | / | / | / |
| Het-R.947 | Het.48 | H | H | / | H | / | / |
| Het-R.948 | Het.48 | CH$_3$ | H | / | H | / | / |
| Het-R.949 | Het.48 | H | CH$_3$ | / | H | / | / |
| Het-R.950 | Het.48 | H | H | / | CH$_3$ | / | / |
| Het-R.951 | Het.48 | CF$_3$ | H | / | H | / | / |
| Het-R.952 | Het.48 | H | CF$_3$ | / | H | / | / |
| Het-R.953 | Het.48 | H | H | / | CF$_3$ | / | / |
| Het-R.954 | Het.48 | Cl | H | / | H | / | / |
| Het-R.955 | Het.48 | H | Cl | / | H | / | / |
| Het-R.956 | Het.48 | H | H | / | Cl | / | / |
| Het-R.957 | Het.49 | H | H | H | / | / | / |
| Het-R.958 | Het.49 | CH$_3$ | H | H | / | / | / |
| Het-R.959 | Het.49 | H | CH$_3$ | H | / | / | / |
| Het-R.960 | Het.49 | H | H | CH$_3$ | / | / | / |
| Het-R.961 | Het.49 | CF$_3$ | H | H | / | / | / |
| Het-R.962 | Het.49 | H | CF$_3$ | H | / | / | / |
| Het-R.963 | Het.49 | H | H | CF$_3$ | / | / | / |
| Het-R.964 | Het.49 | Cl | H | H | / | / | / |
| Het-R.965 | Het.49 | H | Cl | H | / | / | / |
| Het-R.966 | Het.49 | H | H | Cl | / | / | / |
| Het-R.967 | Het.50 | H | H | / | / | H | / |
| Het-R.968 | Het.50 | CH$_3$ | H | / | / | H | / |
| Het-R.969 | Het.50 | H | CH$_3$ | / | / | H | / |
| Het-R.970 | Het.50 | H | H | / | / | CH$_3$ | / |
| Het-R.971 | Het.50 | CF$_3$ | H | / | / | H | / |
| Het-R.972 | Het.50 | H | CF$_3$ | / | / | H | / |
| Het-R.973 | Het.50 | H | H | / | / | CF$_3$ | / |
| Het-R.974 | Het.50 | Cl | H | / | / | H | / |
| Het-R.975 | Het.50 | H | Cl | / | / | H | / |
| Het-R.976 | Het.50 | H | H | / | / | Cl | / |
| Het-R.977 | Het.51 | H | / | H | / | H | / |
| Het-R.978 | Het.51 | CH$_3$ | / | H | / | H | / |
| Het-R.979 | Het.51 | H | / | CH$_3$ | / | H | / |
| Het-R.980 | Het.51 | H | / | H | / | CH$_3$ | / |
| Het-R.981 | Het.51 | CF$_3$ | / | H | / | H | / |
| Het-R.982 | Het.51 | H | / | CF$_3$ | / | H | / |
| Het-R.983 | Het.51 | H | / | H | / | CF$_3$ | / |
| Het-R.984 | Het.51 | Cl | / | H | / | H | / |
| Het-R.985 | Het.51 | H | / | Cl | / | H | / |
| Het-R.986 | Het.51 | H | / | H | / | Cl | / |
| Het-R.987 | Het.52 | H | H | / | H | / | / |
| Het-R.988 | Het.52 | CH$_3$ | H | / | H | / | / |
| Het-R.989 | Het.52 | H | CH$_3$ | / | H | / | / |
| Het-R.990 | Het.52 | H | H | / | CH$_3$ | / | / |
| Het-R.991 | Het.52 | CF$_3$ | H | / | H | / | / |
| Het-R.992 | Het.52 | H | CF$_3$ | / | H | / | / |
| Het-R.993 | Het.52 | H | H | / | CF$_3$ | / | / |
| Het-R.994 | Het.52 | Cl | H | / | H | / | / |
| Het-R.995 | Het.52 | H | Cl | / | H | / | / |
| Het-R.996 | Het.52 | H | H | / | Cl | / | / |
| Het-R.997 | Het.53 | H | / | H | / | / | / |
| Het-R.998 | Het.53 | CH$_3$ | / | H | / | / | / |
| Het-R.999 | Het.53 | H | / | CH$_3$ | / | / | / |
| Het-R.1000 | Het.53 | CF$_3$ | / | H | / | / | / |
| Het-R.1001 | Het.53 | H | / | CF$_3$ | / | / | / |
| Het-R.1002 | Het.53 | Cl | / | H | / | / | / |
| Het-R.1003 | Het.53 | H | / | Cl | / | / | / |
| Het-R.1004 | Het.54 | H | H | / | / | / | / |
| Het-R.1005 | Het.54 | H | CH$_3$ | / | / | / | / |
| Het-R.1006 | Het.54 | CH$_3$ | H | / | / | / | / |
| Het-R.1007 | Het.54 | H | CF$_3$ | / | / | / | / |
| Het-R.1008 | Het.54 | CF$_3$ | H | / | / | / | / |
| Het-R.1009 | Het.54 | H | Cl | / | / | / | / |
| Het-R.1010 | Het.54 | Cl | H | / | / | / | / |
| Het-R.1011 | Het.55 | H | / | / | / | H | / |
| Het-R.1012 | Het.55 | CH$_3$ | / | / | / | H | / |
| Het-R.1013 | Het.55 | H | / | / | / | CH$_3$ | / |
| Het-R.1014 | Het.55 | CF$_3$ | / | / | / | H | / |
| Het-R.1015 | Het.55 | H | / | / | / | CF$_3$ | / |
| Het-R.1016 | Het.55 | Cl | / | / | / | H | / |
| Het-R.1017 | Het.55 | H | / | / | / | Cl | / |
| Het-R.1018 | Het.56 | / | H | / | / | H | / |
| Het-R.1019 | Het.56 | / | CH$_3$ | / | / | H | / |
| Het-R.1020 | Het.56 | / | H | / | / | CH$_3$ | / |
| Het-R.1021 | Het.56 | / | CF$_3$ | / | / | H | / |
| Het-R.1022 | Het.56 | / | H | / | / | CF$_3$ | / |
| Het-R.1023 | Het.56 | / | Cl | / | / | H | / |
| Het-R.1024 | Het.56 | / | H | / | / | Cl | / |
| Het-R.1025 | Het.57 | H | / | / | / | / | / |
| Het-R.1026 | Het.57 | CH$_3$ | / | / | / | / | / |
| Het-R.1027 | Het.57 | CF$_3$ | / | / | / | / | / |
| Het-R.1028 | Het.57 | Cl | / | / | / | / | / |

Apart from that, R$^a$ and R$^b$ are, independently of each other, preferably selected from hydrogen and C$_1$-C$_6$-alkyl.

Y is preferably a single bond, O, S or methylen.

Ar' is preferably phenyl or a 5- or 6-membered monocyclic heteroaromatic ring.

Cy is preferably cyclohexyl.

Particular preference is given to those compounds I, wherein
R$^1$, R$^2$, R$^3$ are hydrogen;
A is A$^2$ wherein R$^{4a}$, R$^{4b}$, R$^{4c}$, R$^d$ are hydrogen and X is sulfur; and
R$^6$ is hydrogen.

Particular preference is also given to those compounds I, wherein
R$^1$, R$^2$, R$^3$ are hydrogen;
A is A$^2$ wherein R$^{4a}$, R$^{4b}$, R$^{4c}$, R$^d$ are hydrogen and X is O; and
R$^6$ is hydrogen.

Particular preference is also given to those compounds I, wherein
R$^1$, R$^2$, R$^3$ are hydrogen;
A is A$^2$ wherein R$^{4a}$, R$^{4b}$, R$^{4c}$, R$^d$ are hydrogen and X is NH; and
R$^6$ is hydrogen.

Particular preference is also given to those compounds I, wherein
R$^1$, R$^2$, R$^3$ are hydrogen;
A is A$^2$ wherein R$^{4a}$, R$^{4b}$, R$^{4c}$, R$^d$ are hydrogen and X is N—CH$_3$; and
R$^6$ is hydrogen.

Particular preference is also given to those compounds I, wherein
R$^1$, R$^2$, R$^3$ are hydrogen;
A is A$^2$ wherein R$^{4a}$, R$^{4b}$, R$^{4c}$, R$^d$ are hydrogen and X is N—C(O)CH$_3$; and
R$^6$ is hydrogen.

Examples of preferred compounds I, wherein R$^1$, R$^2$, R$^3$ are hydrogen, A is a radical A$^2$ with R$^{4a}$, R$^{4b}$, R$^{4c}$ and R$^{4d}$ being hydrogen, X=S and R$^6$ is hydrogen, are described in the following tables 1 to 205 (hereinafter also referred to as compounds Ia).

Table 1: Compounds of the formula Ia, wherein Ar=Ar-1 as defined in table A, and Het for a compound corresponds in each case to one row of table B.

Table 2: Compounds of the formula Ia, wherein Ar=Ar-2 as defined in table A, and Het for a compound corresponds in each case to one row of table B.

Table 3: Compounds of the formula Ia, wherein Ar=Ar-3 as defined in table A, and Het for a compound corresponds in each case to one row of table B.

Table 4: Compounds of the formula Ia, wherein Ar=Ar-4 as defined in table A, and Het for a compound corresponds in each case to one row of table B.

Table 5: Compounds of the formula Ia, wherein Ar=Ar-5 as defined in table A, and Het for a compound corresponds in each case to one row of table B.

Table 6: Compounds of the formula Ia, wherein Ar=Ar-6 as defined in table A, and Het for a compound corresponds in each case to one row of table B.

Table 7: Compounds of the formula Ia, wherein Ar=Ar-7 as defined in table A, and Het for a compound corresponds in each case to one row of table B.

Table 8: Compounds of the formula Ia, wherein Ar=Ar-8 as defined in table A, and Het for a compound corresponds in each case to one row of table B.

Table 9: Compounds of the formula Ia, wherein Ar=Ar-9 as defined in table A, and Het for a compound corresponds in each case to one row of table B.

Table 10: Compounds of the formula Ia, wherein Ar=Ar-10 as defined in table A, and Het for a compound corresponds in each case to one row of table B.

Table 11: Compounds of the formula Ia, wherein Ar=Ar-11 as defined in table A, and Het for a compound corresponds in each case to one row of table B.

Table 12: Compounds of the formula Ia, wherein Ar=Ar-12 as defined in table A, and Het for a compound corresponds in each case to one row of table B.

Table 13: Compounds of the formula Ia, wherein Ar=Ar-13 as defined in table A, and Het for a compound corresponds in each case to one row of table B.

Table 14: Compounds of the formula Ia, wherein Ar=Ar-14 as defined in table A, and Het for a compound corresponds in each case to one row of table B.

Table 15: Compounds of the formula Ia, wherein Ar=Ar-15 as defined in table A, and Het for a compound corresponds in each case to one row of table B.

Table 16: Compounds of the formula Ia, wherein Ar=Ar-16 as defined in table A, and Het for a compound corresponds in each case to one row of table B.

Table 17: Compounds of the formula Ia, wherein Ar=Ar-17 as defined in table A, and Het for a compound corresponds in each case to one row of table B.

Table 18: Compounds of the formula Ia, wherein Ar=Ar-18 as defined in table A, and Het for a compound corresponds in each case to one row of table B.

Table 19: Compounds of the formula Ia, wherein Ar=Ar-19 as defined in table A, and Het for a compound corresponds in each case to one row of table B.

Table 20: Compounds of the formula Ia, wherein Ar=Ar-20 as defined in table A, and Het for a compound corresponds in each case to one row of table B.

Table 21: Compounds of the formula Ia, wherein Ar=Ar-21 as defined in table A, and Het for a compound corresponds in each case to one row of table B.

Table 22: Compounds of the formula Ia, wherein Ar=Ar-22 as defined in table A, and Het for a compound corresponds in each case to one row of table B.

Table 23: Compounds of the formula Ia, wherein Ar=Ar-23 as defined in table A, and Het for a compound corresponds in each case to one row of table B.

Table 24: Compounds of the formula Ia, wherein Ar=Ar-24 as defined in table A, and Het for a compound corresponds in each case to one row of table B.

Table 25: Compounds of the formula Ia, wherein Ar=Ar-25 as defined in table A, and Het for a compound corresponds in each case to one row of table B.

Table 26: Compounds of the formula Ia, wherein Ar=Ar-26 as defined in table A, and Het for a compound corresponds in each case to one row of table B.

Table 27: Compounds of the formula Ia, wherein Ar=Ar-27 as defined in table A, and Het for a compound corresponds in each case to one row of table B.

Table 28: Compounds of the formula Ia, wherein Ar=Ar-28 as defined in table A, and Het for a compound corresponds in each case to one row of table B.

Table 29: Compounds of the formula Ia, wherein Ar=Ar-29 as defined in table A, and Het for a compound corresponds in each case to one row of table B.

Table 30: Compounds of the formula Ia, wherein Ar=Ar-30 as defined in table A, and Het for a compound corresponds in each case to one row of table B.

Table 31: Compounds of the formula Ia, wherein Ar=Ar-31 as defined in table A, and Het for a compound corresponds in each case to one row of table B.

Table 32: Compounds of the formula Ia, wherein Ar=Ar-32 as defined in table A, and Het for a compound corresponds in each case to one row of table B.

Table 33: Compounds of the formula Ia, wherein Ar=Ar-33 as defined in table A, and Het for a compound corresponds in each case to one row of table B.

Table 34: Compounds of the formula Ia, wherein Ar=Ar-34 as defined in table A, and Het for a compound corresponds in each case to one row of table B.

Table 35: Compounds of the formula Ia, wherein Ar=Ar-35 as defined in table A, and Het for a compound corresponds in each case to one row of table B.

Table 36: Compounds of the formula Ia, wherein Ar=Ar-36 as defined in table A, and Het for a compound corresponds in each case to one row of table B.

Table 37: Compounds of the formula Ia, wherein Ar=Ar-37 as defined in table A, and Het for a compound corresponds in each case to one row of table B.

Table 38: Compounds of the formula Ia, wherein Ar=Ar-38 as defined in table A, and Het for a compound corresponds in each case to one row of table B.

Table 39: Compounds of the formula Ia, wherein Ar=Ar-39 as defined in table A, and Het for a compound corresponds in each case to one row of table B.

Table 40: Compounds of the formula Ia, wherein Ar=Ar-40 as defined in table A, and Het for a compound corresponds in each case to one row of table B.

Table 41: Compounds of the formula Ia, wherein Ar=Ar-41 as defined in table A, and Het for a compound corresponds in each case to one row of table B.

Table 42: Compounds of the formula Ia, wherein Ar=Ar-42 as defined in table A, and Het for a compound corresponds in each case to one row of table B.

Table 43: Compounds of the formula Ia, wherein Ar=Ar-43 as defined in table A, and Het for a compound corresponds in each case to one row of table B.

Table 44: Compounds of the formula Ia, wherein Ar=Ar-44 as defined in table A, and Het for a compound corresponds in each case to one row of table B.

Table 45: Compounds of the formula Ia, wherein Ar=Ar-45 as defined in table A, and Het for a compound corresponds in each case to one row of table B.

Table 46: Compounds of the formula Ia, wherein Ar=Ar-46 as defined in table A, and Het for a compound corresponds in each case to one row of table B.

Table 47: Compounds of the formula Ia, wherein Ar=Ar-47 as defined in table A, and Het for a compound corresponds in each case to one row of table B.

Table 48: Compounds of the formula Ia, wherein Ar=Ar-48 as defined in table A, and Het for a compound corresponds in each case to one row of table B.

Table 49: Compounds of the formula Ia, wherein Ar=Ar-49 as defined in table A, and Het for a compound corresponds in each case to one row of table B.

Table 50: Compounds of the formula Ia, wherein Ar=Ar-50 as defined in table A, and Het for a compound corresponds in each case to one row of table B.

Table 51: Compounds of the formula Ia, wherein Ar=Ar-51 as defined in table A, and Het for a compound corresponds in each case to one row of table B.

Table 52: Compounds of the formula Ia, wherein Ar=Ar-52 as defined in table A, and Het for a compound corresponds in each case to one row of table B.

Table 53: Compounds of the formula Ia, wherein Ar=Ar-53 as defined in table A, and Het for a compound corresponds in each case to one row of table B.

Table 54: Compounds of the formula Ia, wherein Ar=Ar-54 as defined in table A, and Het for a compound corresponds in each case to one row of table B.

Table 55: Compounds of the formula Ia, wherein Ar=Ar-55 as defined in table A, and Het for a compound corresponds in each case to one row of table B.

Table 56: Compounds of the formula Ia, wherein Ar=Ar-56 as defined in table A, and Het for a compound corresponds in each case to one row of table B.

Table 57: Compounds of the formula Ia, wherein Ar=Ar-57 as defined in table A, and Het for a compound corresponds in each case to one row of table B.

Table 58: Compounds of the formula Ia, wherein Ar=Ar-58 as defined in table A, and Het for a compound corresponds in each case to one row of table B.

Table 59: Compounds of the formula Ia, wherein Ar=Ar-59 as defined in table A, and Het for a compound corresponds in each case to one row of table B.

Table 60: Compounds of the formula Ia, wherein Ar=Ar-60 as defined in table A, and Het for a compound corresponds in each case to one row of table B.

Table 61: Compounds of the formula Ia, wherein Ar=Ar-61 as defined in table A, and Het for a compound corresponds in each case to one row of table B.

Table 62: Compounds of the formula Ia, wherein Ar=Ar-62 as defined in table A, and Het for a compound corresponds in each case to one row of table B.

Table 63: Compounds of the formula Ia, wherein Ar=Ar-63 as defined in table A, and Het for a compound corresponds in each case to one row of table B.

Table 64: Compounds of the formula Ia, wherein Ar=Ar-64 as defined in table A, and Het for a compound corresponds in each case to one row of table B.

Table 65: Compounds of the formula Ia, wherein Ar=Ar-65 as defined in table A, and Het for a compound corresponds in each case to one row of table B.

Table 66: Compounds of the formula Ia, wherein Ar=Ar-66 as defined in table A, and Het for a compound corresponds in each case to one row of table B.

Table 67: Compounds of the formula Ia, wherein Ar=Ar-67 as defined in table A, and Het for a compound corresponds in each case to one row of table B.

Table 68: Compounds of the formula Ia, wherein Ar=Ar-68 as defined in table A, and Het for a compound corresponds in each case to one row of table B.

Table 69: Compounds of the formula Ia, wherein Ar=Ar-69 as defined in table A, and Het for a compound corresponds in each case to one row of table B.

Table 70: Compounds of the formula Ia, wherein Ar=Ar-70 as defined in table A, and Het for a compound corresponds in each case to one row of table B.

Table 71: Compounds of the formula Ia, wherein Ar=Ar-71 as defined in table A, and Het for a compound corresponds in each case to one row of table B.

Table 72: Compounds of the formula Ia, wherein Ar=Ar-72 as defined in table A, and Het for a compound corresponds in each case to one row of table B.

Table 73: Compounds of the formula Ia, wherein Ar=Ar-73 as defined in table A, and Het for a compound corresponds in each case to one row of table B.

Table 74: Compounds of the formula Ia, wherein Ar=Ar-74 as defined in table A, and Het for a compound corresponds in each case to one row of table B.

Table 75: Compounds of the formula Ia, wherein Ar=Ar-75 as defined in table A, and Het for a compound corresponds in each case to one row of table B.

Table 76: Compounds of the formula Ia, wherein Ar=Ar-76 as defined in table A, and Het for a compound corresponds in each case to one row of table B.

Table 77: Compounds of the formula Ia, wherein Ar=Ar-77 as defined in table A, and Het for a compound corresponds in each case to one row of table B.

Table 78: Compounds of the formula Ia, wherein Ar=Ar-78 as defined in table A, and Het for a compound corresponds in each case to one row of table B.

Table 79: Compounds of the formula Ia, wherein Ar=Ar-79 as defined in table A, and Het for a compound corresponds in each case to one row of table B.

Table 80: Compounds of the formula Ia, wherein Ar=Ar-80 as defined in table A, and Het for a compound corresponds in each case to one row of table B.

Table 81: Compounds of the formula Ia, wherein Ar=Ar-81 as defined in table A, and Het for a compound corresponds in each case to one row of table B.

Table 82: Compounds of the formula Ia, wherein Ar=Ar-82 as defined in table A, and Het for a compound corresponds in each case to one row of table B.

Table 83: Compounds of the formula Ia, wherein Ar=Ar-83 as defined in table A, and Het for a compound corresponds in each case to one row of table B.

Table 84: Compounds of the formula Ia, wherein Ar=Ar-84 as defined in table A, and Het for a compound corresponds in each case to one row of table B.

Table 85: Compounds of the formula Ia, wherein Ar=Ar-85 as defined in table A, and Het for a compound corresponds in each case to one row of table B.

Table 86: Compounds of the formula Ia, wherein Ar=Ar-86 as defined in table A, and Het for a compound corresponds in each case to one row of table B.

Table 87: Compounds of the formula Ia, wherein Ar=Ar-87 as defined in table A, and Het for a compound corresponds in each case to one row of table B.

Table 88: Compounds of the formula Ia, wherein Ar=Ar-88 as defined in table A, and Het for a compound corresponds in each case to one row of table B.

Table 89: Compounds of the formula Ia, wherein Ar=Ar-89 as defined in table A, and Het for a compound corresponds in each case to one row of table B.

Table 90: Compounds of the formula Ia, wherein Ar=Ar-90 as defined in table A, and Het for a compound corresponds in each case to one row of table B.

Table 91: Compounds of the formula Ia, wherein Ar=Ar-91 as defined in table A, and Het for a compound corresponds in each case to one row of table B.

Table 92: Compounds of the formula Ia, wherein Ar=Ar-92 as defined in table A, and Het for a compound corresponds in each case to one row of table B.
Table 93: Compounds of the formula Ia, wherein Ar=Ar-93 as defined in table A, and Het for a compound corresponds in each case to one row of table B.
Table 94: Compounds of the formula Ia, wherein Ar=Ar-94 as defined in table A, and Het for a compound corresponds in each case to one row of table B.
Table 95: Compounds of the formula Ia, wherein Ar=Ar-95 as defined in table A, and Het for a compound corresponds in each case to one row of table B.
Table 96: Compounds of the formula Ia, wherein Ar=Ar-96 as defined in table A, and Het for a compound corresponds in each case to one row of table B.
Table 97: Compounds of the formula Ia, wherein Ar=Ar-97 as defined in table A, and Het for a compound corresponds in each case to one row of table B.
Table 98: Compounds of the formula Ia, wherein Ar=Ar-98 as defined in table A, and Het for a compound corresponds in each case to one row of table B.
Table 99: Compounds of the formula Ia, wherein Ar=Ar-99 as defined in table A, and Het for a compound corresponds in each case to one row of table B.
Table 100: Compounds of the formula Ia, wherein Ar=Ar-100 as defined in table A, and Het for a compound corresponds in each case to one row of table B.
Table 101: Compounds of the formula Ia, wherein Ar=Ar-101 as defined in table A, and Het for a compound corresponds in each case to one row of table B.
Table 102: Compounds of the formula Ia, wherein Ar=Ar-102 as defined in table A, and Het for a compound corresponds in each case to one row of table B.
Table 103: Compounds of the formula Ia, wherein Ar=Ar-103 as defined in table A, and Het for a compound corresponds in each case to one row of table B.
Table 104: Compounds of the formula Ia, wherein Ar=Ar-104 as defined in table A, and Het for a compound corresponds in each case to one row of table B.
Table 105: Compounds of the formula Ia, wherein Ar=Ar-105 as defined in table A, and Het for a compound corresponds in each case to one row of table B.
Table 106: Compounds of the formula Ia, wherein Ar=Ar-106 as defined in table A, and Het for a compound corresponds in each case to one row of table B.
Table 107: Compounds of the formula Ia, wherein Ar=Ar-107 as defined in table A, and Het for a compound corresponds in each case to one row of table B.
Table 108: Compounds of the formula Ia, wherein Ar=Ar-108 as defined in table A, and Het for a compound corresponds in each case to one row of table B.
Table 109: Compounds of the formula Ia, wherein Ar=Ar-109 as defined in table A, and Het for a compound corresponds in each case to one row of table B.
Table 110: Compounds of the formula Ia, wherein Ar=Ar-110 as defined in table A, and Het for a compound corresponds in each case to one row of table B.
Table 111: Compounds of the formula Ia, wherein Ar=Ar-111 as defined in table A, and Het for a compound corresponds in each case to one row of table B.
Table 112: Compounds of the formula Ia, wherein Ar=Ar-112 as defined in table A, and Het for a compound corresponds in each case to one row of table B.
Table 113: Compounds of the formula Ia, wherein Ar=Ar-113 as defined in table A, and Het for a compound corresponds in each case to one row of table B.
Table 114: Compounds of the formula Ia, wherein Ar=Ar-114 as defined in table A, and Het for a compound corresponds in each case to one row of table B.
Table 115: Compounds of the formula Ia, wherein Ar=Ar-115 as defined in table A, and Het for a compound corresponds in each case to one row of table B.
Table 116: Compounds of the formula Ia, wherein Ar=Ar-116 as defined in table A, and Het for a compound corresponds in each case to one row of table B.
Table 117: Compounds of the formula Ia, wherein Ar=Ar-117 as defined in table A, and Het for a compound corresponds in each case to one row of table B.
Table 118: Compounds of the formula Ia, wherein Ar=Ar-118 as defined in table A, and Het for a compound corresponds in each case to one row of table B.
Table 119: Compounds of the formula Ia, wherein Ar=Ar-119 as defined in table A, and Het for a compound corresponds in each case to one row of table B.
Table 120: Compounds of the formula Ia, wherein Ar=Ar-120 as defined in table A, and Het for a compound corresponds in each case to one row of table B.
Table 121: Compounds of the formula Ia, wherein Ar=Ar-121 as defined in table A, and Het for a compound corresponds in each case to one row of table B.
Table 122: Compounds of the formula Ia, wherein Ar=Ar-122 as defined in table A, and Het for a compound corresponds in each case to one row of table B.
Table 123: Compounds of the formula Ia, wherein Ar=Ar-123 as defined in table A, and Het for a compound corresponds in each case to one row of table B.
Table 124: Compounds of the formula Ia, wherein Ar=Ar-124 as defined in table A, and Het for a compound corresponds in each case to one row of table B.
Table 125: Compounds of the formula Ia, wherein Ar=Ar-125 as defined in table A, and Het for a compound corresponds in each case to one row of table B.
Table 126: Compounds of the formula Ia, wherein Ar=Ar-126 as defined in table A, and Het for a compound corresponds in each case to one row of table B.
Table 127: Compounds of the formula Ia, wherein Ar=Ar-127 as defined in table A, and Het for a compound corresponds in each case to one row of table B.
Table 128: Compounds of the formula Ia, wherein Ar=Ar-128 as defined in table A, and Het for a compound corresponds in each case to one row of table B.
Table 129: Compounds of the formula Ia, wherein Ar=Ar-129 as defined in table A, and Het for a compound corresponds in each case to one row of table B.
Table 130: Compounds of the formula Ia, wherein Ar=Ar-130 as defined in table A, and Het for a compound corresponds in each case to one row of table B.
Table 131: Compounds of the formula Ia, wherein Ar=Ar-131 as defined in table A, and Het for a compound corresponds in each case to one row of table B.
Table 132: Compounds of the formula Ia, wherein Ar=Ar-132 as defined in table A, and Het for a compound corresponds in each case to one row of table B.
Table 133: Compounds of the formula Ia, wherein Ar=Ar-133 as defined in table A, and Het for a compound corresponds in each case to one row of table B.
Table 134: Compounds of the formula Ia, wherein Ar=Ar-134 as defined in table A, and Het for a compound corresponds in each case to one row of table B.
Table 135: Compounds of the formula Ia, wherein Ar=Ar-135 as defined in table A, and Het for a compound corresponds in each case to one row of table B.

Table 136: Compounds of the formula Ia, wherein Ar=Ar-136 as defined in table A, and Het for a compound corresponds in each case to one row of table B.

Table 137: Compounds of the formula Ia, wherein Ar=Ar-137 as defined in table A, and Het for a compound corresponds in each case to one row of table B.

Table 138: Compounds of the formula Ia, wherein Ar=Ar-138 as defined in table A, and Het for a compound corresponds in each case to one row of table B.

Table 139: Compounds of the formula Ia, wherein Ar=Ar-139 as defined in table A, and Het for a compound corresponds in each case to one row of table B.

Table 140: Compounds of the formula Ia, wherein Ar=Ar-140 as defined in table A, and Het for a compound corresponds in each case to one row of table B.

Table 141: Compounds of the formula Ia, wherein Ar=Ar-141 as defined in table A, and Het for a compound corresponds in each case to one row of table B.

Table 142: Compounds of the formula Ia, wherein Ar=Ar-142 as defined in table A, and Het for a compound corresponds in each case to one row of table B.

Table 143: Compounds of the formula Ia, wherein Ar=Ar-143 as defined in table A, and Het for a compound corresponds in each case to one row of table B.

Table 144: Compounds of the formula Ia, wherein Ar=Ar-144 as defined in table A, and Het for a compound corresponds in each case to one row of table B.

Table 145: Compounds of the formula Ia, wherein Ar=Ar-145 as defined in table A, and Het for a compound corresponds in each case to one row of table B.

Table 146: Compounds of the formula Ia, wherein Ar=Ar-146 as defined in table A, and Het for a compound corresponds in each case to one row of table B.

Table 147: Compounds of the formula Ia, wherein Ar=Ar-147 as defined in table A, and Het for a compound corresponds in each case to one row of table B.

Table 148: Compounds of the formula Ia, wherein Ar=Ar-148 as defined in table A, and Het for a compound corresponds in each case to one row of table B.

Table 149: Compounds of the formula Ia, wherein Ar=Ar-149 as defined in table A, and Het for a compound corresponds in each case to one row of table B.

Table 150: Compounds of the formula Ia, wherein Ar=Ar-150 as defined in table A, and Het for a compound corresponds in each case to one row of table B.

Table 151: Compounds of the formula Ia, wherein Ar=Ar-151 as defined in table A, and Het for a compound corresponds in each case to one row of table B.

Table 152: Compounds of the formula Ia, wherein Ar=Ar-152 as defined in table A, and Het for a compound corresponds in each case to one row of table B.

Table 153: Compounds of the formula Ia, wherein Ar=Ar-153 as defined in table A, and Het for a compound corresponds in each case to one row of table B.

Table 154: Compounds of the formula Ia, wherein Ar=Ar-154 as defined in table A, and Het for a compound corresponds in each case to one row of table B.

Table 155: Compounds of the formula Ia, wherein Ar=Ar-155 as defined in table A, and Het for a compound corresponds in each case to one row of table B.

Table 156: Compounds of the formula Ia, wherein Ar=Ar-156 as defined in table A, and Het for a compound corresponds in each case to one row of table B.

Table 157: Compounds of the formula Ia, wherein Ar=Ar-157 as defined in table A, and Het for a compound corresponds in each case to one row of table B.

Table 158: Compounds of the formula Ia, wherein Ar=Ar-158 as defined in table A, and Het for a compound corresponds in each case to one row of table B.

Table 159: Compounds of the formula Ia, wherein Ar=Ar-159 as defined in table A, and Het for a compound corresponds in each case to one row of table B.

Table 160: Compounds of the formula Ia, wherein Ar=Ar-160 as defined in table A, and Het for a compound corresponds in each case to one row of table B.

Table 161: Compounds of the formula Ia, wherein Ar=Ar-161 as defined in table A, and Het for a compound corresponds in each case to one row of table B.

Table 162: Compounds of the formula Ia, wherein Ar=Ar-162 as defined in table A, and Het for a compound corresponds in each case to one row of table B.

Table 163: Compounds of the formula Ia, wherein Ar=Ar-163 as defined in table A, and Het for a compound corresponds in each case to one row of table B.

Table 164: Compounds of the formula Ia, wherein Ar=Ar-164 as defined in table A, and Het for a compound corresponds in each case to one row of table B.

Table 165: Compounds of the formula Ia, wherein Ar=Ar-165 as defined in table A, and Het for a compound corresponds in each case to one row of table B.

Table 166: Compounds of the formula Ia, wherein Ar=Ar-166 as defined in table A, and Het for a compound corresponds in each case to one row of table B.

Table 167: Compounds of the formula Ia, wherein Ar=Ar-167 as defined in table A, and Het for a compound corresponds in each case to one row of table B.

Table 168: Compounds of the formula Ia, wherein Ar=Ar-168 as defined in table A, and Het for a compound corresponds in each case to one row of table B.

Table 169: Compounds of the formula Ia, wherein Ar=Ar-169 as defined in table A, and Het for a compound corresponds in each case to one row of table B.

Table 170: Compounds of the formula Ia, wherein Ar=Ar-170 as defined in table A, and Het for a compound corresponds in each case to one row of table B.

Table 171: Compounds of the formula Ia, wherein Ar=Ar-171 as defined in table A, and Het for a compound corresponds in each case to one row of table B.

Table 172: Compounds of the formula Ia, wherein Ar=Ar-172 as defined in table A, and Het for a compound corresponds in each case to one row of table B.

Table 173: Compounds of the formula Ia, wherein Ar=Ar-173 as defined in table A, and Het for a compound corresponds in each case to one row of table B.

Table 174: Compounds of the formula Ia, wherein Ar=Ar-174 as defined in table A, and Het for a compound corresponds in each case to one row of table B.

Table 175: Compounds of the formula Ia, wherein Ar=Ar-175 as defined in table A, and Het for a compound corresponds in each case to one row of table B.

Table 176: Compounds of the formula Ia, wherein Ar=Ar-176 as defined in table A, and Het for a compound corresponds in each case to one row of table B.

Table 177: Compounds of the formula Ia, wherein Ar=Ar-177 as defined in table A, and Het for a compound corresponds in each case to one row of table B.

Table 178: Compounds of the formula Ia, wherein Ar=Ar-178 as defined in table A, and Het for a compound corresponds in each case to one row of table B.

Table 179: Compounds of the formula Ia, wherein Ar=Ar-179 as defined in table A, and Het for a compound corresponds in each case to one row of table B.

Table 180: Compounds of the formula Ia, wherein Ar=Ar-180 as defined in table A, and Het for a compound corresponds in each case to one row of table B.

Table 181: Compounds of the formula Ia, wherein Ar=Ar-181 as defined in table A, and Het for a compound corresponds in each case to one row of table B.

Table 182: Compounds of the formula Ia, wherein Ar=Ar-182 as defined in table A, and Het for a compound corresponds in each case to one row of table B.

Table 183: Compounds of the formula Ia, wherein Ar=Ar-183 as defined in table A, and Het for a compound corresponds in each case to one row of table B.

Table 184: Compounds of the formula Ia, wherein Ar=Ar-184 as defined in table A, and Het for a compound corresponds in each case to one row of table B.

Table 185: Compounds of the formula Ia, wherein Ar=Ar-185 as defined in table A, and Het for a compound corresponds in each case to one row of table B.

Table 186: Compounds of the formula Ia, wherein Ar=Ar-186 as defined in table A, and Het for a compound corresponds in each case to one row of table B.

Table 187: Compounds of the formula Ia, wherein Ar=Ar-187 as defined in table A, and Het for a compound corresponds in each case to one row of table B.

Table 188: Compounds of the formula Ia, wherein Ar=Ar-188 as defined in table A, and Het for a compound corresponds in each case to one row of table B.

Table 189: Compounds of the formula Ia, wherein Ar=Ar-189 as defined in table A, and Het for a compound corresponds in each case to one row of table B.

Table 190: Compounds of the formula Ia, wherein Ar=Ar-190 as defined in table A, and Het for a compound corresponds in each case to one row of table B.

Table 191: Compounds of the formula Ia, wherein Ar=Ar-191 as defined in table A, and Het for a compound corresponds in each case to one row of table B.

Table 192: Compounds of the formula Ia, wherein Ar=Ar-192 as defined in table A, and Het for a compound corresponds in each case to one row of table B.

Table 193: Compounds of the formula Ia, wherein Ar=Ar-193 as defined in table A, and Het for a compound corresponds in each case to one row of table B.

Table 194: Compounds of the formula Ia, wherein Ar=Ar-194 as defined in table A, and Het for a compound corresponds in each case to one row of table B.

Table 195: Compounds of the formula Ia, wherein Ar=Ar-195 as defined in table A, and Het for a compound corresponds in each case to one row of table B.

Table 196: Compounds of the formula Ia, wherein Ar=Ar-196 as defined in table A, and Het for a compound corresponds in each case to one row of table B.

Table 197: Compounds of the formula Ia, wherein Ar=Ar-197 as defined in table A, and Het for a compound corresponds in each case to one row of table B.

Table 198: Compounds of the formula Ia, wherein Ar=Ar-198 as defined in table A, and Het for a compound corresponds in each case to one row of table B.

Table 199: Compounds of the formula Ia, wherein Ar=Ar-199 as defined in table A, and Het for a compound corresponds in each case to one row of table B.

Table 200: Compounds of the formula Ia, wherein Ar=Ar-200 as defined in table A, and Het for a compound corresponds in each case to one row of table B.

Table 201: Compounds of the formula Ia, wherein Ar=Ar-201 as defined in table A, and Het for a compound corresponds in each case to one row of table B.

Table 202: Compounds of the formula Ia, wherein Ar=Ar-202 as defined in table A, and Het for a compound corresponds in each case to one row of table B.

Table 203: Compounds of the formula Ia, wherein Ar=Ar-203 as defined in table A, and Het for a compound corresponds in each case to one row of table B.

Table 204: Compounds of the formula Ia, wherein Ar=Ar-204 as defined in table A, and Het for a compound corresponds in each case to one row of table B.

Table 205: Compounds of the formula Ia, wherein Ar=Ar-205 as defined in table A, and Het for a compound corresponds in each case to one row of table B.

Examples of preferred compounds I are also the compounds of formula I, wherein $R^1$, $R^2$, $R^3$ are hydrogen, A is a radical $A^2$ with $R^{4a}$, $R^{4b}$, $R^{4c}$ and $R^{4d}$ being hydrogen, X is O and $R^6$ is hydrogen, and wherein Ar and Het are as defined in the tables 1 to 205.

Examples of preferred compounds I are also the compounds of formula I, wherein $R^1$, $R^2$, $R^3$ are hydrogen, A is a radical $A^2$ with $R^{4a}$, $R^{4b}$, $R^{4c}$ and $R^{4d}$ being hydrogen, X is NH and $R^6$ is hydrogen, and wherein Ar and Het are as defined in the tables 1 to 205.

Examples of preferred compounds I are also the compounds of formula I, wherein $R^1$, $R^2$, $R^3$ are hydrogen, A is a radical $A^2$ with $R^{4a}$, $R^{4b}$, $R^{4c}$ and $R^{4d}$ being hydrogen, X is $NCH_3$ and $R^6$ is hydrogen, and wherein Ar and Het are as defined in the tables 1 to 205.

Examples of preferred compounds I are also the compounds of formula I, wherein $R^1$, $R^2$, $R^3$ are hydrogen, A is a radical $A^2$ with $R^{4a}$, $R^{4b}$, $R^{4c}$ and $R^{4d}$ being hydrogen, X is $NC(O)CH_3$ and $R^6$ is hydrogen, and wherein Ar and Het are as defined in the tables 1 to 205.

Compounds of the general formula II and the salts thereof

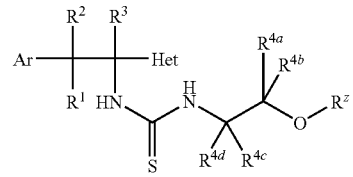

(II)

wherein Het, Ar, $R^1$, $R^2$, $R^3$, $R^{4a}$, $R^{4b}$, $R^{4c}$ and $R^{4d}$ are as defined above and wherein $R^z$ is hydrogen, or acetyl are new and thus form part of the invention.

As regards the pesticidal activity of the compounds of general formula II, preference is given to those compounds II wherein the variables Het, Ar, $R^1$, $R^2$, $R^3$, $R^{4a}$, $R^{4b}$, $R^{4c}$ and $R^{4d}$ have independently of each other or more preferably in combination the meanings mentioned above as being preferred.

Particular preference is also given to those compounds II, wherein $R^1$, $R^2$, $R^3$ are hydrogen;
$R^{4a}$, $R^{4b}$, $R^{4c}$, $R^{4d}$ are hydrogen; and
$R^z$ is hydrogen.

Particular preference is also given to those compounds II, wherein $R^1$, $R^2$, $R^3$ are hydrogen;
$R^{4a}$, $R^{4b}$, $R^{4c}$, $R^{4d}$ are hydrogen; and
$R^z$ is acetyl.

Examples of preferred compounds II, wherein $R^1$, $R^2$, $R^3$ are hydrogen, $R^{4a}$, $R^{4b}$, $R^{4c}$ and $R^{4d}$ are hydrogen, and $R^z$ is hydrogen are described in the following tables 206 to 410 (hereinafter also referred to as compounds IIa).

Table 206: Compounds of the formula IIa, wherein Ar=Ar-1 as defined in table A, and Het for a compound corresponds in each case to one row of table B.
Table 207: Compounds of the formula IIa, wherein Ar=Ar-2 as defined in table A, and Het for a compound corresponds in each case to one row of table B.
Table 208: Compounds of the formula IIa, wherein Ar=Ar-3 as defined in table A, and Het for a compound corresponds in each case to one row of table B.
Table 209: Compounds of the formula IIa, wherein Ar=Ar-4 as defined in table A, and Het for a compound corresponds in each case to one row of table B.
Table 210: Compounds of the formula IIa, wherein Ar=Ar-5 as defined in table A, and Het for a compound corresponds in each case to one row of table B.
Table 211: Compounds of the formula IIa, wherein Ar=Ar-6 as defined in table A, and Het for a compound corresponds in each case to one row of table B.
Table 212: Compounds of the formula IIa, wherein Ar=Ar-7 as defined in table A, and Het for a compound corresponds in each case to one row of table B.
Table 213: Compounds of the formula IIa, wherein Ar=Ar-8 as defined in table A, and Het for a compound corresponds in each case to one row of table B.
Table 214: Compounds of the formula IIa, wherein Ar=Ar-9 as defined in table A, and Het for a compound corresponds in each case to one row of table B.
Table 215: Compounds of the formula IIa, wherein Ar=Ar-10 as defined in table A, and Het for a compound corresponds in each case to one row of table B.
Table 216: Compounds of the formula IIa, wherein Ar=Ar-11 as defined in table A, and Het for a compound corresponds in each case to one row of table B.
Table 217: Compounds of the formula IIa, wherein Ar=Ar-12 as defined in table A, and Het for a compound corresponds in each case to one row of table B.
Table 218: Compounds of the formula IIa, wherein Ar=Ar-13 as defined in table A, and Het for a compound corresponds in each case to one row of table B.
Table 219: Compounds of the formula IIa, wherein Ar=Ar-14 as defined in table A, and Het for a compound corresponds in each case to one row of table B.
Table 220: Compounds of the formula IIa, wherein Ar=Ar-15 as defined in table A, and Het for a compound corresponds in each case to one row of table B.
Table 221: Compounds of the formula IIa, wherein Ar=Ar-16 as defined in table A, and Het for a compound corresponds in each case to one row of table B.
Table 222: Compounds of the formula IIa, wherein Ar=Ar-17 as defined in table A, and Het for a compound corresponds in each case to one row of table B.
Table 223: Compounds of the formula IIa, wherein Ar=Ar-18 as defined in table A, and Het for a compound corresponds in each case to one row of table B.
Table 224: Compounds of the formula IIa, wherein Ar=Ar-19 as defined in table A, and Het for a compound corresponds in each case to one row of table B.
Table 225: Compounds of the formula IIa, wherein Ar=Ar-20 as defined in table A, and Het for a compound corresponds in each case to one row of table B.
Table 226: Compounds of the formula IIa, wherein Ar=Ar-21 as defined in table A, and Het for a compound corresponds in each case to one row of table B.
Table 227: Compounds of the formula IIa, wherein Ar=Ar-22 as defined in table A, and Het for a compound corresponds in each case to one row of table B.
Table 228: Compounds of the formula IIa, wherein Ar=Ar-23 as defined in table A, and Het for a compound corresponds in each case to one row of table B.
Table 229: Compounds of the formula IIa, wherein Ar=Ar-24 as defined in table A, and Het for a compound corresponds in each case to one row of table B.
Table 230: Compounds of the formula IIa, wherein Ar=Ar-25 as defined in table A, and Het for a compound corresponds in each case to one row of table B.
Table 231: Compounds of the formula IIa, wherein Ar=Ar-26 as defined in table A, and Het for a compound corresponds in each case to one row of table B.
Table 232: Compounds of the formula IIa, wherein Ar=Ar-27 as defined in table A, and Het for a compound corresponds in each case to one row of table B.
Table 233: Compounds of the formula IIa, wherein Ar=Ar-28 as defined in table A, and Het for a compound corresponds in each case to one row of table B.
Table 234: Compounds of the formula IIa, wherein Ar=Ar-29 as defined in table A, and Het for a compound corresponds in each case to one row of table B.
Table 235: Compounds of the formula IIa, wherein Ar=Ar-30 as defined in table A, and Het for a compound corresponds in each case to one row of table B.
Table 236: Compounds of the formula IIa, wherein Ar=Ar-31 as defined in table A, and Het for a compound corresponds in each case to one row of table B.
Table 237: Compounds of the formula IIa, wherein Ar=Ar-32 as defined in table A, and Het for a compound corresponds in each case to one row of table B.
Table 238: Compounds of the formula IIa, wherein Ar=Ar-33 as defined in table A, and Het for a compound corresponds in each case to one row of table B.
Table 239: Compounds of the formula IIa, wherein Ar=Ar-34 as defined in table A, and Het for a compound corresponds in each case to one row of table B.
Table 240: Compounds of the formula IIa, wherein Ar=Ar-35 as defined in table A, and Het for a compound corresponds in each case to one row of table B.
Table 241: Compounds of the formula IIa, wherein Ar=Ar-36 as defined in table A, and Het for a compound corresponds in each case to one row of table B.
Table 242: Compounds of the formula IIa, wherein Ar=Ar-37 as defined in table A, and Het for a compound corresponds in each case to one row of table B.
Table 243: Compounds of the formula IIa, wherein Ar=Ar-38 as defined in table A, and Het for a compound corresponds in each case to one row of table B.
Table 244: Compounds of the formula IIa, wherein Ar=Ar-39 as defined in table A, and Het for a compound corresponds in each case to one row of table B.
Table 245: Compounds of the formula IIa, wherein Ar=Ar-40 as defined in table A, and Het for a compound corresponds in each case to one row of table B.
Table 246: Compounds of the formula IIa, wherein Ar=Ar-41 as defined in table A, and Het for a compound corresponds in each case to one row of table B.
Table 247: Compounds of the formula IIa, wherein Ar=Ar-42 as defined in table A, and Het for a compound corresponds in each case to one row of table B.
Table 248: Compounds of the formula IIa, wherein Ar=Ar-43 as defined in table A, and Het for a compound corresponds in each case to one row of table B.
Table 249: Compounds of the formula IIa, wherein Ar=Ar-44 as defined in table A, and Het for a compound corresponds in each case to one row of table B.

Table 250: Compounds of the formula IIa, wherein Ar=Ar-45 as defined in table A, and Het for a compound corresponds in each case to one row of table B.
Table 251: Compounds of the formula IIa, wherein Ar=Ar-46 as defined in table A, and Het for a compound corresponds in each case to one row of table B.
Table 252: Compounds of the formula IIa, wherein Ar=Ar-47 as defined in table A, and Het for a compound corresponds in each case to one row of table B.
Table 253: Compounds of the formula IIa, wherein Ar=Ar-48 as defined in table A, and Het for a compound corresponds in each case to one row of table B.
Table 254: Compounds of the formula IIa, wherein Ar=Ar-49 as defined in table A, and Het for a compound corresponds in each case to one row of table B.
Table 255: Compounds of the formula IIa, wherein Ar=Ar-50 as defined in table A, and Het for a compound corresponds in each case to one row of table B.
Table 256: Compounds of the formula IIa, wherein Ar=Ar-51 as defined in table A, and Het for a compound corresponds in each case to one row of table B.
Table 257: Compounds of the formula IIa, wherein Ar=Ar-52 as defined in table A, and Het for a compound corresponds in each case to one row of table B.
Table 258: Compounds of the formula IIa, wherein Ar=Ar-53 as defined in table A, and Het for a compound corresponds in each case to one row of table B.
Table 259: Compounds of the formula IIa, wherein Ar=Ar-54 as defined in table A, and Het for a compound corresponds in each case to one row of table B.
Table 260: Compounds of the formula IIa, wherein Ar=Ar-55 as defined in table A, and Het for a compound corresponds in each case to one row of table B.
Table 261: Compounds of the formula IIa, wherein Ar=Ar-56 as defined in table A, and Het for a compound corresponds in each case to one row of table B.
Table 262: Compounds of the formula IIa, wherein Ar=Ar-57 as defined in table A, and Het for a compound corresponds in each case to one row of table B.
Table 263: Compounds of the formula IIa, wherein Ar=Ar-58 as defined in table A, and Het for a compound corresponds in each case to one row of table B.
Table 264: Compounds of the formula IIa, wherein Ar=Ar-59 as defined in table A, and Het for a compound corresponds in each case to one row of table B.
Table 265: Compounds of the formula IIa, wherein Ar=Ar-60 as defined in table A, and Het for a compound corresponds in each case to one row of table B.
Table 266: Compounds of the formula IIa, wherein Ar=Ar-61 as defined in table A, and Het for a compound corresponds in each case to one row of table B.
Table 267: Compounds of the formula IIa, wherein Ar=Ar-62 as defined in table A, and Het for a compound corresponds in each case to one row of table B.
Table 268: Compounds of the formula IIa, wherein Ar=Ar-63 as defined in table A, and Het for a compound corresponds in each case to one row of table B.
Table 269: Compounds of the formula IIa, wherein Ar=Ar-64 as defined in table A, and Het for a compound corresponds in each case to one row of table B.
Table 270: Compounds of the formula IIa, wherein Ar=Ar-65 as defined in table A, and Het for a compound corresponds in each case to one row of table B.
Table 271: Compounds of the formula IIa, wherein Ar=Ar-66 as defined in table A, and Het for a compound corresponds in each case to one row of table B.
Table 272: Compounds of the formula IIa, wherein Ar=Ar-67 as defined in table A, and Het for a compound corresponds in each case to one row of table B.
Table 273: Compounds of the formula IIa, wherein Ar=Ar-68 as defined in table A, and Het for a compound corresponds in each case to one row of table B.
Table 274: Compounds of the formula IIa, wherein Ar=Ar-69 as defined in table A, and Het for a compound corresponds in each case to one row of table B.
Table 275: Compounds of the formula IIa, wherein Ar=Ar-70 as defined in table A, and Het for a compound corresponds in each case to one row of table B.
Table 276: Compounds of the formula IIa, wherein Ar=Ar-71 as defined in table A, and Het for a compound corresponds in each case to one row of table B.
Table 277: Compounds of the formula IIa, wherein Ar=Ar-72 as defined in table A, and Het for a compound corresponds in each case to one row of table B.
Table 278: Compounds of the formula IIa, wherein Ar=Ar-73 as defined in table A, and Het for a compound corresponds in each case to one row of table B.
Table 279: Compounds of the formula IIa, wherein Ar=Ar-74 as defined in table A, and Het for a compound corresponds in each case to one row of table B.
Table 280: Compounds of the formula IIa, wherein Ar=Ar-75 as defined in table A, and Het for a compound corresponds in each case to one row of table B.
Table 281: Compounds of the formula IIa, wherein Ar=Ar-76 as defined in table A, and Het for a compound corresponds in each case to one row of table B.
Table 282: Compounds of the formula IIa, wherein Ar=Ar-77 as defined in table A, and Het for a compound corresponds in each case to one row of table B.
Table 283: Compounds of the formula IIa, wherein Ar=Ar-78 as defined in table A, and Het for a compound corresponds in each case to one row of table B.
Table 284: Compounds of the formula IIa, wherein Ar=Ar-79 as defined in table A, and Het for a compound corresponds in each case to one row of table B.
Table 285: Compounds of the formula IIa, wherein Ar=Ar-80 as defined in table A, and Het for a compound corresponds in each case to one row of table B.
Table 286: Compounds of the formula IIa, wherein Ar=Ar-81 as defined in table A, and Het for a compound corresponds in each case to one row of table B.
Table 287: Compounds of the formula IIa, wherein Ar=Ar-82 as defined in table A, and Het for a compound corresponds in each case to one row of table B.
Table 288: Compounds of the formula IIa, wherein Ar=Ar-83 as defined in table A, and Het for a compound corresponds in each case to one row of table B.
Table 289: Compounds of the formula IIa, wherein Ar=Ar-84 as defined in table A, and Het for a compound corresponds in each case to one row of table B.
Table 290: Compounds of the formula IIa, wherein Ar=Ar-85 as defined in table A, and Het for a compound corresponds in each case to one row of table B.
Table 291: Compounds of the formula IIa, wherein Ar=Ar-86 as defined in table A, and Het for a compound corresponds in each case to one row of table B.
Table 292: Compounds of the formula IIa, wherein Ar=Ar-87 as defined in table A, and Het for a compound corresponds in each case to one row of table B.
Table 293: Compounds of the formula IIa, wherein Ar=Ar-88 as defined in table A, and Het for a compound corresponds in each case to one row of table B.

Table 294: Compounds of the formula IIa, wherein Ar=Ar-89 as defined in table A, and Het for a compound corresponds in each case to one row of table B.
Table 295: Compounds of the formula IIa, wherein Ar=Ar-90 as defined in table A, and Het for a compound corresponds in each case to one row of table B.
Table 296: Compounds of the formula IIa, wherein Ar=Ar-91 as defined in table A, and Het for a compound corresponds in each case to one row of table B.
Table 297: Compounds of the formula IIa, wherein Ar=Ar-92 as defined in table A, and Het for a compound corresponds in each case to one row of table B.
Table 298: Compounds of the formula IIa, wherein Ar=Ar-93 as defined in table A, and Het for a compound corresponds in each case to one row of table B.
Table 299: Compounds of the formula IIa, wherein Ar=Ar-94 as defined in table A, and Het for a compound corresponds in each case to one row of table B.
Table 300: Compounds of the formula IIa, wherein Ar=Ar-95 as defined in table A, and Het for a compound corresponds in each case to one row of table B.
Table 301: Compounds of the formula IIa, wherein Ar=Ar-96 as defined in table A, and Het for a compound corresponds in each case to one row of table B.
Table 302: Compounds of the formula IIa, wherein Ar=Ar-97 as defined in table A, and Het for a compound corresponds in each case to one row of table B.
Table 303: Compounds of the formula IIa, wherein Ar=Ar-98 as defined in table A, and Het for a compound corresponds in each case to one row of table B.
Table 304: Compounds of the formula IIa, wherein Ar=Ar-99 as defined in table A, and Het for a compound corresponds in each case to one row of table B.
Table 305: Compounds of the formula IIa, wherein Ar=Ar-100 as defined in table A, and Het for a compound corresponds in each case to one row of table B.
Table 306: Compounds of the formula IIa, wherein Ar=Ar-101 as defined in table A, and Het for a compound corresponds in each case to one row of table B.
Table 307: Compounds of the formula IIa, wherein Ar=Ar-102 as defined in table A, and Het for a compound corresponds in each case to one row of table B.
Table 308: Compounds of the formula IIa, wherein Ar=Ar-103 as defined in table A, and Het for a compound corresponds in each case to one row of table B.
Table 309: Compounds of the formula IIa, wherein Ar=Ar-104 as defined in table A, and Het for a compound corresponds in each case to one row of table B.
Table 310: Compounds of the formula IIa, wherein Ar=Ar-105 as defined in table A, and Het for a compound corresponds in each case to one row of table B.
Table 311: Compounds of the formula IIa, wherein Ar=Ar-106 as defined in table A, and Het for a compound corresponds in each case to one row of table B.
Table 312: Compounds of the formula IIa, wherein Ar=Ar-107 as defined in table A, and Het for a compound corresponds in each case to one row of table B.
Table 313: Compounds of the formula IIa, wherein Ar=Ar-108 as defined in table A, and Het for a compound corresponds in each case to one row of table B.
Table 314: Compounds of the formula IIa, wherein Ar=Ar-109 as defined in table A, and Het for a compound corresponds in each case to one row of table B.
Table 315: Compounds of the formula IIa, wherein Ar=Ar-110 as defined in table A, and Het for a compound corresponds in each case to one row of table B.
Table 316: Compounds of the formula IIa, wherein Ar=Ar-111 as defined in table A, and Het for a compound corresponds in each case to one row of table B.
Table 317: Compounds of the formula IIa, wherein Ar=Ar-112 as defined in table A, and Het for a compound corresponds in each case to one row of table B.
Table 318: Compounds of the formula IIa, wherein Ar=Ar-113 as defined in table A, and Het for a compound corresponds in each case to one row of table B.
Table 319: Compounds of the formula IIa, wherein Ar=Ar-114 as defined in table A, and Het for a compound corresponds in each case to one row of table B.
Table 320: Compounds of the formula IIa, wherein Ar=Ar-115 as defined in table A, and Het for a compound corresponds in each case to one row of table B.
Table 321: Compounds of the formula IIa, wherein Ar=Ar-116 as defined in table A, and Het for a compound corresponds in each case to one row of table B.
Table 322: Compounds of the formula IIa, wherein Ar=Ar-117 as defined in table A, and Het for a compound corresponds in each case to one row of table B.
Table 323: Compounds of the formula IIa, wherein Ar=Ar-118 as defined in table A, and Het for a compound corresponds in each case to one row of table B.
Table 324: Compounds of the formula IIa, wherein Ar=Ar-119 as defined in table A, and Het for a compound corresponds in each case to one row of table B.
Table 325: Compounds of the formula IIa, wherein Ar=Ar-120 as defined in table A, and Het for a compound corresponds in each case to one row of table B.
Table 326: Compounds of the formula IIa, wherein Ar=Ar-121 as defined in table A, and Het for a compound corresponds in each case to one row of table B.
Table 327: Compounds of the formula IIa, wherein Ar=Ar-122 as defined in table A, and Het for a compound corresponds in each case to one row of table B.
Table 328: Compounds of the formula IIa, wherein Ar=Ar-123 as defined in table A, and Het for a compound corresponds in each case to one row of table B.
Table 329: Compounds of the formula IIa, wherein Ar=Ar-124 as defined in table A, and Het for a compound corresponds in each case to one row of table B.
Table 330: Compounds of the formula IIa, wherein Ar=Ar-125 as defined in table A, and Het for a compound corresponds in each case to one row of table B.
Table 331: Compounds of the formula IIa, wherein Ar=Ar-126 as defined in table A, and Het for a compound corresponds in each case to one row of table B.
Table 332: Compounds of the formula IIa, wherein Ar=Ar-127 as defined in table A, and Het for a compound corresponds in each case to one row of table B.
Table 333: Compounds of the formula IIa, wherein Ar=Ar-128 as defined in table A, and Het for a compound corresponds in each case to one row of table B.
Table 334: Compounds of the formula IIa, wherein Ar=Ar-129 as defined in table A, and Het for a compound corresponds in each case to one row of table B.
Table 335: Compounds of the formula IIa, wherein Ar=Ar-130 as defined in table A, and Het for a compound corresponds in each case to one row of table B.
Table 336: Compounds of the formula IIa, wherein Ar=Ar-131 as defined in table A, and Het for a compound corresponds in each case to one row of table B.
Table 337: Compounds of the formula IIa, wherein Ar=Ar-132 as defined in table A, and Het for a compound corresponds in each case to one row of table B.

Table 338: Compounds of the formula IIa, wherein Ar=Ar-133 as defined in table A, and Het for a compound corresponds in each case to one row of table B.

Table 339: Compounds of the formula IIa, wherein Ar=Ar-134 as defined in table A, and Het for a compound corresponds in each case to one row of table B.

Table 340: Compounds of the formula IIa, wherein Ar=Ar-135 as defined in table A, and Het for a compound corresponds in each case to one row of table B.

Table 341: Compounds of the formula IIa, wherein Ar=Ar-136 as defined in table A, and Het for a compound corresponds in each case to one row of table B.

Table 342: Compounds of the formula IIa, wherein Ar=Ar-137 as defined in table A, and Het for a compound corresponds in each case to one row of table B.

Table 343: Compounds of the formula IIa, wherein Ar=Ar-138 as defined in table A, and Het for a compound corresponds in each case to one row of table B.

Table 344: Compounds of the formula IIa, wherein Ar=Ar-139 as defined in table A, and Het for a compound corresponds in each case to one row of table B.

Table 345: Compounds of the formula IIa, wherein Ar=Ar-140 as defined in table A, and Het for a compound corresponds in each case to one row of table B.

Table 346: Compounds of the formula IIa, wherein Ar=Ar-141 as defined in table A, and Het for a compound corresponds in each case to one row of table B.

Table 347: Compounds of the formula IIa, wherein Ar=Ar-142 as defined in table A, and Het for a compound corresponds in each case to one row of table B.

Table 348: Compounds of the formula IIa, wherein Ar=Ar-143 as defined in table A, and Het for a compound corresponds in each case to one row of table B.

Table 349: Compounds of the formula IIa, wherein Ar=Ar-144 as defined in table A, and Het for a compound corresponds in each case to one row of table B.

Table 350: Compounds of the formula IIa, wherein Ar=Ar-145 as defined in table A, and Het for a compound corresponds in each case to one row of table B.

Table 351: Compounds of the formula IIa, wherein Ar=Ar-146 as defined in table A, and Het for a compound corresponds in each case to one row of table B.

Table 352: Compounds of the formula IIa, wherein Ar=Ar-147 as defined in table A, and Het for a compound corresponds in each case to one row of table B.

Table 353: Compounds of the formula IIa, wherein Ar=Ar-148 as defined in table A, and Het for a compound corresponds in each case to one row of table B.

Table 354: Compounds of the formula IIa, wherein Ar=Ar-149 as defined in table A, and Het for a compound corresponds in each case to one row of table B.

Table 355: Compounds of the formula IIa, wherein Ar=Ar-150 as defined in table A, and Het for a compound corresponds in each case to one row of table B.

Table 356: Compounds of the formula IIa, wherein Ar=Ar-151 as defined in table A, and Het for a compound corresponds in each case to one row of table B.

Table 357: Compounds of the formula IIa, wherein Ar=Ar-152 as defined in table A, and Het for a compound corresponds in each case to one row of table B.

Table 358: Compounds of the formula IIa, wherein Ar=Ar-153 as defined in table A, and Het for a compound corresponds in each case to one row of table B.

Table 359: Compounds of the formula IIa, wherein Ar=Ar-154 as defined in table A, and Het for a compound corresponds in each case to one row of table B.

Table 360: Compounds of the formula IIa, wherein Ar=Ar-155 as defined in table A, and Het for a compound corresponds in each case to one row of table B.

Table 361: Compounds of the formula IIa, wherein Ar=Ar-156 as defined in table A, and Het for a compound corresponds in each case to one row of table B.

Table 362: Compounds of the formula IIa, wherein Ar=Ar-157 as defined in table A, and Het for a compound corresponds in each case to one row of table B.

Table 363: Compounds of the formula IIa, wherein Ar=Ar-158 as defined in table A, and Het for a compound corresponds in each case to one row of table B.

Table 364: Compounds of the formula IIa, wherein Ar=Ar-159 as defined in table A, and Het for a compound corresponds in each case to one row of table B.

Table 365: Compounds of the formula IIa, wherein Ar=Ar-160 as defined in table A, and Het for a compound corresponds in each case to one row of table B.

Table 366: Compounds of the formula IIa, wherein Ar=Ar-161 as defined in table A, and Het for a compound corresponds in each case to one row of table B.

Table 367: Compounds of the formula IIa, wherein Ar=Ar-162 as defined in table A, and Het for a compound corresponds in each case to one row of table B.

Table 368: Compounds of the formula IIa, wherein Ar=Ar-163 as defined in table A, and Het for a compound corresponds in each case to one row of table B.

Table 369: Compounds of the formula IIa, wherein Ar=Ar-164 as defined in table A, and Het for a compound corresponds in each case to one row of table B.

Table 370: Compounds of the formula IIa, wherein Ar=Ar-165 as defined in table A, and Het for a compound corresponds in each case to one row of table B.

Table 371: Compounds of the formula IIa, wherein Ar=Ar-166 as defined in table A, and Het for a compound corresponds in each case to one row of table B.

Table 372: Compounds of the formula IIa, wherein Ar=Ar-167 as defined in table A, and Het for a compound corresponds in each case to one row of table B.

Table 373: Compounds of the formula IIa, wherein Ar=Ar-168 as defined in table A, and Het for a compound corresponds in each case to one row of table B.

Table 374: Compounds of the formula IIa, wherein Ar=Ar-169 as defined in table A, and Het for a compound corresponds in each case to one row of table B.

Table 375: Compounds of the formula IIa, wherein Ar=Ar-170 as defined in table A, and Het for a compound corresponds in each case to one row of table B.

Table 376: Compounds of the formula IIa, wherein Ar=Ar-171 as defined in table A, and Het for a compound corresponds in each case to one row of table B.

Table 377: Compounds of the formula IIa, wherein Ar=Ar-172 as defined in table A, and Het for a compound corresponds in each case to one row of table B.

Table 378: Compounds of the formula IIa, wherein Ar=Ar-173 as defined in table A, and Het for a compound corresponds in each case to one row of table B.

Table 379: Compounds of the formula IIa, wherein Ar=Ar-174 as defined in table A, and Het for a compound corresponds in each case to one row of table B.

Table 380: Compounds of the formula IIa, wherein Ar=Ar-175 as defined in table A, and Het for a compound corresponds in each case to one row of table B.

Table 381: Compounds of the formula IIa, wherein Ar=Ar-176 as defined in table A, and Het for a compound corresponds in each case to one row of table B.

Table 382: Compounds of the formula IIa, wherein Ar=Ar-177 as defined in table A, and Het for a compound corresponds in each case to one row of table B.
Table 383: Compounds of the formula IIa, wherein Ar=Ar-178 as defined in table A, and Het for a compound corresponds in each case to one row of table B.
Table 384: Compounds of the formula IIa, wherein Ar=Ar-179 as defined in table A, and Het for a compound corresponds in each case to one row of table B.
Table 385: Compounds of the formula IIa, wherein Ar=Ar-180 as defined in table A, and Het for a compound corresponds in each case to one row of table B.
Table 386: Compounds of the formula IIa, wherein Ar=Ar-181 as defined in table A, and Het for a compound corresponds in each case to one row of table B.
Table 387: Compounds of the formula IIa, wherein Ar=Ar-182 as defined in table A, and Het for a compound corresponds in each case to one row of table B.
Table 388: Compounds of the formula IIa, wherein Ar=Ar-183 as defined in table A, and Het for a compound corresponds in each case to one row of table B.
Table 389: Compounds of the formula IIa, wherein Ar=Ar-184 as defined in table A, and Het for a compound corresponds in each case to one row of table B.
Table 390: Compounds of the formula IIa, wherein Ar=Ar-185 as defined in table A, and Het for a compound corresponds in each case to one row of table B.
Table 391: Compounds of the formula IIa, wherein Ar=Ar-186 as defined in table A, and Het for a compound corresponds in each case to one row of table B.
Table 392: Compounds of the formula IIa, wherein Ar=Ar-187 as defined in table A, and Het for a compound corresponds in each case to one row of table B.
Table 393: Compounds of the formula IIa, wherein Ar=Ar-188 as defined in table A, and Het for a compound corresponds in each case to one row of table B.
Table 394: Compounds of the formula IIa, wherein Ar=Ar-189 as defined in table A, and Het for a compound corresponds in each case to one row of table B.
Table 395: Compounds of the formula IIa, wherein Ar=Ar-190 as defined in table A, and Het for a compound corresponds in each case to one row of table B.
Table 396: Compounds of the formula IIa, wherein Ar=Ar-191 as defined in table A, and Het for a compound corresponds in each case to one row of table B.
Table 397: Compounds of the formula IIa, wherein Ar=Ar-192 as defined in table A, and Het for a compound corresponds in each case to one row of table B.
Table 398: Compounds of the formula IIa, wherein Ar=Ar-193 as defined in table A, and Het for a compound corresponds in each case to one row of table B.
Table 399: Compounds of the formula IIa, wherein Ar=Ar-194 as defined in table A, and Het for a compound corresponds in each case to one row of table B.
Table 400: Compounds of the formula IIa, wherein Ar=Ar-195 as defined in table A, and Het for a compound corresponds in each case to one row of table B.
Table 401: Compounds of the formula IIa, wherein Ar=Ar-196 as defined in table A, and Het for a compound corresponds in each case to one row of table B.
Table 402: Compounds of the formula IIa, wherein Ar=Ar-197 as defined in table A, and Het for a compound corresponds in each case to one row of table B.
Table 403: Compounds of the formula IIa, wherein Ar=Ar-198 as defined in table A, and Het for a compound corresponds in each case to one row of table B.
Table 404: Compounds of the formula IIa, wherein Ar=Ar-199 as defined in table A, and Het for a compound corresponds in each case to one row of table B.
Table 405: Compounds of the formula IIa, wherein Ar=Ar-200 as defined in table A, and Het for a compound corresponds in each case to one row of table B.
Table 406: Compounds of the formula IIa, wherein Ar=Ar-201 as defined in table A, and Het for a compound corresponds in each case to one row of table B.
Table 407: Compounds of the formula IIa, wherein Ar=Ar-202 as defined in table A, and Het for a compound corresponds in each case to one row of table B.
Table 408: Compounds of the formula IIa, wherein Ar=Ar-203 as defined in table A, and Het for a compound corresponds in each case to one row of table B.
Table 409: Compounds of the formula IIa, wherein Ar=Ar-204 as defined in table A, and Het for a compound corresponds in each case to one row of table B.
Table 410: Compounds of the formula IIa, wherein Ar=Ar-205 as defined in table A, and Het for a compound corresponds in each case to one row of table B.

Examples of preferred compounds II are also the compounds of formula II, wherein $R^1$, $R^2$, $R^3$ are hydrogen, $R^{4a}$, $R^{4b}$, $R^{4c}$ and $R^{4d}$ are hydrogen, and $R^z$ is acetyl, and wherein Ar and Het are as defined in the tables 206 to 410.

The compounds of formula I can be obtained as outlined in schemes 1 to 4.

The compounds of the formula I according to the invention wherein X is oxygen or sulfur can be e.g. prepared from the corresponding aminothiocarbonyl-ethane compounds II and aminocarbonyl-ethane compounds III, respectively, as shown in scheme 1:

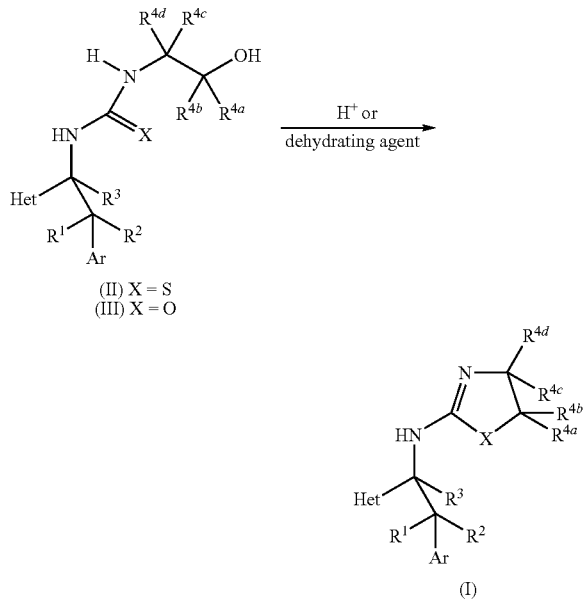

In scheme 1, $R^1$, $R^2$, $R^3$, $R^{4a}$, $R^{4b}$, $R^{4c}$, $R^{4d}$, Ar and Het are as defined above.

The aminothiocarbonylaminoethane compound II and the aminocarbonylaminoethane compound III, respectively, can be cyclized by conventional means thereby obtaining the azoline compound of the formula I. Cyclization of the compound II and III, respectively, can be achieved e.g. under acid catalysis or under dehydrating conditions e.g. by Mitsunobu's reaction (see Tetrahedron Letters 1999, 40, 3125-3128) or as described below (preparation examples).

Alternatively, the compounds of the formula I according to the invention wherein X is O or S can be prepared by the method shown in scheme 2.

Scheme 2:

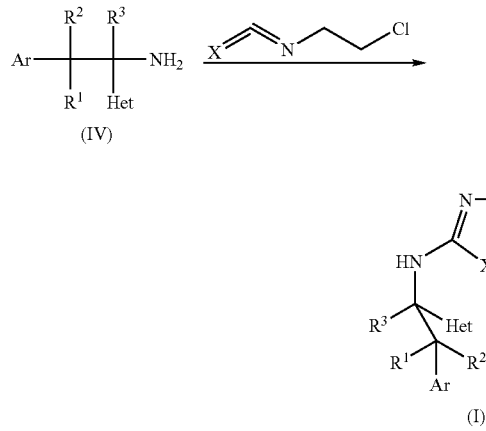

In scheme 2, $R^1$, $R^2$, $R^3$, $R^{4a}$, $R^{4b}$, $R^{4c}$, $R^{4d}$, Ar and Het are as defined above.

An amine IV or a salt thereof can be converted to an azoline I by reaction with 2-chloroethylisothiocyanate or 2-chloroethylisocyanate e.g. as described in Bioorg. Med. Chem. Lett. 1994, 4, 2317-22 and subsequent cyclization in the presence or absence of base. 1-Chloro-2-isothiocyanatoethane (CAS-reg.-no.: 6099-88-3) and 2-chloroethylisocyanate (CAS-reg.-no.: 1943-83-5) are commercially available.

Compounds of the formula I according to the invention wherein X is $NR^7$ may be prepared by the method shown in scheme 3.

Scheme 3:

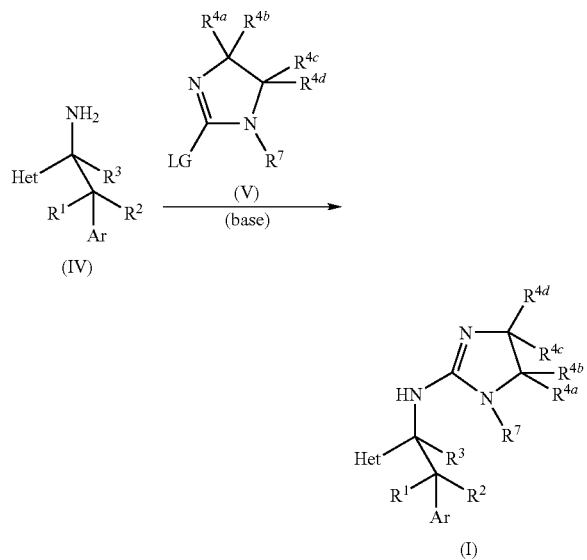

In scheme 3, $R^1$, $R^2$, $R^3$, $R^{4a}$, $R^{4b}$, $R^{4c}$, $R^{4d}$, $R^7$, Ar and Het are as defined above and LG is a leaving group.

Compounds of the formula I may be obtained by reacting an appropriate substituted amine IV or a salt thereof with a 2-substituted imidazoline V in an appropriate solvent. This reaction can be carried out, for example analogous to the methods described in U.S. Pat. No. 5,130,441 or EP 0389765.

Compounds of the formula I wherein $R^5$ and $R^6$, respectively, are not hydrogen, can be obtained as outlined in scheme 4.

Scheme 4:

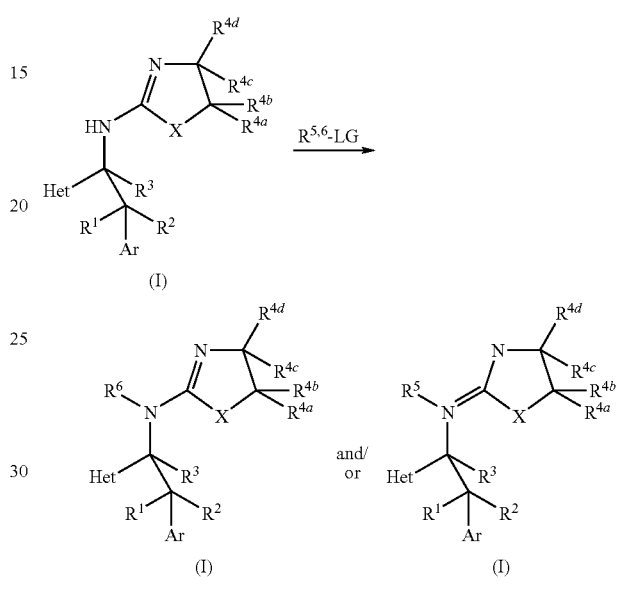

In scheme 4, $R^1$, $R^2$, $R^3$, $R^{4a}$, $R^{4b}$, $R^{4c}$, $R^{4d}$, X, Ar and Het are as defined above. A compound I wherein $R^5$ and $R^6$, respectively, are hydrogen is treated with a suitable electrophile. Suitable electrophiles are e.g. an alkylating or acylating agent $R^{5,6}$-LG (LG=leaving group) e.g. as described in WO 2005063724.

Amines IV are known in the art or can be prepared by methods familiar to an organic chemist, for instance by application of general methods for the synthesis of amines described in J. Org. Chem. 1983, 48, 289-294. or Tetrahedron 1999, 55, 8883-8904 and as demonstrated below in the preparation procedure. Suitable amine salts IV are e.g. the acid addition salts formed by treating an amine IV with an inorganic or organic acid. Anions of useful acids are e.g. sulfate, hydrogensulfate, phosphate, dihydrogenphosphate, hydrogenphosphate, nitrate, bicarbonate, carbonate, chloride, bromide, p-toluene sulfonate, and the anions of $C_1$-$C_4$-alkanoic acids such as acetate, propionate, and the like.

Compounds of the formula II and III, respectively, can be prepared as shown in schemes 5 and 6 below.

Scheme 5:

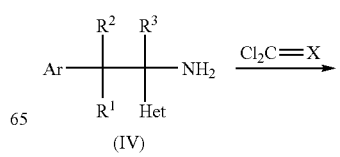

-continued

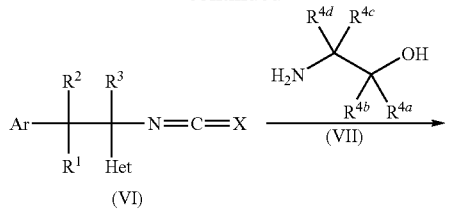 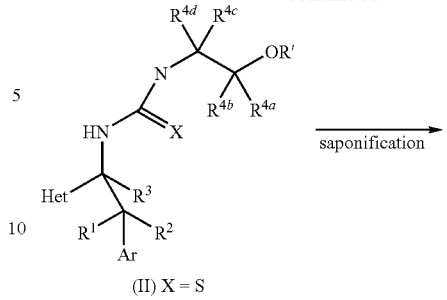

(II) X = S

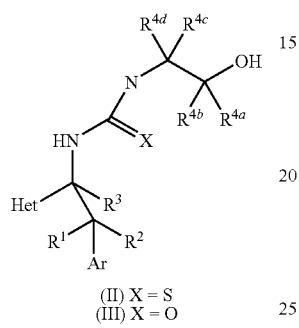

(II) X = S
(III) X = O

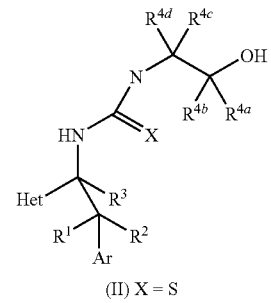

(II) X = S

In scheme 5, $R^1$, $R^2$, $R^3$, $R^{4a}$, $R^{4b}$, $R^{4c}$, $R^{4d}$, Ar and Het are as defined above.

An amine IV or a salt thereof is converted to the corresponding iso(thio)cyanate VI by conventional means, e.g. by reacting IV with (thio)phosgene, as described for example in the case of thiophosgene in Houben-Weyl, E4, "Methoden der Organischen Chemie", chapter IIc, pp. 837-842, Georg Thieme Verlag 1983. It may be advantageous to carry out the reaction in the presence of a base. The iso(thio)cyanate VI is then reacted with an aminoethanol VII to form an amino(thio)carbonylaminoethane compound. The reaction of the aminoethanol VII with iso(thio)cyanate V can be performed in accordance with standard methods of organic chemistry, see e.g. Biosci. Biotech. Biochem. 56 (7), 1062-65 (1992).

A further route to compounds II, wherein X is S is shown in scheme 6.

Scheme 6:

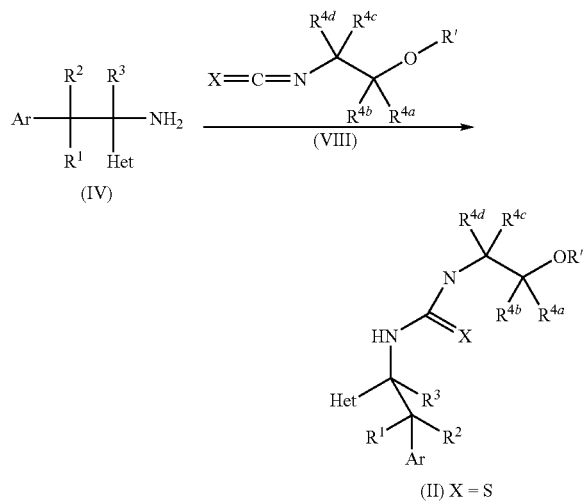

(II) X = S

In scheme 6, $R^1$, $R^2$, $R^3$, $R^{4a}$, $R^{4b}$, $R^{4c}$, $R^{4d}$, Ar and Het are as defined above and R' has the meanings given for $R^z$ or is e.g. benzoyl.

An amine IV or a salt thereof can be converted to the corresponding aminothiocarbonylaminoethane compound II, by reacting the amine IV with an isothiocyanates VIII and subsequent saponification as described in the preparation examples below. Isothiocyanates VII can be prepared according to the procedures described in Coll. Czech. Chem. Commun. 1986, 51, 112-117.

Compounds of the formulae I, II and III, respectively, wherein Het is a 5- or 6-membered nitrogen containing heteroaromatic ring may be converted to the corresponding N-oxides by treatment with a peracid under conditions known per se, for example by treating with hydrogen peroxide in an organic acid, such as formic acid, acetic acid, chloroacetic acid or trifluoroacetic acid (see, for example, J. Org. Chem. 55 (1990), 738-741 and Organic Synthesis, Collect. Vol. IV (1963), 655-656), or by reacting with an organic peracid, such as meta-perchlorobenzoic acid, in an inert solvent, for example a halogenated hydrocarbon, such as dichloromethane or dichloroethane (see, for example, Synthetic Commun. 22 (18) (1992), 2645; J. Med. Chem. (1998), 2146). Due to their excellent activity, the compounds of the general formulae I and II may be used for controlling animal pests, selected from harmful insects, acarids and nematodes.

Accordingly, the invention further provides agriculturally composition for combating such animal pests, which comprises such an amount of at least one compound of the general formulae I and II, respectively, or at least an agriculturally useful salt of I and II, respectively, and at least one inert liquid and/or solid agronomically acceptable carrier that it has a pesticidal action and, if desired, at least one surfactant.

Such a composition may contain a single active compound of the formulae I and II, respectively, or the enantiomers thereof or a mixture of several active compounds I and compounds II, respectively, according to the present invention. The composition according to the present invention may comprise an individual isomer or mixtures of isomers as well as individual tautomers or mixtures of tautomers.

The compounds of the formula I as well as the compounds of the formula II and the pesticidal compositions comprising them are effective agents for controlling animal pests, selected from insects, arachnids and nematodes. Animal pests controlled by the compounds of formula I include for example Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* Siphonatera, e.g. *Xenopsylla cheopsis, Ceratophyllus* spp The compositions and compounds of formula I as well as the compositions and compounds of formula II are useful for the control of nematodes, especially plant parasitic nematodes such as root knot nematodes, *Meloidogyne hapla, Meloidogyne incognita, Meloidogyne javanica*, and other *Meloidogyne* species;

cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formula I as well as the compounds of formula II are used for controlling insects or arachnids, in particular insects of the orders Lepidoptera, Coleoptera and Homoptera and arachnids of the order Acarina. The compounds of the formula I according to the present invention are particularly useful for controlling insects of the order Thysanoptera and Homoptera.

The compounds of formula I as well as the compounds of formula II or the pesticidal compositions comprising them may be used to protect growing plants and crops from attack or infestation by animal pests, especially insects, acaridae or arachnids by contacting the plant/crop with a pesticidally effective amount of compounds of formula I and formula II, respectively. The term "crop" refers both to growing and harvested crops.

The compounds of formula I as well as the compounds of formula II, can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gam ma-butyrolactone), pyrrolidones (N-methyl-pyrrolidones [NMP], N-octyl-pyrrolidone [NOP]), acetates (glycol diacetate), glycols, fatty acid dimethylamides, fatty acids and fatty acid esters. In principle, solvent mixtures may also be used.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compounds of formula I as well as the compounds of formula II can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% by weight.

The active compound(s) may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.
A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formula I as well as the compounds of formula II are also suitable for the treatment of seeds. Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Other preferred FS formulations of compounds of formula I for seed treatment comprise from 0.5 to 80 wt % of the active ingredient, from 0.05 to 5 wt % of a wetter, from 0.5 to 15 wt % of a dispersing agent, from 0.1 to 5 wt % of a thickener, from 5 to 20 wt % of an anti-freeze agent, from 0.1 to 2 wt % of an anti-foam agent, from 1 to 20 wt % of a pigment and/or a dye, from 0 to 15 wt % of a sticker/adhesion agent, from 0 to 75 wt % of a filler/vehicle, and from 0.01 to 1 wt % of a preservative.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I as well as the compounds of formula II are effective through both contact (via soil, glass, wall, bed net, carpet, plant parts or animal parts), and ingestion (bait, or plant part).

For use against ants, termites, wasps, flies, mosquitoes, crickets, or cockroaches, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as well as formulations of compounds of formula II as aerosols (e.g. in spray cans), oil sprays or pump sprays are highly suitable for the non-professional user for controlling pests such as flies, fleas, ticks, mosquitoes or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylfomamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I as well as the compounds of formula II and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I as well as compounds of formula II and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I as well as the compounds of formula II or the enantiomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasitically effective amount of compounds of formula I and formula II, a respectively, or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasitically effective amount of a compound of formula I and formula II, respectively, or the enantiomers or veterinarily acceptable salts thereof or a composition comprising it.

The invention also provides a process for the preparation of a composition for treating, controlling, preventing or protecting animals against infestation or infection by parasites which comprises a parasitically effective amount of a compound of formula I and formula II, respectively, or the enantiomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I as well as compounds of formula II are suitable for combating endo- and ectoparasites in and on animals.

Compounds of formula I as well as compounds of formula II or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I as well as compounds of formula II or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I as well as compounds of formula II or the enantiomers or veterinarily acceptable salts thereof and compositions comprising them are suitable for systemic and/or non-systemic control of ecto- and/or endoparasites. They are active against all or some stages of development.

The compounds of formula I as well as compounds of formula II are especially useful for combating ectoparasites.

The compounds of formula I as well as compounds of formula II are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, Actinedida (Prostigmata) und Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp.,

*Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I as well as compounds of formula II and compositions containing them are particularly useful for the control of pests from the orders Diptera, Siphonaptera and Ixodida.

Moreover, the use of the compounds of formula I as well as compounds of formula II and compositions containing them for combating mosquitoes is especially preferred.

The use of the compounds of formula I as well as compounds of formula II and compositions containing them for combating flies is a further preferred embodiment of the present invention.

Furthermore, the use of the compounds of formula I as well as compounds of formula II and compositions containing them for combating fleas is especially preferred.

The use of the compounds of formula I as well as the compounds of formula II and compositions containing them for combating ticks is a further preferred embodiment of the present invention.

The compounds of formula I as well as the compounds of formula II also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds as well as the formula II compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds as well as formula II compounds may be administered to animals parenterally, for example, by intraruminal, intramuscular, intravenous or subcutaneous injection. The formula I compounds as well as formula II compounds may be dispersed or dissolved in a physiologically acceptable carrier for subcutaneous injection. Alternatively, the formula I compounds as well as formula II compounds may be formulated into an implant for subcutaneous administration. In addition the formula I compound as well as formula II compounds may be transdermally administered to animals. For parenteral administration, the dosage form chosen should provide the animal with 0.01 mg/kg to 100 mg/kg of animal body weight per day of the formula I compound.

The formula I compounds as well as formula II compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds as well as formula II compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter,
fatty alcohols such as isotridecyl alcohol, 2-octyldodecanol, cetylstearyl alcohol, oleyl alcohol, and
fatty acids such as oleic acid and
mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether;
ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasitically effective amount" means the amount of active ingredient needed to achieve an observable effect on growth, including the effects of necrosis, death, retardation, prevention, and removal, destruction, or otherwise diminishing the occurrence and activity of the target organism. The parasitically effective amount can vary for the various compounds/compositions used in the invention. A parasitically effective amount of the compositions will also vary according to the prevailing conditions such as desired parasitical effect and duration, target species, mode of application, and the like.

The compositions which can be used in the invention can comprise generally from about 0.001 to 95% of the compound of formula I. The compositions which can be used in the invention can comprise generally from about 0.001 to 95% of the compound of formula II.

Generally it is favorable to apply the compounds of formula I as well as compounds of formula II in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I and formula II, respectively, against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I and the compound of formula II, respectively, are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I and formula II, respectively, in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I and formula II. A detailed list of plastics and elastomers as well as preparation procedures for the shaped articles is given e.g. in WO 03/086075.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds I and the compounds II, respectively, or the compositions comprising them in the use form as pesticides with other pesticides frequently results in a broader pesticidal spectrum of action.

The following list of pesticides together with which the compounds of formula I and the compounds of the formula II, respectively, can be used, is intended to illustrate the possible combinations, but not to impose any limitation:

Organo(thio)phosphates: acephate, azamethiphos, azinphos-ethyl, azinphos-methyl, cadusafos, chlorethoxyfos, chlorfenvinphos, chlormephos, chlorpyrifos, chlorpyrifosmethyl, chlorfenvinphos, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isoxathion, malathion, mecarbam, methamidophos, methidathion, methyl-parathion, mevinphos, monocrotophos, naled, omethoate, oxydemeton-methyl, paraoxon, parathion, parathion-methyl, phenthoate, phorate, phosalone, phosmet, phosphamidon, phorate, phoxim, pirimiphos, pirimiphos-methyl, profenofos, propetamphos, prothiofos, pyraclofos, pyridaphenthion, quinalphos, sulfotep, sulprophos, tebupirimfos, temephos, terbufos, tetrachlorvinphos, thiometon, triazophos, trichlorfon, vamidothion;

Carbamates: alanycarb, aldicarb, bendiocarb, benfuracarb, butocarboxim, butoxycarboxim, carbaryl, carbofuran, carbosulfan, ethiofoncarb, fenobucarb, fenoxycarb, formethanat, furathiocarb, isoprocarb, methiocarb, methomyl, metolcarb, oxamyl, pirimicarb, propoxur, thiodicarb, thiofanox, triazemate, trimethacarb, XMC, xylylcarb;

Pyrethroids: acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cyphenothrin, cypermethrin, alpha-cypermethrin, beta-cypermethrin, theta-cypermethrin, zeta-cypermethrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, prallethrin, profluthrin, pyrethrin I and II, resmethrin, RU 15525, silafluofen, tau-fluvalinate, tefluthrin, tetramethrin, tralomethrin, transfluthrin, dimefluthrin, ZXI 8901;

Growth regulators: a) chitin synthesis inhibitors: benzoylureas; bistrifluoron, chlorfluazuron, diflubenzuron, flucycloxuron, flufenoxuron, hexaflumuron, lufenuron, novaluron, noviflumuron, teflubenzuron, triflumuron; buprofezin, diofenolan, hexythiazox, etoxazole, clofentezine; b) ecdysone antagonists: chlormafenozide, halofenozide, methoxyfenozide, tebufenozide, azadirachtin; c) juvenoids: pyriproxyfen, hydroprene, kinoprene, methoprene, fenoxycarb; d) lipid biosynthesis inhibitors: spirodiclofen, spiromesifen, spirotetramat;

Nicotinic receptor agonists/antagonists compounds: acetamiprid, clothianidin, dinotefuran, imidacloprid, nitenpyram, thiacloprid, thiamethoxam, nicotine, bensultap, cartap hydrochloride, thiocyclam, thiosultap-sodium;

the thiazol compound of formula ($Γ^1$)

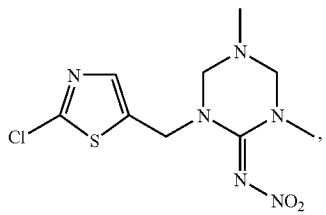

($Γ^1$)

GABA antagonist compounds: acetoprole, chlordane, endosulfan, ethiprole, gamma-HCH (lindane), fipronil, vaniliprole, pyrafluprole, pyriprole, vaniliprole, the phenylpyrazole compound of formula $Γ^2$

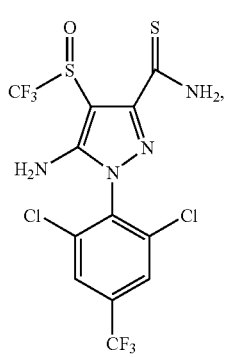

($Γ^2$)

Macrocyclic lactone insecticides: abamectin, emamectin, emamectin benzoate, milbemectin, lepimectin, spinosad.

METI I compounds: fenazaquin, fenpyroximate, flufenerim, pyridaben, pyrimidifen, rotenone, tebufenpyrad, tolfenpyrad;

METI II and III compounds: acequinocyl, fluacryprim, hydramethylnon;

Uncoupler compounds: chlorfenapyr, DNOC;

Oxidative phosphorylation inhibitor compounds: azocyclotin, cyhexatin, diafenthiuron, fenbutatin oxide, propargite, tetradifon;

Moulting disruptor compounds: cyromazine;

Mixed Function Oxidase inhibitor compounds: piperonyl butoxide;

Sodium channel blocker compounds: indoxacarb, metaflumizone,

Inorganic compounds: aluminium phosphide, borax, cryolite, cyanide, sulfuryl fluoride, phosphine;

Microbial disruptors of insect midgut membranes: *bacillus thuringiensis* subsp. *israelensis, bacillus sphaericus, bacillus thuringiensis* subsp. *aizawai, bacillus thuringiensis* subsp. *kurstaki, bacillus thuringiensis* subsp. *tenebrionis*;

Various: amitraz, benclothiaz, benzoximat, bifenazate, bromopropylate, cartap, chinomethionat, chloropicrin, flonicamid, methyl bromide, pyridalyl, pymetrozine, rynaxypursulfur, tartar emetic, thiocyclam, tribufosflubendiamide, cyenopyrafen, flupyrazofos, cyflumetofen, amidoflumet, NNI-0101, N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, anthranilamide compounds of formula $Γ^3$

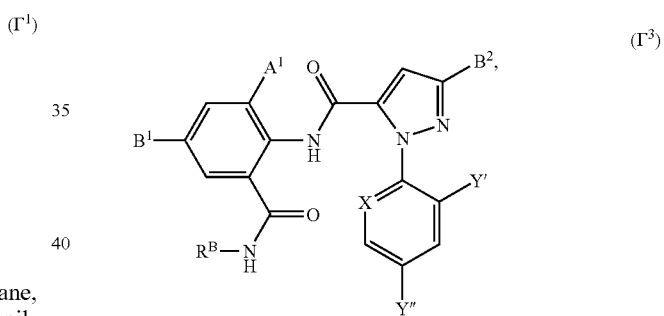

($Γ^3$)

wherein $A^1$ is $CH_3$, Cl, Br, I, X is C—H, C—Cl, C—F or N, Y' is F, Cl, or Br, Y" is F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$, and malononitrile compounds as described in JP 2002 284608, WO 02/89579, WO 02/90320, WO 02/90321, WO 04/06677, WO 04/20399, or JP 2004 99597.

The compounds of the formulae I or II of the present invention may also be combined with a fluorinated quinazolinone compound as:

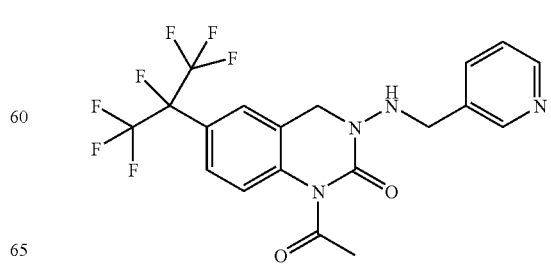

1-acetyl-3-[(pyridin-3-ylmethyl)-amino]-6-(1,2,2,2-tetrafluoro-1-trifluoromethyl-ethyl)-3,4-dihydro-1H-quinazolin-2-one.

The compounds of the formulae I or II of the present invention also be combined with a pyrimidinyl alkynylether compounds I'⁴ or thiadiazolyl alkynylether compounds I'⁵:

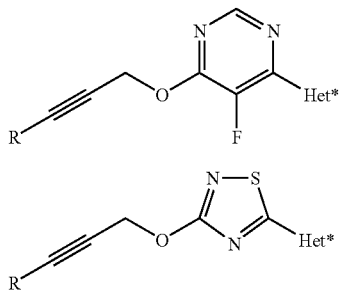

wherein R is methyl or ethyl and Het* is 3,3-dimethylpyrrolidin-1-yl, 3-methylpiperidin-1-yl, 3,5-dimethylpiperidin-1-yl, 4-methylpiperidin-1-yl, hexahydroazepin-1-yl, 2,6-dimethylhexahydroazepin-1-yl or 2,6-dimethylmorpholin-4-yl. These compounds are described e.g. in JP 2006131529.

The commercially available compounds of the group A may be found in The Pesticide Manual, 13th Edition, British Crop Protection Council (2003) among other publications. Thiamides of formula ε² and their preparation have been described in WO 98/28279. Lepimection is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180.

Anthranilamide compounds of formula ε³ and their preparation have been described in WO 01/70671; WO 02/48137; WO 03/24222, WO 03/15518, WO 04/67528; WO 04/33468; and WO 05/118552.

Fungicidal mixing partners are those selected from the group consisting of
  acylalanines such as benalaxyl, metalaxyl, ofurace, oxadixyl,
  amine derivatives such as aldimorph, dodine, dodemorph, fenpropimorph, fenpropidin, guazatine, iminoctadine, spiroxamin, tridemorph,
  anilinopyrimidines such as pyrimethanil, mepanipyrim or cyrodinyl,
  antibiotics such as cycloheximid, griseofulvin, kasugamycin, natamycin, polyoxin or streptomycin,
  azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol,
  dicarboximides such as iprodion, myclozolin, procymidon, vinclozolin,
  dithiocarbamates such as ferbam, nabam, maneb, mancozeb, metam, metiram, propineb, polycarbamate, thiram, ziram, zineb,
  heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine,
  copper fungicides such as Bordeaux mixture, copper acetate, copper oxychloride, basic copper sulfate,
  nitrophenyl derivatives such as binapacryl, dinocap, dinobuton, nitrophthalisopropyl,
  phenylpyrroles such as fenpiclonil or fludioxonil,
  sulfur,
  other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid,
  strobilurins such as azoxystrobin, dimoxystrobin, fluoxastrobin, kresoxim-methyl, metominostrobin, orysastrobin, picoxystrobin or trifloxystrobin,
  sulfenic acid derivatives such as captafol, captan, dichlofluanid, folpet, tolylfluanid,
  cinnamamides and analogs such as dimethomorph, flumetover or flumorph.

The animal pest, i.e. the insects, arachnids and nematodes, the plant, soil or water in which the plant is growing can be contacted with the present compound(s) I as well as compound(s) II or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and its compositions as well as compounds of formula II and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I as well as the compounds of formula II are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the invention can also be applied preventively to places at which occurrence of the pests is expected.

The compounds of formula I as well as compounds of formula II may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.001 weight % to 15 weight %, desirably from 0.001 weight % to 5 weight % of active compound.

For use in spray compositions, the content of active ingredient is from 0.001 to 80 weights %, preferably from 0.01 to 50 weight % and most preferably from 0.01 to 15 weight %.

For use in treating crop plants, the rate of application of the active ingredients of this invention may be in the range of 0.1 g to 4000 g per hectare, desirably from 25 g to 600 g per hectare, more desirably from 50 g to 500 g per hectare.

In the treatment of seed, the application rates of the mixture are generally from 0.1 g to 10 kg per 100 kg of seed, preferably from 1 g to 5 kg per 100 kg of seed, in particular from 1 g to 200 g per 100 kg of seed.

The present invention is now illustrated in further detail by the following examples.

SYNTHETIC EXAMPLES

I. Preparation of Starting Amines

Example 1

2-(3,5-Dimethyl-phenyl)-1-thien-2-yl-ethylamine

A solution of thiophene-2-carbaldehyde (2.24 g) in anhydrous toluene was cooled to 0° C. under nitrogen inert-gas atmosphere and a solution of lithium hexamethyldisilazane (LiHMDS, 22 ml, 1.1 equiv.) was added via cannula over a 30 min period. The reaction mixture was allowed to warm up to room temperature for 2 h. After cooling to 0° C. again a solution of 3,5-dimethylbenzylmagnesium chloride (50 ml, ca. 1.5 equiv.) in tetrahydrofuran (THF) was added within 10 min and the reaction mixture allowed to warm up to room temperature and stirring continued for 3 h. This solution was quenched with aqueous potassium carbonate solution (5%) and extracted with diethyl ether. The dried and concentrated ether extracts were purified by column chromatography to give the product (1.4 g) as a yellowish oil in 30% yield.

$^1$H-NMR (CDCl$_3$): δ=2.3 (s), 2.75 (dd), 3.15 (dd), 4.05 (mc), 6.8-7.2 ppm (m).

Example 2

2-(3,5-Dimethyl-phenyl)-1-furan-2-yl-ethylamine

Following the procedure as described in example 1, but using 1.92 g furan-2-carbaldehyde the title compound was obtained in 53% yield (2.3 g).

Example 3

2-(3,5-Dimethyl-phenyl)-1-(1-methyl-1H-pyrazol-4-yl)-ethylamine 3.1 R$_S$-2-Methyl-propane-2-sulfinic acid 1-methyl-3-trifluoromethyl-1H-pyrazol-4-yl-methyleneamide A solution of R$_S$-2-methyl-propane-2-sulfinic acid amide (1.5 g) and 1-methyl-3-trifluoro-methyl-1H-pyrazole-4-carbaldehyde (4.2 g) in 20 ml THF was treated with 34 g (10 equiv.) titanium tetraisopropoxide and stirred at room temperature overnight. The reaction mixture was poured into 400 ml of water and the precipitating titaniumoxides/-hydroxides removed by filtration through Celite. The filtrate was thoroughly washed with sodium bisulfite solution (ca. 20% in water) and the extract dried over magnesium sulphate. Evaporation of the solvents gave pure product (3.29 g) in 98% yield.

$^1$H-NMR (CDCl$_3$): δ=1.3 (s), 4.25 (s), 7.0 (s), 8.55 ppm (s).

3.2 R$_S$-2-Methyl-propane-2-sulfinic acid [2-(3,5-dimethyl-phenyl)-1-(1-methyl-1H-pyrazol-4-yl)-ethyl]-amide A solution of R$_S$-2-methyl-propane-2-sulfinic acid 1-methyl-1H-pyrazol-4-ylmethyleneamide (1.5 g) in 25 ml dichloromethylene was treated at −48° C. under nitrogen inert-gas atmosphere with a solution of 3,5-dimethylbenzylmagnesium chloride (15 ml in THF, ca. 0.8 molar). The solution was allowed to warm up to room temperature and stirred for 24 h. The reaction mixture was quenched with aqueous potassium carbonate solution (5%) and extracted with ethyl acetate. The dried and concentrated organic extracts were purified by column chromatography to give the product (2.05 g) as viscous oil in 88% yield as a mixture of two diasteroisomeres in a ca. 1:1 ratio 3.3 2-(3,5-Dimethyl-phenyl)-1-(1-methyl-1H-pyrazol-4-yl)-ethylamine A solution of R$_S$ 2-methyl-propane-2-sulfinic acid [2-(3,5-dimethyl-phenyl)-1-(1-methyl-1H-pyrazol-4-yl)-ethyl]-amide (2.0 g) in methanol (12 ml) was treated with a solution of hydrogenchloride in dioxane (12 ml, 4 N) at room temperature overnight. The reaction mixture was quenched with aqueous potassium carbonate solution and adjusted to pH 8-9, extracted and the organic phases dried over magnesium sulfate. After evaporation of the solvent a yellowish oil was obtained in 77% yield (1.05 g).

$^1$H-NMR (CDCl$_3$): δ=ca. 1.5 (br s), 2.3 (s), 2.7 (mc), 3.0 (mc), 3.85 (s), 4.2 (mc), 6.8 (s), 8.85 (s), 7.3 (s); 7.45 ppm (s).

Example 4

2-(3,5-Dimethyl-phenyl)-1-pyridin-3-yl-ethyl]-amine

4.1 R$_S$-2-methyl-propane-2-sulfinic Acid pyridin-3-ylmethyleneamide

Following the procedure as described in example 3.1, R$_S$-2-methyl-propane-2-sulfinic acid pyridin-3-ylmethyleneamide was prepared starting from pyridine-3-carbaldehyde and R$_S$-2-methyl-propane-2-sulfinic acid amide.

4.2 R$_S$-2-Methyl-propane-2-sulfinic Acid [2-(3,5-dimethyl-phenyl)-1-pyridin-3-yl-ethyl]-amide A solution of R$_S$-2-Methyl-propane-2-sulfinic acid pyridin-3-ylmethyleneamide (0.77 g) in 15 ml dichloroethane was treated at −48° C. under nitrogen inert-gas atmosphere with a solution of 3,5-dimethylbenzylmagnesium chloride (5 ml in THF, ca. 3.9 molar). The solution was allowed to warm up to room temperature and stirred for 24 h. The reaction mixture was quenched with aqueous potassium carbonate solution (5%) and extracted with diethyl ether. The dried and concentrated organic extracts were purified by column chromatography to give the product (90%) as a mixture of two separable diasteroisomeres in a ca. 1:3 ratio (less polar isomer: 170 mg, major isomer (more polar) 480 mg).

4.3 2-(3,5-Dimethyl-phenyl)-1-pyridin-3-yl-ethyl]-amine

Following the procedure as described in example 3.3, the title compound was obtained.

Amines IV not described above can be prepared in an analogous manner.

II. Preparation of 1-(aminothiocarbonylamino)-2-aryl-1-hetaryl-ethane Compounds of the Formula II

Example 5

Acetic Acid 2-{3-[2-(3,5-dimethyl-phenyl)-1-thien-2-yl-ethyl]-thioureido}-ethyl Ester A solution of 2-(3,5-dimethyl-phenyl)-1-thiophen-2-yl-ethylamine (1.4 g, from example 1) and acetic acid 2-isothiocyanato-ethyl ester (0.75 g, prepared according to Collect. Czech. Chem. Commun. 1986, 51, 112-117) in toluene (15 ml) was stirred at room temperature for 12 h, evaporated and the residue purified by column chromatography to yield the product (0.5 g) as a yellowish oil.

Example 6

1-[2-(3,5-Dimethyl-phenyl)-1-thien-2-yl-ethyl]-3-(2-hydroxy-ethyl)-thiourea

A solution of the above ethyl ester (0.43 g) was dissolved in tetrahydrofuran (20 ml) and cooled to 0° C. A solution of lithium hydroxide (55 mg) in water (20 ml) was added at room temperature and stirred overnight. Extraction with diethyl ether, washing with water and drying over magnesium sulfate gave the product after solvent-evaporation in 92% yield (0.35 g) as viscous oil.

Compounds of the formula II (wherein $R^1$, $R^2$, $R^3$, $R^{4a}$, $R^{4b}$, $R^{4c}$ and $R^{4d}$ are hydrogen) listed in table I below were prepared in an analogous manner.

TABLE I

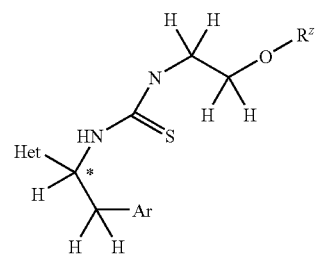

(II)

| Ex. no. | Ar | Het | R$^z$ | Physico-chemical data (m.p. [° C.]/$^1$H-NMR [ppm]) | stereogenic centre at * |
|---|---|---|---|---|---|
| 5 | 3,5-di-Me-Ph | 2-thienyl | Ac | CDCl$_3$: δ = 2.0 (s), 2.25 (s), 3.1 (mc), 3.7 (mc), 4.1 (mc), 5.45 (br s), 6.1 (s), 6.4 (s), 6.75-7.25 ppm (m) | racemate |
| 6 | 3,5-di-Me-Ph | 2-thienyl | H | CDCl$_3$: δ = 2.25 (s), 3.15 (mc), 3.45 (mc), 3.55 (mc), 5.7 (br s), 6.4 (br s), 6.7-7.2 ppm (m) | racemate |
| 7 | Ph | 2-thienyl | H | 115-118° C. | racemate |
| 8 | 3-Me-Ph | 2-thienyl | H | CDCl$_3$: δ = 2.30 (s), 2.5 (s), 3.1-3.25 (m), 3.45 (mc), 3.6 | racemate |

TABLE I-continued

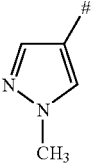

(II)

| Ex. no. | Ar | Het | R$^z$ | Physico-chemical data (m.p. [° C.]/$^1$H-NMR [ppm]) | stereo-genic centre at * |
|---|---|---|---|---|---|
| | | | | (mc), 5.7 (br s), 6.35 (s), 6.9-7.2 ppm (m) | |
| 9 | Ph | 3-methyl-2-thienyl | H | 156-159° C. | racemate |
| 10 | 3,5-di-Me-Ph | 2-furyl | Ac | 97-99° C. | racemate |
| 11 | 3,5-di-Me-Ph | 2-furyl | H | CDCl$_3$: δ = 2.2 (s), 3.1 (mc), 3.45 (mc), 3.6 (mc), 5.55 (br s), 6.1-7.35 ppm (m) | racemate |
| 12 | 3,5-di-Me-Ph | 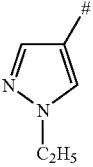 | Ac | CDCl$_3$: δ = 2.0 (s), 2.25 (s), 2.95 (mc), 3.1 (mc), 3.7 (mc), 3.8 (s), 4.1 (mc), 6.3 (s), 6.5 (d), 6.75 (s), 6.85 (s), 7.2 (s), 7.35 ppm (s) | 1:1 |
| 13 | 3,5-di-Me-Ph | 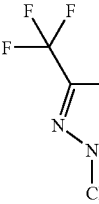 | Ac | CDCl$_3$: δ = 1.45 (t), 2.00 (s), 2.25 (s), 2.95 (mc), 3.1 (mc), 3.75 (mc), 4.0-4.2 (m), 6.15 (br s), 6.4 (d), 6.75 (s), 6.85 (s), 7.20 (s), 7.35 ppm (s) | 1:1 |
| 14 | 3,5-di-Me-Ph | 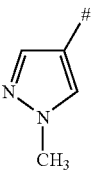 | Ac | CDCl$_3$: δ = 2.05 (s), 2.25 (s), 2.95 (mc), 3.2 (mc), 3.70 (mc), 4.15 (mc), 5.8 (br s), 6.35 (br s), 6.45 (s), 6.70 (s), 6.85 ppm (s) | 1:1 |
| 15 | 3,5-di-Me-Ph | 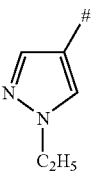 | H | d$_6$-DMSO: δ = 2.20 (s), 2.90 (mc), 3.10 (mc), 3.45 (mc), 3.75 (s), 4.8 (s), 5.55 (s), 6.75 (s), 6.85 (s), 7.25 (s), 7.35 (s), 7.5 (s), 7.7 ppm (d) | 1:1 |
| 16 | 3,5-di-Me-Ph | 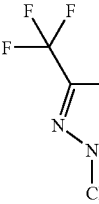 | H | d$_6$-DMSO: δ = 1.30 (t), 2.20 (s), 2.90 (mc), 3.10 (mc), 3.45 (mc), 4.05 (q), 4.75 (s), 5.5 (s), 6.75 (s), 6.8 (s), 7.3 (s), 7.35 (s), 7.55 (s), 7.77 ppm (d) | 1:1, |

TABLE I-continued

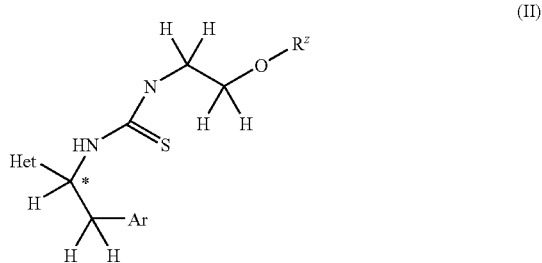
(II)

| Ex. no. | Ar | Het | R$^z$ | Physico-chemical data (m.p. [° C.]/$^1$H-NMR [ppm]) | stereogenic centre at * |
|---|---|---|---|---|---|
| 17 | 3,5-di-Me-Ph | ![structure with CF3, pyrazole, N-CH3] | H | d$_6$-DMSO: δ = 2.20 (s), 3.0 (mc), 3.10 (mc), 3.45 (mc), 3.79 (s), 4.80 (s), 5.70 (s), 6.70 (s), 6.80 (s), 6.85 (s), 7.50 (s), 8.00 ppm (d) | 1:1, |
| 18 | Ph | 2-pyridyl | H | 112-115° C. | racemate |
| 19 | Ph | 3-pyridyl | H | d$_6$-DMSO: δ = 3.0-3.2 (m), 3.3-3.5 (m), 4.8 (s), 5.65 (s), 7.1-7.7 (m), 8.1 (d), 8.4 (mc) | racemate |
| 20 | 3,5-di-Me-Ph | 3-pyridyl | Ac | CDCl$_3$: δ = 1.90 (s), 2.25 (s), 3.05 (mc), 3.7 (mc), 4.1 (mc), 5.35 (s), 6.45 (s), 6.65 (s), 6.85 (s), 7.1 (d), 8.5 ppm (mc) | racemate |
| 21 | 3,5-di-Me-Ph | 3-pyridyl | H | CDCl$_3$: δ = 2.25 (s), 2.9 (mc), 3.4 (mc), 3.65 (mc), 5.55 (s), 6.65 (s), 6.8 (s), 7.0 (s), 7.15 (s), 7.5 (mc), 8.35 ppm (mc). | racemate | ex. = example
Me = methyl
Ph = phenyl
Ac = acetyl
DMSO = dimethyl sulfoxide
# = position of attachment in formula II
m.p. = melting point III. Preparation of 1-(azolin-2-yl)-amino-2-aryl-1-hetaryl-ethane Compounds of the Formula I Example 22

(4,5-Dihydro-thiazol-2-yl)-[2-(3,5-dimethyl-phenyl)-1-thien-2-yl-ethyl]-amine

To a solution of 1-[2-(3,5-dimethyl-phenyl)-1-thiophen-2-yl-ethyl]-3-(2-hydroxy-ethyl)-thiourea (0.30 g) from example 6 and diisopropyethylamine (0.16 g) in propionitrile (10 ml) was added cyanomethyl-trimethyl-phosphonium iodide (0.27 g, prepared according to Tetrahedron 2001, 57, 5451-54). The reaction mixture was heated up to 90° C. for 72 h. Extraction with ethyl acetate, washing with potassium carbonate solution and water followed by drying and evaporation of the solvent yielded 0.27 mg (95%) of the title compound as brownish oil.

$^1$H-NMR (CDCl$_3$): δ=2.25 (s), 3.1 (mc), 3.25 (mc), 3.85 (mc), 5.2 (mc), 6.65-7.15 ppm (m).

Example 23

(4,5-Dihydro-thiazol-2-yl)-[2-(3,5-dimethyl-phenyl)-1-furan-2-yl-ethyl]-amine

Following the procedure as described in example a solution of 1-[2-(3,5-dimethylphenyl)-1-furan-2-yl-ethyl]-3-(2-hydroxy-ethyl)-thiourea (0.46 g) and diisopropyethylamine (0.26 g) in propionitrile (20 ml) was treated with cyanomethyl trimethylphosphonium iodide (0.44 g) and heated for 16 h at a temperature of 90° C. Work-up yielded the title compound (0.30 g, 69%) as an amorphous solid.

Compounds of the formula I wherein R$^1$, R$^2$, R$^3$, R$^{4a}$, R$^{4b}$, R$^{4c}$, R$^{4d}$ and R$^6$ are hydrogen and X is S, of table II below were prepared in an analogous manner.

TABLE II (I)

Structure: Het-CH(H)(*)-NH-(4,5-dihydrothiazol-2-yl), with CH(*) bonded to CH2-Ar

| Ex. no. | Ar | Het | Physico-chemical data (m.p. [° C.]; $^1$H-NMR [ppm]) | Remark for stereogenic centre at * |
|---|---|---|---|---|
| 22 | 3,5-di-Me-Ph | 2-thienyl | CDCl$_3$: δ = 2.25 (s), 3.1 (mc), 3.25 (mc), 3.85 (mc), 5.2 (mc), 6.65-7.15 ppm (m) | racemate |
| 23 | 3,5-di-Me-Ph | 2-furyl | CDCl$_3$: δ = 2.2 (s), 3.1 (mc), 3.3 (mc), 3.95 (mc), ca. 4.4 (br s), 5.1 (mc), 6.05 (s), 6.25 (s), 6.6 (s), 6.8 (s), 7.4 ppm (s). | racemate |
| 24 | Ph | 2-pyridyl | CDCl$_3$: δ = 3.1-3.5 (m), 3.95 (mc), 5.15 (mc), 6.85-7.5 (m), 8.5 ppm (s) | racemate |
| 25 | Ph | 3-pyridyl | CDCl$_3$: δ = 3.0-3.3 (m), 3.8 (mc), 4.9 (mc), 6.95-7.5 (m), 8.45 ppm (s) | racemate |
| 26 | Ph | 4-pyridyl | 110-116° C. | racemate |
| 27 | 3,5-di-Me-Ph | 3-pyridyl | d$_6$-DMSO: δ = 2.2 (s), 2.75-3.00 (m), 3.15 (mc), 3.70 (mc), 4.9 (br s), 6.7 (s), 7.3 (s), 7.4 (mc), 8.35-8.5 ppm (m) | racemate |
| 28 | 3,5-di-Me-Ph | 1-methyl-pyrazol-4-yl (# = attachment) | CDCl$_3$: δ = 2.2 (s), 2.8 (mc), 3.0 (mc), 3.7-3.8 (m), 4.85 (mc), 6.7-6.8 (m), 7.0 (s), 7.25 (s), 7.4 ppm (s) | 1:1 |
| 29 | 3,5-di-Me-Ph | 1-ethyl-pyrazol-4-yl (# = attachment) | d$_6$-DMSO: δ = 1.3 (t), 2.2 (s), 2.85 (dd), 2.95 (dd), 3.15 (t), 3.8 (mc), 4.0 (mc), 4.85 (mc), 6.75 (s), 7.0 (s), 7.3 (s), 7.5 ppm (s) | ca. 1:1 |
| 30 | 3,5-di-Me-Ph | 1-methyl-3-trifluoromethyl-pyrazol-4-yl (# = attachment) | 173-177° C. | ca. 1:1 |
| 31 | 3-Cl-Ph | 3-pyridyl | 149-154° C. | racemate |
| 32 | 3,5-di-Me-Ph | 5-methyl-2-thienyl | d$_6$-DMSO: δ = 2.2 (s), 2.35 (s), 2.95 (mc), 3.15 (mc), 3.7 (mc), 5.05 (br s), 6.55 (d), 6.65 (d), 6.75-6.85 (m), 7.25 ppm (br s) | ca. 1:1 |
| 33 | 3,5-di-Me-Ph | 3-methyl-2-thienyl | d$_6$-DMSO: δ = 1.95 (s), 2.3 (s), 2.8 (mc), 3.0 (mc), 3.15 (t), 3.7 (mc), 5.1 (br s), 6.65-6.8 (m), 7.2 (d), 7.3 (d), 7.3 ppm (br s) | ca. 1:3 |
| 34 | 3,5-di-Me-Ph | 5-chloro-2-thienyl | d$_6$-DMSO: δ = 2.2 (s), 2.95 (mc), 3.2 (mc), 3.7 (mc), 5.05 (br s), 6.7-6.9 (m), 7.4 ppm (br s) | ca. 1:2 |

TABLE II-continued

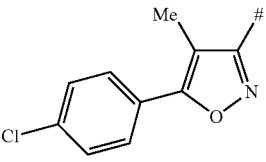

(I)

| Ex. no. | Ar | Het | Physico-chemical data (m.p. [° C.]; ¹H-NMR [ppm]) | Remark for stereogenic centre at * |
|---|---|---|---|---|
| 35 | 3,5-di-Me-Ph | 4-cyano-2-thienyl | 150.00-153.00° C. | ca. 1:1.5 |
| 36 | 3,5-di-Me-Ph | 4-bromo-2-thienyl | $d_6$-DMSO: δ = 2.2 (s), 2.95 (mc), 3.2 (mc), 3.7 (mc), 5.1 (br s), 6.8-6.9 (m), 7.3-7.5 ppm (m) | ca. 1:2 |
| 37 | 3,5-di-Me-Ph | 3-fluoro-4-pyridyl | $d_6$-DMSO: δ = 2.2 (s), 2.75-2.95 (m), 3.2 (mc), 3.65 (mc), 5.15 (br s), 6.6-6.7 (m), 7.4-7.6 ppm (m), 8.4 (mc) | ca. 1:3 |
| 38 | 3,5-di-Me-Ph | 3-chloro-4-pyridyl | $d_6$-DMSO: δ = 2.2 (s), 2.65-2.85 (m), 3.1 (mc), 3.6 (mc), 5.2 (br s), 6.8-6.9 (m), 7.4-7.6 (m), 8.5 ppm (mc) | ca. 1:3 |
| 39 | 3,5-di-Me-Ph | 5-bromo-2-thienyl | $d_6$-DMSO: δ = 2.2 (s), 2.95 (mc), 3.2 (mc), 3.7 (mc), 5.05 (br s), 6.7-7.05 (m), 7.3 ppm (br s) | ca. 1:1.5 |
| 40 | 3,5-di-Me-Ph | 6-trifluoro-methyl-3-pyridyl | $d_6$-DMSO: δ = 2.2 (s), 2.8-3.2 (m), 3.65 (mc), 5.0 (br s), 6.8 (mc), 7.8-8.0 (m), 8.6 (s) | ca. 1:2 |
| 41 | 3,5-di-Me-Ph | 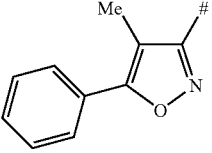 | $d_6$-DMSO: δ = 2.1 (s), 2.2 (s), 3.05 (mc), 3.2 (mc), 3.7 (mc), 5.1 (br s), 6.75-6.9 (m), 7.4 (br s), 7.6 (d), 7.7 ppm(d) | >1:10 |
| 42 | 3,5-di-Me-Ph | (Me, phenyl isoxazole) # | $d_6$-DMSO: δ = 2.1 (s), 2.2 (s), 3.05 (mc), 3.2 (mc), 3.75 (mc), 5.1 (br s), 6.8 (s), 6.85 (s), 7.4-7.7 ppm (m) | ca. 1:2 |
| 43 | 3,5-di-Me-Ph | 5-chloro-2-furyl | $d_6$-DMSO: δ = 2.2 (s), 2.95 (mc), 3.2 (mc), 3.75 (mc), 4.9 (br s), 6.2 (d), 6.3 (d), 6.8 (mc), 7.3 ppm (br s) | ca. 1:2 |
| 44 | 3,5-di-Me-Ph | 6-methoxy-3-pyridyl | $CDCl_3$: δ = 2.2 (s), 3.0 (mc), 3.3 (mc), 3.8-3.95 (m), 4.85 (mc), 6.6-6.85 (m), 7.4 (mc), 8.0 ppm (s) | ca. 1:2 |
| 45 | 3,5-di-Me-Ph | 6-methyl-2-pyridyl | $CDCl_3$: δ = 2.15(s), 2.2 (s), 2.95-3.3 (m), 4.0 (mc), 5.0 (mc), 6.6 (s), 6.7 (d), 6.8 (s), 7.0 (d), 7.4 ppm (t) | ca. 1:2 |
| 46 | 3,5-di-Me-Ph | 5-methyl-2-furanyl | $d_6$-DMSO: δ = 2.15(s), 2.2 (s), 2.9 (mc), 3.2 (mc), 3.8 (mc), 4.9 (br s), 5.9 (d), 6.0 (d), 6.8 (mc), 7.2 ppm (br s) | ca. 1:1.5 |
| 47 | 3,5-di-Me-Ph | 6-bromo-2-furanyl | $d_6$-DMSO: δ = 2.2 (s), 2.95 (mc), 3.2 (mc), 3.75 (mc), 4.9 (Br s), 6.2 (d), 6.45 (d), 6.7-6.8 (m), 7.3 ppm (br s) | ca. 1:2 |
| 48 | 3,5-di-Me-Ph | 4,5-dimethyl-2-furanyl | $d_6$-DMSO: δ = 1.85 (s), 2.15 (s), 2.2 (s), 2.9 (mc), | ca. 1:1 |

TABLE II-continued

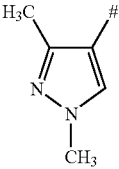
(I)

| Ex. no. | Ar | Het | Physico-chemical data (m.p. [° C.]; ¹H-NMR [ppm]) | Remark for stereogenic centre at * |
|---|---|---|---|---|
| | | | 3.2 (mc), 3.7 (mc), 4.85 (br s), 5.95 (s), 6.8 ppm (mc) | |
| 49 | 3,5-di-Me-Ph | 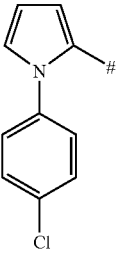 | CDCl₃: δ = 2.2 (s), 2.25 (s), 2.9-3.15 (m), 3.25 (mc), 3.55(s), 3.9 (mc), 4.95 (mc), 5.9 (s), 6.7 (s), 6.8 ppm (s) | ca. 1:1 |
| 50 | 3,5-di-Me-Ph | 4,5-di-chloro-3-thienyl | 88.00-90.00° C. | ca. 1:1.5 |
| 51 | 3,5-di-Me-Ph | 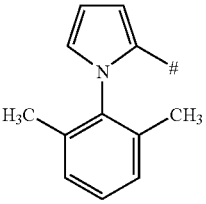 | CDCl₃: δ = 2.2 (s), 2.7 (mc), 2.9 (mc), 4.05 (mc), 6.25-6.35 (m), 6.6 (s), 6.7 (d), 6.8 (s), 7.2 (d), 7.4 ppm (d) | ca. 1:1 |
| 52 | 3,5-di-Me-Ph | 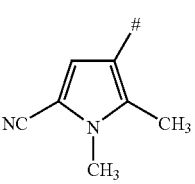 | CDCl₃: δ = 1.9 (s), 2.0 (s), 2.2 (s), 3.0 (mc), 3.2 (mc), 3.3 (mc), 4.0 (mc), 4.95 (mc), 6.2 (s), 6.3 (s), 6.5 (s), 6.7-6.8 (m), 7.05-7.2 ppm (m) | ca. 1:1 |
| 53 | 3,5-di-Me-Ph |  | d₆-DMSO: δ = 2.0 (s), 2.2 (s), 2.7 (mc), 3.0 (mc), 3.15 (mc), 3.5 (mc), 3.75 (mc), 4.8 (br s), 6.7-6.8 (m), 6.9 (s), 7.05 ppm (br s) | |
| 54 | Ph | 5-methyl-2-thienyl | 118.00-120.00° C. | racemate |
| 55 | 3-Cl-Ph | 5-methyl-2-thienyl | CDCl₃: δ = 2.4 (s), 3.05-3.3 (m), 3.9 (mc), 5.05 (mc), 6.55 (d), 6.6 (d), 7.0-7.2 ppm (m) | racemate |
| 56 | 3-Me-Ph | 5-methyl-2-thienyl | CDCl₃: δ = 2.3 (s), 2.45 (s), 3.1-3.3 (m), 3.9 (mc), 5.1 (mc), 6.55 (d), 6.65 (d), 6.9-7.3 ppm (m) | racemate |
| 57 | 4-Me-Ph | 5-methyl-2-thienyl | CDCl₃: δ = 2.3 (s), 2.45 (s), 3.1-3.3 (m), 3.9 (mc), 5.1 (mc), 6.5-6.65 (m), 7.0 ppm (mc) | racemate |
| 58 | 2-Me-Ph | 5-methyl-2-thienyl | CDCl₃: δ = 2.3 (s), 2.45 (s), 3.2-3.4 (m), 3.9 (mc), 4.7 | racemate |

TABLE II-continued

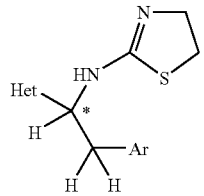

(I)

| Ex. no. | Ar | Het | Physico-chemical data (m.p. [° C.]; ¹H-NMR [ppm]) | Remark for stereogenic centre at * |
|---|---|---|---|---|
| 59 | 3,5-di-Me-Ph | 3-bromo-2-thienyl | (br s), 6.6 (s), 6.9 (s), 7.1-7.3 ppm (m) 115.00-117.00° C. | racemate | ex. = example
Me = methyl
Ph = phenyl
Ac = acetyl
DMSO = dimethyl sulfoxide
# = position of attachment in formula I
m.p. = melting point

Biological Examples

Examples of Action Against Pests

The action of the compounds of the general formulae I and II against pests was demonstrated by the following experiments:

I. Cotton Aphid (*Aphis gossypii*)

Cotton plants in the cotyledon stage (variety 'Delta Pine') are infested with approximately 100 laboratory-reared aphids by placing infested leaf sections on top of the test plants. The leaf sections are removed after 24 hours. The cotyledons of the intact plants are dipped into gradient solutions of the test compound. Aphid mortality on the treated plants, relative to mortality on check plants, is determined after 5 days.

In this test, compounds of example no. 6, 7, 8, 10, 20, 21, 22, 23, 27, 31 to 39, 43, 45 to 48, 50, 53 to 55, 57 and 59 at 300 ppm showed over 70% mortality in comparison with untreated controls.

II. Green Peach Aphid (*Myzus persicae*)

Pepper plants in the 2$^{nd}$ leaf-pair stage (variety 'California Wonder') are infested with approximately 40 laboratory-reared aphids by placing infested leaf sections on top of the test plants. The leaf sections are removed after 24 hours. The leaves of the intact plants are dipped into gradient solutions of the test compound. Aphid mortality on the treated plants, relative to mortality on check plants, is determined after 5 days.

In this test, compounds of example no. 6, 7, 8, 20, 21, 22, 23, 27, 31 to 34, 36, 37, 39, 43, 45 to 50, 53 to 57 and 59 at 300 ppm showed over 70% mortality in comparison with untreated controls.

III. Cowpea Aphid (*Aphis craccivora*)

The active compounds were formulated in 50:50 acetone: water and 0.1% (vol/vol) Alkamuls EL 620 surfactant.

Potted cowpea beans of 7-10 days of age are inoculated with aphids 24 h before treatment by clipping a leaf infested with cowpea aphid approximately 30 individuals. The treated beans are sprayed with 5 mL of the test solution using air driven hand atomizer (Devillbis atomizer) at 25 psi, allowed to air dry and kept at 25-27° C. and 50-60% humidity for 3 days. After 72 h, mortality was assessed.

In this test, compounds of example no. 32-39, 43, 46-48, 50, 53-58 and 59 at 300 ppm showed over 70% mortality in comparison with untreated controls.

IV. Silverleaf Whitefly (*Bemisia argentifolii*), Adult

The active compounds were formulated in 50:50 acetone: water and 100 ppm Kinetic® surfactant.

Selected cotton plants were grown to the cotyledon state (one plant per pot). The cotyledons were dipped into the test solution to provide complete coverage of the foliage and placed in a well-vented area to dry. Each pot with treated seedling was placed in a plastic cup and 10 to 12 whitefly adults (approximately 3-5 day old) were introduced. The insects were collected using an aspirator and an 0.6 cm, non-toxic Tygon® tubing (R-3603) connected to a barrier pipette tip. The tip, containing the collected insects, was then gently inserted into the soil containing the treated plant, allowing insects to crawl out of the tip to reach the foliage for feeding. The cups were covered with a reusable screened lid (150 micron mesh polyester screen PeCap from Tetko Inc). Test plants were maintained in the holding room at about 25° C. and 20-40% relative humidity for 3 days avoiding direct exposure to the fluorescent light (24 hour photoperiod) to prevent trapping of heat inside the cup. Mortality was assessed 3 days after treatment of the plants.

In this test, compound of example no. 35-36, 43, 50 and 59 at 300 ppm showed over 70% mortality in comparison with untreated controls.

The invention claimed is:

1. 1-(Azolin-2-yl)-amino-2-aryl-1-hetaryl-ethane compounds of the general formula I

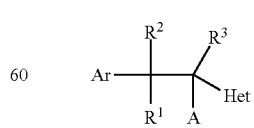

(I)

wherein $R^1$, $R^2$, $R^3$ are, independently of each other, selected from the group consisting of hydrogen, $C_1$-$C_6$-alkyl, $C_1$-$C_6$-haloalkyl, $C_3$-$C_6$-cycloalkyl, and $C_3$-$C_6$-halocycloalkyl, wherein 1, 2 or 3 hydrogen atoms in the aforementioned aliphatic radicals may be replaced, independently of one another, by a radical selected from the group consisting of cyano, nitro, hydroxy, mercapto, amino, carboxyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, and wherein $C_3$-$C_6$-cycloalkyl and $C_3$-$C_6$-halocycloalkyl may also carry 1, 2, 3, 4 or 5 radicals selected from the group consisting of $C_1$-$C_6$-alkyl and $C_1$-$C_6$-haloalkyl, phenyl or benzyl, wherein the phenyl ring in the last two mentioned radicals may be unsubstituted or may carry 1, 2, 3, 4 or 5 radicals which are, independently of each other, by a radical selected from the group consisting of halogen, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy and $C_1$-$C_6$-haloalkoxy;

A is a radical of the formulae $A^1$ or $A^2$:

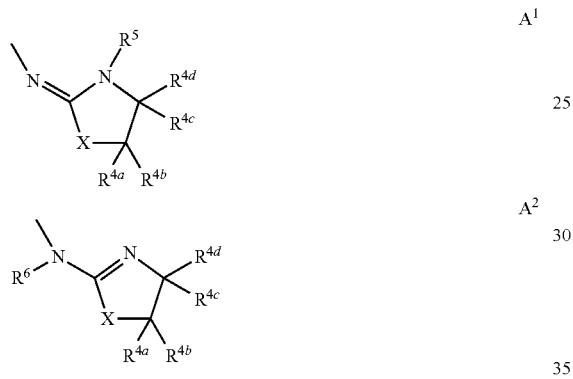

wherein

X is sulfur, oxygen or $NR^7$;

$R^{4a}$, $R^{4b}$, $R^{4c}$, $R^{4d}$ are, independently of each other, selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl and $C_3$-$C_6$-halocycloalkyl, wherein 1, 2 or 3 hydrogen atoms in the aforementioned aliphatic radicals may be replaced, independently of one another, by a radical selected from the group consisting of cyano, nitro, hydroxy, mercapto, amino, carboxyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio and wherein $C_3$-$C_6$-cycloalkyl and $C_3$-$C_6$-halocycloalkyl may also carry 1, 2, 3, 4 or 5 radicals selected from the group consisting of $C_1$-$C_6$-alkyl and $C_1$-$C_6$-haloalkyl;

$R^5$, $R^6$, $R^7$ are, independently of each other, selected from the group consisting of hydrogen, cyano, nitro, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkoxy)methylen, $C_1$-$C_6$-alkylthio, $C_1$-$C_6$-alkylsulfinyl, $C_1$-$C_6$-alkylsulfonyl, wherein the aliphatic moieties in the aforementioned radicals may be unsubstituted, partially or completely halogenated and/or may carry 1, 2 or 3 radicals, which are independently of one another, selected from the group consisting of cyano, nitro, hydroxy, mercapto, amino, carboxyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio and wherein $C_3$-$C_8$-cycloalkyl and $C_3$-$C_8$-halocycloalkyl may also carry 1, 2, 3, 4 or 5 radicals selected from the group consisting of $C_1$-$C_6$-alkyl and $C_1$-$C_6$-haloalkyl, $C(O)NR^aR^b$, $(SO_2)NR^aR^b$ or $C(=O)R^c$, phenyl, phenyloxy or benzyl, wherein the phenyl ring in each of the last three mentioned radicals may be unsubstituted or may carry 1, 2, 3, 4 or 5 radicals, independently of one another selected from the group consisting of halogen, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy and $C_1$-$C_6$-haloalkoxy radicals;

Het is a 5- or 6-membered heteroaromatic ring which contains 1, 2, 3 or 4 heteroatoms selected from the group consisting of oxygen, nitrogen and sulfur as ring members, wherein the heteroaromatic ring may be fused to a ring selected from the group consisting of phenyl, a saturated or partially unsaturated 5-, 6-, or 7-membered carbocycle and a fused 5-, 6- or 7-membered saturated, partially unsaturated or aromatic heterocycle, which contains 1, 2 or 3 heteroatoms selected from the group consisting of oxygen, sulfur and nitrogen atoms as ring members, and wherein the 5- or 6-membered heteroaromatic ring and/or the respective fused ring carry at their carbon atoms any combination of m radicals $R^8$ and/or may carry at its nitrogen atom, if present, a radical $R^9$ or oxygen:

m is 0, 1, 2, 3 or 4, $R^8$ is selected from the group consisting of halogen, OH, SH, $NH_2$, $SO_3H$, COOH, cyano, azido, nitro, $CONH_2$, $CSNH_2$, CH=N—OH, CH=N—O—($C_1$-$C_6$)-alkyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkylamino, $C_2$-$C_6$-alkenylamino, $C_2$-$C_6$-alkynylamino, di($C_1$-$C_6$-alkyl)amino, di($C_2$-$C_6$-alkenyl)amino, di($C_2$-$C_6$-alkynyl)amino, $C_1$-$C_6$-alkylthio, $C_2$-$C_6$-alkenylthio, $C_2$-$C_6$-alkynylthio, $C_1$-$C_6$-alkylsulfonyl, $C_2$-$C_6$-alkenylsulfonyl, $C_2$-$C_6$-alkynylsulfonyl, ($C_1$-$C_6$-alkyl)carbonyl, ($C_2$-$C_6$-alkenyl)-carbonyl, ($C_2$-$C_6$-alkynyl)-carbonyl, $C_1$-$C_6$-alkoxy, $C_2$-$C_6$-alkenyloxy, $C_2$-$C_6$-alkynyloxy, ($C_1$-$C_6$-alkoxy)carbonyl, ($C_2$-$C_6$-alkenyloxy)carbonyl, ($C_2$-$C_6$-alkynyloxy)-carbonyl, ($C_1$-$C_6$-alkyl)carbonyloxy, ($C_2$-$C_6$-alkenyl-)carbonyl-oxy, ($C_2$-$C_6$-alkynyl)carbonyloxy, ($C_1$-$C_6$-alkyl)carbonyl-amino, ($C_2$-$C_6$-alkenyl)carbonyl-amino, and ($C_2$-$C_6$-alkynyl)carbonyl-amino, wherein the aliphatic parts of the aforementioned groups may be unsubstituted, partially or completely halogenated or may carry any combination of one, two or three radicals, independently of one another selected from the group consisting of cyano, nitro, hydroxy, mercapto, amino, carboxyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-haloalkyl and $C_1$-$C_6$-alkylthio;

$C(O)NR^aR^b$, $(SO_2)NR^aR^b$, $C(=O)R^c$, $C(=S)R^c$, a radical Y-Ar' or a radical Y-Cy, wherein Y is a single bond, O, S, NH, $C_1$-$C_6$-alkandiyl or $C_1$-$C_6$-alkandiyloxy, Ar' is phenyl, naphthyl or a mono- or bicyclic 5- to 10-membered heteroaromatic ring, which contains 1, 2, 3 or 4 heteroatoms selected from the group consisting of oxygen, sulfur and nitrogen atoms as ring members, wherein Ar' is unsubstituted or may carry any combination of 1, 2, 3, 4 or 5 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

Cy is $C_3$-$C_8$-cycloalkyl, which is unsubstituted or may carry any combination of 1, 2, 3, 4 or 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

$R^9$ has one of the meanings given for $R^5$;

Ar is a phenyl or naphthyl which carry any combination of n radicals $R^{10}$:

n is 0, 1, 2, 3, 4 or 5, $R^{10}$ has one of the meanings given for $R^8$;

and wherein two radicals $R^{10}$ that are bound to adjacent carbon atoms of the phenyl ring may also form, together with said carbon atoms, a fused benzene ring, a fused saturated or partially unsaturated 5-, 6-, or 7-membered carbocycle or a fused 5-, 6- or 7-membered saturated, partially unsaturated or aromatic heterocycle, which contains 1, 2, 3 or 4 heteroatoms selected from oxygen, sulfur and nitrogen atoms as ring members, and wherein the fused ring is unsubstituted or may carry 1, 2, 3 or 4 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

and wherein $R^a$ and $R^b$ are each independently from one another selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, and $C_2$-$C_6$-haloalkynyl, wherein 1, 2 or 3 hydrogen atoms in the aforementioned aliphatic radicals may be replaced, independently of one another, by a radical selected from the group consisting of cyano, nitro, hydroxy, mercapto, amino, carboxyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-haloalkyl and $C_1$-$C_6$-alkylthio; and $R^c$ is selected from the group consisting of hydrogen, $C_1$-$C_6$ alkyl, $C_2$-$C_6$-alkenyl, $C_2$-$C_6$-alkynyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)amino, hydrazino, ($C_1$-$C_6$-alkyl)hydrazino, and di($C_1$-$C_6$-alkyl)hydrazino, wherein the aliphatic parts of the aforementioned groups may be unsubstituted, partially or completely halogenated or may carry any combination of one, two or three radicals, independently of one another selected from the group consisting of cyano, nitro, hydroxy, mercapto, amino, carboxyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-haloalkyl and $C_1$-$C_6$-alkylthio, phenyl, and a mono- or bicyclic 5- to 10-membered heteroaromatic ring, which contains 1, 2, 3 or 4 heteroatoms selected from the group consisting of oxygen, sulfur and nitrogen atoms as ring members, wherein phenyl and the heteroaromatic ring are unsubstituted or may carry any combination of 1, 2, 3, 4 or 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

and the salts thereof.

2. The compound of claim 1, wherein Het is selected from the radicals of the formulae Het.1 to Het.57 as defined herein:

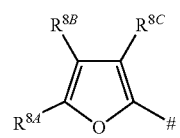

Het.1

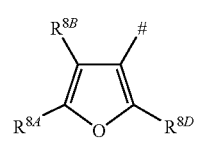

Het.2

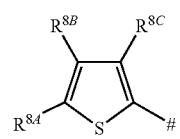

Het.3

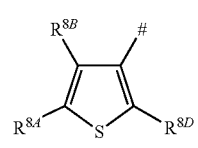

Het.4

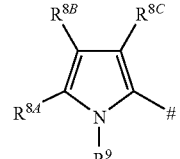

Het.5

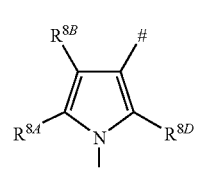

Het.6

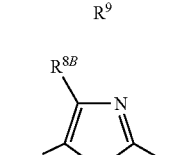

Het.7

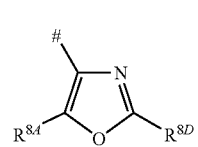

Het.8

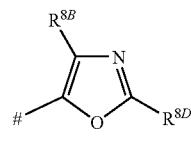

Het.9

| | |
|---|---|
| Het.10 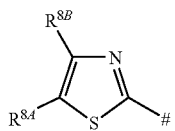 | Het.20 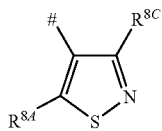 |
| Het.11 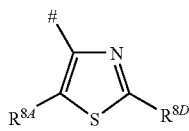 | Het.21 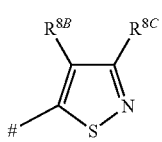 |
| Het.12 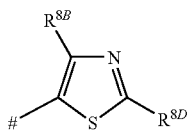 | Het.22 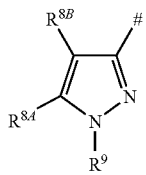 |
| Het.13 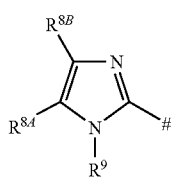 | Het.23 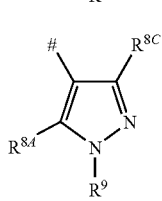 |
| Het.14 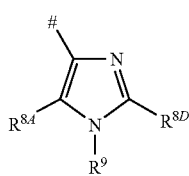 | Het.24 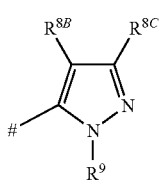 |
| Het.15 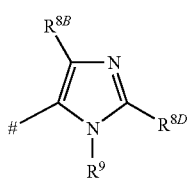 | Het.25 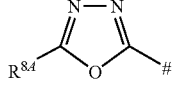 |
| Het.16 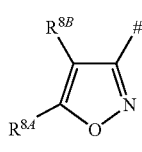 | Het.26 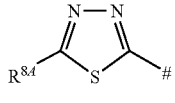 |
| Het.17 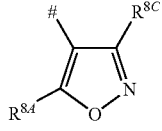 | Het.27 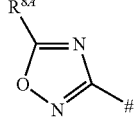 |
| Het.18 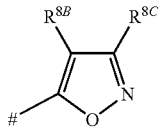 | Het.28 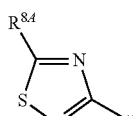 |
| Het.19 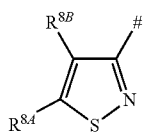 | Het.29 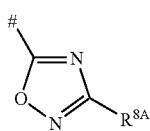 |

| | | |
|---|---|---|
| 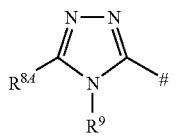 | Het.31 | |
| 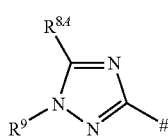 | Het.32 | |
| 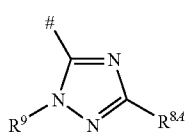 | Het.33 | |
| 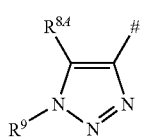 | Het.34 | |
| 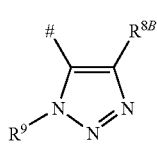 | Het.35 | |
| 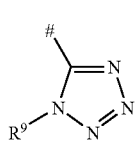 | Het.36 | |
| 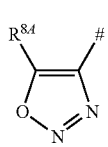 | Het.37 | |
| 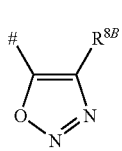 | Het.38 | |
| 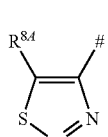 | Het.39 | |
| 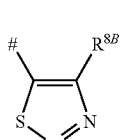 | Het.40 | |
| 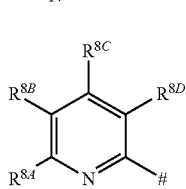 | Het.41 | |
| | | |
|---|---|---|
| 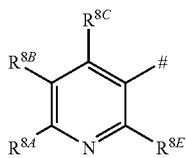 | Het.42 | |
| 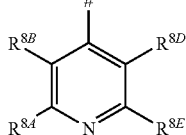 | Het.43 | |
| 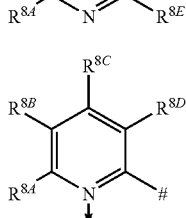 | Het.44 | |
| 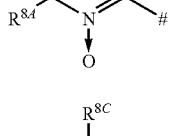 | Het.45 | |
| 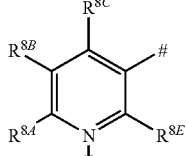 | Het.46 | |
| 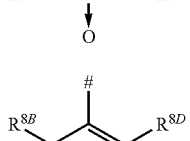 | Het.47 | |
| 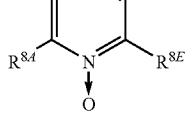 | Het.48 | |
| 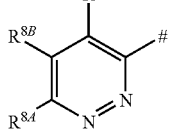 | Het.49 | |
| 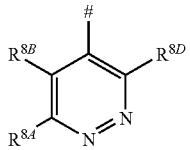 | Het.50 | |
| 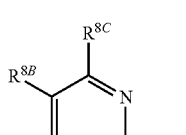 | | |
| 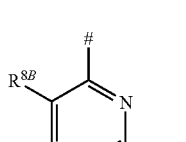 | | |

-continued

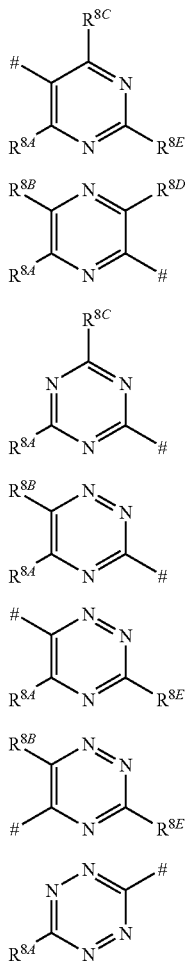

wherein # denotes the position of attachment in formula I and wherein $R^{8A}$, $R^{8B}$, $R^{8C}$, $R^{8D}$ and $R^{8E}$, independently of each other, are hydrogen or have one of the meanings given for $R^8$.

3. The compound of claim 2, wherein Het is selected from the radicals of formulae Het.1, Het. 2, Het.3, and Het.4.

4. The compound of claim 1, wherein $R^1$, $R^2$ and $R^3$ are hydrogen.

5. The compound of claim 1, wherein $R^{4a}$, $R^{4b}$, $R^{4c}$ and $R^{4d}$ are hydrogen.

6. The compound of claim 1, wherein $R^5$, $R^6$ are each independently selected from the group consisting of hydrogen, cyano, nitro, $C(=O)R^c$ and $C_1$-$C_6$-alkyl.

7. The compound of claim 1, wherein $R^5$ and $R^6$ are hydrogen.

8. The compound of claim 1, wherein at least one of the integers m or n is different from 0 and wherein $R^8$, $R^{10}$ are, independently from one another, selected from the group consisting of halogen, OH, SH, $NH_2$, $SO_3H$, COOH, cyano, $CONH_2$, $C(=O)R^c$, $C_1$-$C_6$-alkyl, $C_3$-$C_8$-cycloalkyl, $C_1$-$C_6$-alkylamino, and di($C_1$-$C_6$-alkyl)amino, wherein the aliphatic moieties in the aforementioned radicals may be unsubstituted, partially or completely halogenated and/or may carry 1, 2 or 3 radicals, which are independently of one another, selected from the group consisting of cyano, nitro, hydroxy, mercapto, amino, carboxyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio and wherein $C_3$-$C_8$-cycloalkyl may also carry 1, 2, 3, 4 or 5 radicals selected from the group consisting of $C_1$-$C_6$-alkyl and $C_1$-$C_6$-haloalkyl.

9. The compound of claim 1, wherein X is sulfur.

10. The compound of claim 1, wherein X is oxygen.

11. The compound of claim 1, wherein X is $NR^7$.

12. The compound of claim 11, wherein $R^7$ is selected from the group consisting of hydrogen, a radical $C(=O)R^c$ and $C_1$-$C_6$-alkyl.

13. The compound of claim 1, wherein m is 1, 2 or 3.

14. The compound of claim 1, wherein n is 1, 2 or 3.

15. An agricultural or veterinary composition comprising at least one 1-(azolin-2-yl)-amino-2-aryl-1-hetaryl-ethane compound of formula I as defined in claim 1 and/or an agriculturally or veterinary useful salt thereof and at least one agriculturally or veterinary acceptable carrier.

16. A method for treating insects, arachnids and nematodes by treating said insects, arachnids and nematodes with at least one 1-(azolin-2-yl)-amino-2-aryl-1-hetaryl-ethane compound of formula I as defined in claim 1 and/or salt thereof.

17. A method for the protection of seeds from soil insects and of the seedlings' roots and shoots from insects comprising contacting the seeds before sowing and/or after pregermination with at least one 1-(azolin-2-yl)-amino-2-aryl-1-hetaryl-ethane compound of formula I as defined in claim 1 and/or salt thereof.

18. An agricultural composition comprising a seed and at least one 1-(azolin-2-yl)-amino-2-aryl-1-hetaryl-ethane compound of formula I as defined in claim 1 and/or a salt thereof.

19. An 1-(aminothiocarbonylamino)-2-aryl-1-hetaryl-ethane compound of the general formula II

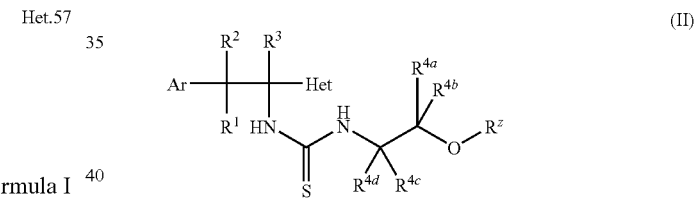

(II)

wherein $R^1$, $R^2$, $R^3$ are, independently of each other, selected from the group consisting of hydrogen, $C_1$-$C_6$-alkyl, $C_1$-$C_6$-haloalkyl, $C_3$-$C_6$-cycloalkyl, and $C_3$-$C_6$-halocycloalkyl, wherein 1, 2 or 3 hydrogen atoms in the aforementioned aliphatic radicals may be replaced, independently of one another, by a radical selected from the group consisting of cyano, nitro, hydroxy, mercapto, amino, carboxyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, and wherein $C_3$-$C_6$-cycloalkyl and $C_3$-$C_6$-halocycloalkyl may also carry 1, 2, 3, 4 or 5 radicals selected from the group consisting of $C_1$-$C_6$-alkyl and $C_1$-$C_6$-haloalkyl, phenyl or benzyl, wherein the phenyl ring in the last two mentioned radicals may be unsubstituted or may carry 1, 2, 3, 4 or 5 radicals which are, independently of each other, by a radical selected from the group consisting of halogen, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy and $C_1$-$C_6$-haloalkoxy;

Het is a 5- or 6-membered heteroaromatic ring which contains 1, 2, 3 or 4 heteroatoms selected from the group consisting of oxygen, nitrogen and sulfur as ring members, wherein the heteroaromatic ring may be fused to a ring selected from the group consisting of phenyl, a saturated or partially unsaturated 5-, 6-, or 7-membered carbocycle and a fused 5-, 6- or 7-membered saturated, partially unsaturated or aromatic heterocycle, which contains 1, 2 or 3 heteroatoms selected from the group consisting of oxygen, sulfur and nitrogen atoms as ring members, and wherein the 5- or 6-membered heteroaromatic ring and/or the respective fused ring carry at their carbon atoms any combination of m radicals $R^8$ and/or may carry at its nitrogen atom, if present, a radical $R^9$ or oxygen:

m is 0, 1, 2, 3 or 4, $R^8$ is selected from the group consisting of halogen, OH, SH, $NH_2$, $SO_3H$, COOH, cyano, azido, nitro, $CONH_2$, $CSNH_2$, CH=N—OH, CH=N—O—($C_1$-$C_6$)-alkyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkylamino, $C_2$-$C_6$-alkenylamino, $C_2$-$C_6$-alkynylamino, di($C_1$-$C_6$-alkyl)amino, di($C_2$-$C_6$-alkenyl)amino, di($C_2$-$C_6$-alkynyl)amino, $C_1$-$C_6$-alkylthio, $C_2$-$C_6$-alkenylthio, $C_2$-$C_6$-alkynylthio, $C_1$-$C_6$-alkylsulfonyl, $C_2$-$C_6$-alkenylsulfonyl, $C_2$-$C_6$-alkynylsulfonyl, ($C_1$-$C_6$-alkyl)carbonyl, ($C_2$-$C_6$-alkenyl)-carbonyl, ($C_2$-$C_6$-alkynyl)-carbonyl, $C_1$-$C_6$-alkoxy, $C_2$-$C_6$-alkenyloxy, $C_2$-$C_6$-alkynyloxy, ($C_1$-$C_6$-alkoxy)carbonyl, ($C_2$-$C_6$-alkenyloxy)carbonyl, ($C_2$-$C_6$-alkynyloxy)-carbonyl, ($C_1$-$C_6$-alkyl)carbonyloxy, ($C_2$-$C_6$-alkenyl-)carbonyl-oxy, ($C_2$-$C_6$-alkynyl)carbonyloxy, ($C_1$-$C_6$-alkyl)carbonyl-amino, ($C_2$-$C_6$-alkenyl)carbonyl-amino, and ($C_2$-$C_6$-alkynyl)carbonyl-amino, wherein the aliphatic parts of the aforementioned groups may be unsubstituted, partially or completely halogenated or may carry any combination of one, two or three radicals, independently of one another selected from the group consisting of cyano, nitro, hydroxy, mercapto, amino, carboxyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-haloalkyl and $C_1$-$C_6$-alkylthio;

$C(O)NR^aR^b$, $(SO_2)NR^aR^b$, $C(=O)R^c$, $C(=S)R^c$, a radical Y-Ar' or a radical Y-Cy, wherein Y is a single bond, O, S, NH, $C_1$-$C_6$-alkandiyl or $C_1$-$C_6$-alkandiyloxy, Ar' is phenyl, naphthyl or a mono- or bicyclic 5- to 10-membered heteroaromatic ring, which contains 1, 2, 3 or 4 heteroatoms selected from the group consisting of oxygen, sulfur and nitrogen atoms as ring members, wherein Ar' is unsubstituted or may carry any combination of 1, 2, 3, 4 or 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

Cy is $C_3$-$C_8$-cycloalkyl, which is unsubstituted or may carry any combination of 1, 2, 3, 4 or 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

$R^9$ has one of the meanings given for $R^5$;

Ar is a phenyl or naphthyl which carry any combination of n radicals $R^{10}$:

n is 0, 1, 2, 3, 4 or 5, $R^{10}$ has one of the meanings given for $R^8$;

and wherein two radicals $R^{10}$ that are bound to adjacent carbon atoms of the phenyl ring may also form, together with said carbon atoms, a fused benzene ring, a fused saturated or partially unsaturated 5-, 6-, or 7-membered carbocycle or a fused 5-, 6- or 7-membered saturated, partially unsaturated or aromatic heterocycle, which contains 1, 2, 3 or 4 heteroatoms selected from oxygen, sulfur and nitrogen atoms as ring members, and wherein the fused ring is unsubstituted or may carry 1, 2, 3 or 4 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

and wherein $R^z$ is hydrogen, or acetyl and the salts thereof.

20. An agricultural or veterinary composition comprising at least one 1-(aminothiocarbonylamino)-2-aryl-1-hetaryl-ethane compound of the formula II as defined in claim 19 and/or an agriculturally or veterinary useful salt thereof and at least one agriculturally or veterinary acceptable carrier material.

21. A method for treating insects, arachnids and nematodes by treating the insects, arachnids and nematodes with at least one 1-(aminothiocarbonylamino)-2-aryl-1-hetaryl-ethane compound of the formula II as defined in claim 19 and/or salt thereof.

22. A method for the protection of seeds from soil insects and of the seedlings' roots and shoots from insects comprising contacting the seeds before sowing and/or after pregermination with at least one 1-(aminothiocarbonylamino)-2-aryl-1-hetaryl-ethane compound of the formula II as defined in claim 19 and/or salt thereof.

23. An agricultural composition comprising a seed and comprising at least one 1-(aminothiocarbonylamino)-2-aryl-1-hetaryl-ethane compound of the formula II as defined in claim 19 and/or a salt thereof.

* * * * *

UNITED STATES PATENT AND TRADEMARK OFFICE
CERTIFICATE OF CORRECTION

| | | |
|---|---|---|
| PATENT NO. | : 7,989,394 B2 | Page 1 of 1 |
| APPLICATION NO. | : 12/305419 | |
| DATED | : August 2, 2011 | |
| INVENTOR(S) | : Markus Kordes et al. | |

It is certified that error appears in the above-identified patent and that said Letters Patent is hereby corrected as shown below:

Column 99, Line 41, after "$C_1$-$C_6$-haloalkyl, insert -- $C_1$-$C_6$-alkylamino, --

Column 101, Line 1, after "$C_1$-$C_6$-alkyl, insert -- $C_1$-$C_6$-haloalkyl, --

Signed and Sealed this

Eighteenth Day of October, 2011

David J. Kappos
*Director of the United States Patent and Trademark Office*